United States Patent
Hopkins et al.

(10) Patent No.: US 10,618,887 B2
(45) Date of Patent: *Apr. 14, 2020

(54) PYRIMIDINYL TYROSINE KINASE INHIBITORS

(71) Applicants: Sunesis Pharmaceuticals, Inc., South San Francisco, CA (US); Biogen MA Inc., Cambridge, MA (US)

(72) Inventors: Brian T. Hopkins, Newton, MA (US); Timothy R. Chan, Newton, MA (US); Tracy J. Jenkins, Watertown, MA (US); Patrick Conlon, Wakefield, MA (US); Xiongwei Cai, Arlington, MA (US); Michael Humora, Carnbury, NJ (US); Xianglin Shi, Cambridge, MA (US); Ross A. Miller, South Plainfield, NJ (US); Andrew Thompson, Portola Valley, CA (US)

(73) Assignees: Sunesis Pharmaceuticals, Inc., South San Francisco, CA (US); Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/911,546

(22) Filed: Mar. 5, 2018

(65) Prior Publication Data

US 2019/0047986 A1    Feb. 14, 2019

Related U.S. Application Data

(63) Continuation of application No. 15/196,389, filed on Jun. 29, 2016, now Pat. No. 9,944,622, which is a continuation of application No. 14/406,315, filed as application No. PCT/US2013/044800 on Jun. 7, 2013, now Pat. No. 9,394,277.

(60) Provisional application No. 61/657,360, filed on Jun. 8, 2012.

(51) Int. Cl.
    C07D 401/04    (2006.01)
    C07D 401/14    (2006.01)

(52) U.S. Cl.
    CPC .................. C07D 401/14 (2013.01)

(58) Field of Classification Search
    CPC ............... C07D 401/14; A61K 31/506
    See application file for complete search history.

(56) References Cited

U.S. PATENT DOCUMENTS

| | | |
|---|---|---|
| 4,528,138 A | 7/1985 | Varma et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 6,635,762 B1 | 10/2003 | Blumenkopf et al. |
| 7,300,941 B2 * | 11/2007 | Aslanian .......... A61K 31/435 514/275 |
| 7,312,226 B2 | 12/2007 | Hurley et al. |
| 7,326,712 B2 | 2/2008 | Hurley et al. |
| 7,326,713 B2 | 2/2008 | Hurley et al. |
| 7,335,662 B2 | 2/2008 | Hurley et al. |
| 7,423,043 B2 | 9/2008 | Rawlins et al. |
| 7,528,143 B2 | 5/2009 | Noronha et al. |
| 8,362,065 B2 | 1/2013 | Liu et al. |
| 8,685,880 B2 | 4/2014 | Hommeltoft |
| 8,785,440 B2 | 7/2014 | Bui et al. |
| 9,029,359 B2 | 5/2015 | Bui et al. |
| 9,249,146 B2 | 2/2016 | Bui et al. |
| 9,266,890 B2 | 2/2016 | Gray et al. |
| 9,273,028 B2 | 3/2016 | Hopkins et al. |
| 9,353,087 B2 | 5/2016 | Hopkins et al. |
| 9,394,277 B2 * | 7/2016 | Hopkins .......... C07D 401/14 |
| 9,790,229 B2 | 10/2017 | Bui et al. |
| 9,809,577 B2 | 11/2017 | Hopkins et al. |
| 9,944,622 B2 * | 4/2018 | Hopkins .......... C07D 401/14 |
| 2002/0150947 A1 | 10/2002 | Erlanson et al. |
| 2005/0143372 A1 | 6/2005 | Ghosh et al. |
| 2006/0189638 A1 | 8/2006 | Rawlins et al. |
| 2006/0281700 A1 | 12/2006 | Baumann et al. |
| 2006/0281764 A1 | 12/2006 | Gaul et al. |
| 2007/0142369 A1 * | 6/2007 | van Heek .......... A61K 31/00 514/227.5 |
| 2008/0058348 A1 | 3/2008 | Lefrancois et al. |
| 2008/0108636 A1 | 5/2008 | Honigberg et al. |
| 2008/0119487 A1 * | 5/2008 | Aslanian .......... A61K 31/435 514/255.04 |
| 2008/0300242 A1 | 12/2008 | Kuntz et al. |
| 2010/0093692 A1 * | 4/2010 | Aslanian .......... A61K 31/4545 514/210.18 |

(Continued)

FOREIGN PATENT DOCUMENTS

| CN | 101610676 A | 12/2009 |
|---|---|---|
| CN | 101932573 A | 12/2010 |

(Continued)

OTHER PUBLICATIONS

Author Not Known, A to Z List of Cancers, National Cancer Institute, 22 pages, retrieved on May 29, 2014 <http://www.cancer.gov/cancertopics/types/alphalist>.

Banda, N.K. et al., Complement activation pathways in murine immune complex-induced arthritis and in C3a and C5a generation in vitro, Clin. Exp. Immunol., 159(1):100-8 (2010).

Berge S.M. et al., Pharmaceutical salts, Journal of Pharmaceutical Sciences, 66(1):1-19 (1977).

Bhatia, S.K. and Rose, N.R., Autoimmunity and autoimmune disease, 6 Principles of Medical Biology, Chapter 13, pp. 239-263 (1996).

Brinkmann, V. et al., Fingolimod (FTY720): discovery and development of an oral drug to treat multiple sclerosis, Nat. Rev. Drug. Discov., 9(11):883-97 (2010).

(Continued)

*Primary Examiner* — Alexander R Pagano
(74) *Attorney, Agent, or Firm* — Cooley LLP; Heidi A. Erlacher; Christine E. Dunne

(57) ABSTRACT

The present invention provides compounds and compositions thereof which are useful as inhibitors of Bruton's tyrosine kinase and which exhibit desirable characteristics for the same.

17 Claims, No Drawings

(56) References Cited

U.S. PATENT DOCUMENTS

| | | |
|---|---|---|
| 2010/0105676 A1 | 4/2010 | Liu et al. |
| 2010/0160292 A1 | 6/2010 | Whitney et al. |
| 2012/0004096 A1 | 1/2012 | Hommeltoft |
| 2012/0040961 A1 | 2/2012 | Gray et al. |
| 2012/0058996 A1 | 3/2012 | Liu et al. |
| 2012/0157442 A1 | 6/2012 | Bui et al. |
| 2012/0157443 A1 | 6/2012 | Bui et al. |
| 2013/0345192 A1 | 12/2013 | Hopkins et al. |
| 2014/0308238 A1 | 10/2014 | Rubin-Bejerano et al. |
| 2014/0309212 A1 | 10/2014 | Bui et al. |
| 2015/0126528 A1 | 5/2015 | Hopkins et al. |
| 2015/0158843 A1 | 6/2015 | Hopkins et al. |
| 2016/0304494 A1 | 10/2016 | Hopkins et al. |
| 2016/0311802 A1 | 10/2016 | Hopkins et al. |
| 2016/0318935 A1 | 11/2016 | Hopkins et al. |
| 2016/0376281 A1 | 12/2016 | Bui et al. |
| 2017/0027956 A1 | 2/2017 | Hopkins et al. |
| 2017/0114039 A1 | 4/2017 | Hopkins et al. |
| 2018/0065974 A1 | 3/2018 | Bui et al. |

FOREIGN PATENT DOCUMENTS

| | | |
|---|---|---|
| CN | 102159214 A | 8/2011 |
| JP | 2008-519059 A | 6/2008 |
| JP | 2010-502751 A | 1/2010 |
| JP | 2013-503905 A | 2/2013 |
| TW | 201120040 A | 6/2011 |
| WO | WO-96/05309 A2 | 2/1996 |
| WO | WO 99/65909 A1 | 12/1999 |
| WO | WO 2001/070673 A2 | 9/2001 |
| WO | WO 2001/081347 A2 | 11/2001 |
| WO | WO 02/00661 A1 | 1/2002 |
| WO | WO-02/32893 A2 | 4/2002 |
| WO | WO 03/037898 A1 | 5/2003 |
| WO | WO 2004/065380 A1 | 8/2004 |
| WO | WO 2005/117909 A2 | 12/2005 |
| WO | WO 2006/028290 A1 | 3/2006 |
| WO | WO 2006/060461 A1 | 6/2006 |
| WO | WO 2006/071819 A1 | 7/2006 |
| WO | WO 2006/071875 A1 | 7/2006 |
| WO | WO 2007/011065 A2 | 1/2007 |
| WO | WO 2008/005368 A1 | 1/2008 |
| WO | WO 2008/012635 A2 | 1/2008 |
| WO | WO 2008/014307 A2 | 1/2008 |
| WO | WO-2008/039218 A2 | 4/2008 |
| WO | WO 2008/144253 A1 | 11/2008 |
| WO | WO-2009/098144 A1 | 8/2009 |
| WO | WO-2010/009342 A2 | 1/2010 |
| WO | WO 2010/136423 A1 | 2/2010 |
| WO | WO-2011/029043 A1 | 3/2011 |
| WO | WO-2011/029046 A1 | 3/2011 |
| WO | WO-2012/058645 A1 | 5/2012 |
| WO | WO-2013/185082 A2 | 12/2013 |
| WO | WO-2013/185084 A1 | 12/2013 |
| WO | WO 2016/054627 A1 | 4/2016 |

OTHER PUBLICATIONS

Brown, A.M. and Rampe, D., Drug-Induced Long QT Syndrome: Is HERG the Root of All Evil, Pharmaceutical News, 7(4):15-20 (2000).
Chan, O.T. et al., The central and multiple roles of B cells in lupus pathogenesis, Immunol. Rev., 169:107-21 (1999).
Cohen, S.B. et al., REFLEX Trial Group. Rituximab for rheumatoid arthritis refractory to antitumor necrosis factor therapy: Results of a multicenter, randomized, double-blind, placebocontrolled, phase III trial evaluating primary efficacy and safety at twenty-four weeks, Arthritis Rheum., 54(9):2793-806 (2006).
Coughlin, C.M. et al., Approaches and limitations of phosphatidylinositol-3-kinase pathway activation status as a predictive biomarker in the clinical development of targeted therapy, Breast Cancer Res. Treat., 124(1):1-11 (2010).
D'Ambrosio, D. et al., Chemokine receptors in inflammation: an overview, J. Immunol. Methods, 273(1-2):3-13 (2003).
Denison, T.A. and Bae, Y.H., Heterogeneity of Cancers and Its Implication for Targeted Drug Delivery, Cancer Targeted Drug Delivery: An Elusive Dream, Bae, Y.H. et al., eds, pp. 337-362 (2013).
Fabbro, D. et al., Targeting Cancer with Small-Molecular-Weight Kinase Inhibitors, Kinase Inhibitors, Methods in Molecular Biology, Ed. Kuster, B., Chapter 1, 765, 46 pages (2012).
Fine, H.A., Neoplasms of the Central Nervous System, 2 Cancer Principles and Practice of Oncology, 5th Edition, Eds. DeVita Jr., V.T. et al., pp. 1834-1887 (2005).
Flemming, A., Drug delivery: Nanobioconjugate shrinks brain tumours, Nat. Rev. Drug Discov., 9(12):917 (2010).
Flemming, A., Target Discovery: Blocking BTK in B-cell disorders, Nature Reviews I Drug Discover, vol. 9, 1 page (2010).
Furie, R. et al., BLISS-76 Study Group. A phase III, randomized, placebo-controlled study of belimumab, a monoclonal antibody that inhibits B lymphocyte stimulator, in patients with systemic lupus erythematosus, Arthritis Rheum., 63(12):3918-30 (2011).
Goldschmidt, T.J. and Holmdahl, R., Therapeutic effects of monoclonal antibodies to alpha beta TCR but not to CD4 on collagen-induced arthritis in the rat, Cell Immunol, 154(1):240-8 (1994).
Hayter, S.M. and Cook, MC, Updated assessment of the prevalence, spectrum and case definition of autoimmune disease, Autoimmun. Rev., 11(10):754-65 (2012).
Helfgott, S.M. et al., Suppressive effects of anti-mu serum on the development of collagen arthritis in rats, Clin. Immunol. Immunopathol., 31(3):403-11 (1984).
Hendriks, R.W. and Kersseboom, R., Involvement of SLP-65 and Btk in tumor suppression and malignant transformation of pre-B cells, Semin. Immunol., 18(1):67-76 (2006).
Holmdahl, R. et al., Chronicity of arthritis induced with homologous type II collagen (CII) in rats is associated with anti-CII B-cell activation, J. Autoimmun., 7(6):739-52 (1994).
Honigberg, L.A. et al., The Bruton tyrosine kinase inhibitor PCI-32765 blocks B-cell activation and is efficacious in models of autoimmune disease and B-cell malignancy, Proc Natl Acad Sci U S A., 107(29):13075-80 (2010).
Judge, S.I. and Bever, C.T. Jr., Potassium channel blockers in multiple sclerosis: neuronal Kv channels and effects of symptomatic treatment, Pharmacol. Ther., 111(1):224-59 (2006).
Kagari, T. et al., Essential role of Fc gamma receptors in anti-type II collagen antibody-induced arthritis, J. Immunol., 170(8):4318-24 (2003).
Kim, K.H. et al., Imidazo[1,5-a]quinoxalines as irreversible BTK inhibitors for the treatment of rheumatoid arthritis, Bioorg. Med. Chem. Lett., 21(21):6258-63 (2011).
Koelink, P.J. et al., Targeting chemokine receptors in chronic inflammatory diseases: an extensive review, Pharmacol. Ther., 133(1):1-18 (2012).
Luo, J. et al., Principles of cancer therapy: oncogene and non-oncogene addiction, Cell, 136(5):823-37 (2009).
McDermott, U. and Settleman, J., Personalized cancer therapy with selective kinase inhibitors: an emerging paradigm in medical oncology, J. Clin. Oncol., 27(33):5650-9 (2009).
Navarra, S.V. et al., BLISS-52 Study Group. Efficacy and safety of belimumab in patients with active systemic lupus erythematosus: a randomised, placebo-controlled, phase 3 trial, Lancet, 377(9767):721-31 (2011).
Pan, Z. et al, Discovery of selective irreversible inhibitors for Bruton's tyrosine kinase, ChemMedChem., 2(1):58-61 (2007).
Panayi, G. S. et al., Pathogenesis of rheumatoid arthritis, The role of T cells and other beasts, Rheum. Dis. Clin. North Am., 27(2):317-34 (2001).
Phillips, D.P. et al., Copper-catalyzed C—N coupling of amides and nitrogen-containing heterocycles in the presence of cesium fluoride, Tetrahedron Letters, 50:7293-7296 (2009).
Sawyers, C.L., The cancer biomarker problem, Nature, 452(7187):548-52 (2008).
Stuart, J.M. et al., Type II collagen-induced arthritis in rats. Passive transfer with serum and evidence that IgG anticollagen antibodies can cause arthritis, J. Exp. Med., 155(1):1-16 (1982).

(56) References Cited

OTHER PUBLICATIONS

Su, S. et al, The Structure and Function of Btk family—A Family of Protein tyrosine Kinases, Journal of Medical Molecular Biology, 3(6):442-445 (2006) [English Abstract Only].
Sutherland, E.R. and Cherniack, R.M., Management of chronic obstructive pulmonary disease, N. Engl. J. Med., 350(26):2689-97 (2004).
Uckun, F. et al., Bruton's tyrosine kinase prevents activation of the anti-apoptotic transcription factor STAT3 and promotes apoptosis in neoplastic B-cells and B-cell precursors exposed to oxidative stress, Br. J. Haematol., 136(4):574-89 (2007).
Uckun, F.M. and Qazi, S., Bruton's tyrosine kinase as a molecular target in treatment of leukemias and lymphomas as well as inflammatory disorders and autoimmunity, Expert. Opin. Ther. Pat., 20(11):1457-70 (2010).
Vassilev, A.O. et al., Therapeutic Potential of Inhibiting Bruton's Tyrosine Kinase, (BTK), Current Pharmaceutical Design, 10:1757-1766 (2004).
Weirich, J. and Antoni, H., Rate-dependence of antiarrhythmic and proarrhythmic properties of class I and class III antiarrhythmic drugs, Basic Res. Cardiol., 93 Suppl 1:125-32 (1998).
Whyburn, L.R. et al., Reduced dosage of Bruton's tyrosine kinase uncouples B cell hyperresponsiveness from autoimmunity in lyn-/- mice, J. Immunol., 171(4):1850-8 (2003).
Yap, Y.G. and Camm, A.J., Arrhythmogenic mechanisms of nonsedating antihistamines, Clin. Exp. Allergy, 29 Suppl 3:174-8 (1999).
Zhang, Z. and Bridges, S.L. Jr., Pathogenesis of rheumatoid arthritis, Role of B lymphocytes, Rheum. Dis. Clin. North Am., 27(2):335-53 (2001).
Schousboe et al. "Effects of GABA analogs of restricted conformation on GABA transport in astrocytes and brain cortex slices and on GABA receptor binding", Journal of Neurochemistry, 1979, vol. 33(1), pp. 181-189.
1125427-13-5, ChemBridge Corporation, Database CAS Registry (Online) [last accessed Mar. 23, 2009], 1 page.
1214417-06-7, ChemBridge Corporation, Database CAS Registry (Online) [last accessed Mar. 25, 2010], 1 page.
1214612-86-8, ChemBridge Corporation, Database CAS Registry (Online) [last accessed Mar. 25 2010], 1 page.
Clinical Pharmacology and Biopharmaceutics Reviews, Center for Drug Evaluation and Research, Application No. 205552Orig1s000, submission date: Jun. 28, 2013, Imbruvica, 96 pages; https://www.accessdata.fda.gov/drugsatfda_docs/nda/2013/2055520rigls000ClinPharmR.pdf).
IMBRUVICA® (ibrutinib) capsules, for oral use, prescribing information, Revised Jan. 2017, 37 pages.
Advani, R. H. et al., "Bruton Tyrosine Kinase Inhibitor Ibrutinib (PCI-32765) Has Significant Activity in Patients With Relapsed/Refractory B-Cell Malignancies," Journal of Clinical Oncology, 31(1):88-84 (2012).
Alanine, A. et al., "Synthesis and SAR evaluation of 1,2,4-triazoles as A(2A) receptor antagonists," Bioorganic and Medicinal Chemistry Letters, 14(3):817-821 (2004).
Baens, N. P. et al., Synthesis of 2,5-substituted piperidines: Transposition of 1,4-substitution pattern for the analgesic drug R6582, Tetrahedron, 49(15):3193-3202 (1993).
Binnerts, M. E. et al., "Abstract C186: SNS-062 is a potent noncovalent BTK inhibotir with comparable activity against wild type BTK and BTK with an acquired resistance mutation," Abstracts: AACR-NCI-EORTC International Conference: Molecular Targets and Cancer Tharapeutics; Nov. 5-9, 2015, Boston, MA, 2 pages; doi:10.1158/1535-7163.
Brase, S. et al., "Organic azides: an exploding; diversity of a unique class of compounds," Angewandte Chemie (International Edition in English), 44(33):5188-5240 (2005).
Buggy, J. J. & Elias, L., "Bruton Tyrosine Kinase (BTK) and Its Role in B-cell Malignancy," International Reviews of Immunology, (31):119-132 (2012).
Byrd, J. C. et al., "Acalabrutinib (ACP-196) in Relapsed Chronic Lymphocytic Leukemia," N Engl J Med, 374(4):323-332 (2016).

Chabner, B. A. et al., "Chemotherapy of Neoplastic Diseases, Neoplastic Agents," in Goodman & Gilman's The Pharmacological Basis of Therapeutics, L. L. Brunton et al., Eds., 11th Ed., pp. 1315-1403 (2006).
Chong, P.Y. et al., "Multilevel selectivity in the mild and high-yielding chlorosilane-induced cleavage of carbamates to isocyanates," Journal of Organic Chemistry, 63:8515-8521 (1998).
Gao, W. et al., "Selective Antitumor Activity of Ibrutinib in EGFR-Mutant Non—Small Cell Lung Cancer Cells," JNCI J Natl Cancer Inst, 106(9) (2014); dju204 doi:10.1093/jnci/dju204, 4 pages.
Gong, P.K. et al., "Synthesis, monoamine transporter binding, properties, and functional monoamine; uptake activity of 3beta-[4-methylphenyl and 4-chlorophenyl]-2; beta-[5-(substituted phenyl)thiazol-2-yl]tropanes," Journal of Medicinal Chemistry, 50(15):3686-95 (2007).
Hartner, F.W. et al., "Methods for the synthesis of; 5,6,7,8-tetrahydro-1,8-naphthyridine fragments for alphaVbeta3 integrin; antagonists," Journal of Organic Chemistry, 69(25):872330 (2004).
Herman, S. E. M. et al., "Bruton tyrosine kinase represents a promising therapeutic target for treatment of chronic lymphocytic leukemia and is effectively targeted by PCI-32765," Blood, 117(23):9287-6296 (2011).
Huang, J. et al., "The synthesis of 5-substituted ring E analogs of ethyllycaconitine via the Suzuki-Miyaura cross-coupling reaction," Bioorganic and Medicinal Chemistry, 16(7):3816-24 (2008).
Kil, L. P. et al., "Bruton's tyrosine kinase mediated signaling enhances leukemogenesis in a mouse model for chronic lymphocytic leukemia," Am J Blood Res, 3(1):71-83 (2013).
Lei, X. et al., "The Akp-Btk value method and the results for the retrieval of the parameters of the Earth's free core nutation," Acta Seismologica Sinica, 13(3):342-350 (2000).
Melgar-Fernandez, R. et al., Synthesis of novel derivatives of (1S,4S)-2,5-Diazabicyclo[2.2.1]heptane and their evaluation as potential ligands in asymmetric catalysis, European Journal of Organic Chemistry, 4:655-672 (2008).
Mehrotra, M.M. et al., "Spirocyclic nonpeptide glycoprotein IIb-IIIa antagonists. Part 3: synthesis and SAR of potent and specific 2,8-diazaspiro[4.5]decanes," Bioorganic and Medicinal Chemistry Letters, 12(7):1103-1107 (2002).
Nakamura, H. et al., "Synthesis of heterocyclic allenes via; palladium-catalyzed hydridetransfer reaction of propargylic amines," Journal of Organic Chemistry, 70(6):23572360 (2005).
Penso, M. et al., "A straightforward synthesis of enantiopure 2,6-disubstituted morpholines by a regioselective o-protection/activation protocol," Synlett, 16:2451-2454 (2008).
Pflum, D.A. et al., "Asymmetric synthesis of cetirizine dihydrochloride," Tetrahedron Letters, 43:923-926 (2002).
Poupaert, J. H., Drug Design: Basic Principles and Applications,' in Encyclopedia of Pharmaceutical Technology, J. Swarbrick, Ed., 3rd Ed., pp. 1362-1369 (2007).
Sainsbury, M., "Heterocyclic Chemistry," E. W. Abel et al., Eds., pp. 97-114 (2001).
Saunders, J. et al., "Novel quinuclidine-based ligands for the muscarinic cholinergic receptor," Journal of Medicinal Chemistry, 33(4):1128-38 (1990).
Scriven, E. F. V. & Turnbull, K., "Azides: Their preparation and synthetic uses," Chemical Reviews, 88(2):298-368 (1988).
Shafir, a. & Buchwald, S. L., "Highly selective room-temperature copper-catalyzed CN coupling reactions," Journal of the American Chemical Society, 128(27):8742-3 (2006).
Tai, Y. -T. et al., "Bruton tyrosine kinase inhibition is a novel therapeutic strategy targeting tumor in the bone marrow microenvironment in multiple myeloma," Blood, 120(9):1877-1887 (2012).
Woyach, J. A. et al., "Bruton's tyrosine kinase (BTK) function is important to the development and expansion of chronic lymphocytic leukemia (CLL)," Blood, 123(8):12071213 (2014).
Woyach, J. A. et al., "Resistance Mechanisms for the Bruton's Tyrosine Kinase Inhibitor Ibrutinib," N Engl J Med, 370(24):2286-2294 (2014).

(56) References Cited

OTHER PUBLICATIONS

Wyatt, P.G. et al., "Identification of potent and selective oxytocin antagonists. Part; 1: indole and benzofuran derivatives," Bioorganic and Medicinal Chemistry Letters, 12(10):1399-404 (2002).

* cited by examiner

PYRIMIDINYL TYROSINE KINASE INHIBITORS

CROSS REFERENCE TO RELATED APPLICATIONS

The present application is a continuation of U.S. application Ser. No. 15/196,389, filed on Jun. 29, 2016 (now allowed), which is a continuation of U.S. application Ser. No. 14/406,315, filed Dec. 8, 2014 (now U.S. Pat. No. 9,394,277), which is a U.S. National Phase application, filed under 35 U.S.C. § 371, of International Application No. PCT/US2013/044800, filed Jun. 7, 2013, which claims priority to U.S. provisional application Ser. No. 61/657,360, filed Jun. 8, 2012, the entire contents of each of which are hereby incorporated herein by reference.

BACKGROUND OF THE INVENTION

The Tec kinases are non-receptor tyrosine kinases including: Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk), Lck (lymphocyte-specific protein tyrosine kinase), and Bmx (bone-marrow tyrosine kinase gene on chromosome X; also known as Etk)). These kinases are primarily expressed in haematopoietic cells, although expression of Bmx and Tec has been detected in endothelial and liver cells. Tec kinases (Itk, Rlk and Tec) are expressed in T cells and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors for Tec kinases such as Btk. The present invention fulfills these and other needs.

SUMMARY OF THE INVENTION

In certain embodiments, the present invention provides a compound of formula I:

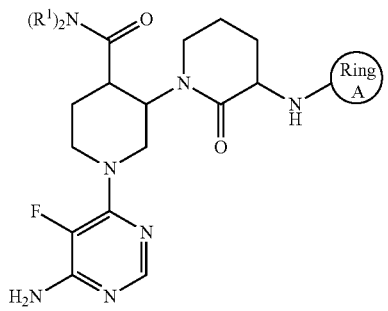

or a pharmaceutically acceptable salt thereof, wherein $R^1$ and Ring A are as defined and described herein. Such compounds are inhibitors of the Tec kinase family, including Btk. Accordingly, provided compounds can be used in a variety of methods including in vitro screening and activity assays as well as in vivo pre-clinical, clinical, and therapeutic settings, as described in detail herein.

In certain embodiments, the present invention provides pharmaceutical formulations comprising provided compounds.

In certain embodiments, the present invention provides a method of decreasing enzymatic activity of Btk. In some embodiments, such methods include contacting Btk with an effective amount of a Btk inhibitor.

In certain embodiments, the present invention provides a method of treating a disorder responsive to Btk inhibition in a subject in need thereof. Such disorders and methods are described in detail herein.

DETAILED DESCRIPTION OF CERTAIN EMBODIMENTS

In certain embodiments, the present invention provides a compound of formula I:

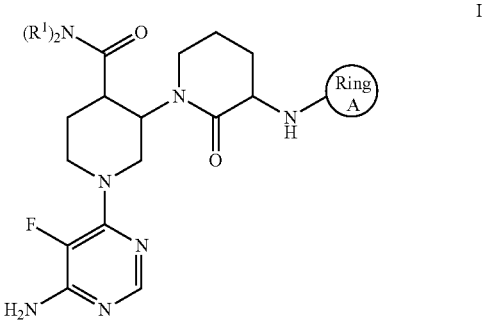

or a pharmaceutically acceptable salt thereof;
wherein:
  each $R^1$ is independently hydrogen, an optionally substituted $C_{1-6}$ aliphatic group, an optionally substituted 3-7 membered monocyclic heterocyclic group, or an optionally substituted heterocyclylalkyl group having 3-7 carbon atoms and 1-3 heteroatoms independently selected from nitrogen, oxygen, or sulfur;
  or two $R^1$ groups are taken together with their intervening atoms to form an optionally substituted 3-7 membered saturated or partially unsaturated monocyclic heterocyclic ring having 1-2 heteroatoms independently selected from nitrogen, oxygen, or sulfur;
  wherein optionally substituted groups may be substituted with halogen, —$NO_2$, —CN, —OR, —SR, —$N(R)_2$, —C(O)R, —$CO_2R$, —N(R)C(O)OR, —C(O)N(R)_2, —OC(O)R, —N(R)C(O)R, —S(O)R, —$S(O)_2R$, or —$S(O)_2N(R)_2$;
  each R is independently hydrogen or $C_{1-6}$ aliphatic;
    or two R groups attached to the same nitrogen are taken together with their intervening atoms to form an optionally substituted 3-7 membered saturated or partially unsaturated monocyclic heterocyclic ring having 1-2 heteroatoms, in which any second heteroatom is independently selected from nitrogen, oxygen, or sulfur;

Ring A is

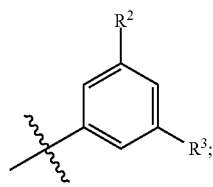

R$^2$ is —Cl or —F; and
R$^3$ is —CF$_3$, —OCF$_3$, or —F.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule.

As used herein, the terms "heterocycle," "heterocyclyl," and "heterocyclic ring" are used interchangeably and refer to a stable 3- to 7-membered monocyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). The term "heterocyclylalkyl" refers to an alkyl group substituted by a heterocyclyl, wherein the alkyl and heterocyclyl portions independently are optionally substituted.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Compounds

As described above, in certain embodiments the present invention provides a compound of formula I:

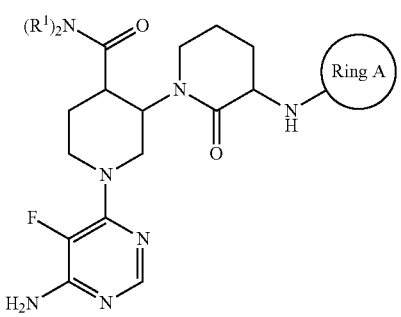

of a pharmaceutically acceptable salt thereof, wherein $R^1$ and Ring A are as defined and described herein.

Compounds of formula I have unexpectedly been found to exhibit advantageous properties over known inhibitors of Btk. In certain embodiments, compounds of formula I have increased potency. Without wishing to be bound by any particular theory, it is believed that compounds disclosed herein possess improved potency as Btk inhibitors, an improved off-target profile as measured by hERG inhibition or PXR induction assays, or a combination thereof. Experimental data showing such advantageous properties is provided in the ensuing Examples.

In some embodiments, both $R^1$ are hydrogen. In some embodiments, each $R^1$ is independently $C_{1-6}$ aliphatic. In some embodiments, each $R^1$ is independently $C_{1-5}$ aliphatic. In some embodiments, each $R^1$ is independently $C_{1-4}$ aliphatic. In some embodiments, each $R^1$ is independently $C_{1-3}$ aliphatic. In some embodiments, each $R^1$ is independently $C_{1-2}$ aliphatic. In some embodiments, both $R^1$ are methyl.

In some embodiments, each $R^1$ is independently hydrogen or $C_{1-6}$ aliphatic. In some embodiments, each $R^1$ is independently hydrogen or $C_{1-5}$ aliphatic. In some embodiments, each $R^1$ is independently hydrogen or $C_{1-4}$ aliphatic. In some embodiments, each $R^1$ is independently hydrogen or $C_{1-3}$ aliphatic. In some embodiments, each $R^1$ is independently hydrogen or $C_{1-2}$ aliphatic. In some embodiments, each $R^1$ is independently hydrogen or methyl.

In some embodiments, one $R^1$ is hydrogen or and the other $R^1$ is $C_{1-6}$ aliphatic. In some embodiments, one $R^1$ is hydrogen and the other $R^1$ is methyl. In some embodiments, one $R^1$ is hydrogen and the other $R^1$ is ethyl. In some embodiments, one $R^1$ is hydrogen and the other $R^1$ is $C_{1-6}$ (cycloalkyl)alkyl. In some embodiments, one $R^1$ is hydrogen and the other $R^1$ is $C_{1-6}$ (cycloalkyl).

In some embodiments, one $R^1$ is hydrogen and the other $R^1$ is $C_{1-6}$ aliphatic optionally substituted with —OR, wherein R is hydrogen or $C_{1-6}$ aliphatic.

In some embodiments, one $R^1$ is hydrogen and the other $R^1$ is a heterocyclylalkyl group having 3-7 carbon atoms and 1-3 heteroatoms independently selected from nitrogen, oxygen, or sulfur. In some embodiments, one $R^1$ is hydrogen and the other $R^1$ is an optionally substituted 3-7 membered monocyclic heterocycle.

In some embodiments, two $R^1$ groups are taken together with their intervening atoms to form an optionally substituted 3-5 membered saturated or partially unsaturated monocyclic heterocyclic ring having 1-2 heteroatoms independently selected from nitrogen, oxygen, or sulfur. In some embodiments, two $R^1$ groups are taken together with their intervening atoms to form an optionally substituted piperazine ring.

As described above, Ring A is

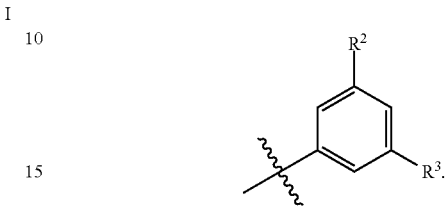

In certain embodiments, $R^2$ is —Cl. In other embodiments, $R^2$ is —F. In some embodiments, $R^3$ is —CF$_3$. In some embodiments, $R^3$ is —OCF$_3$. In some embodiments, $R^3$ is —F.

In certain embodiments, Ring A is selected from the group consisting of:

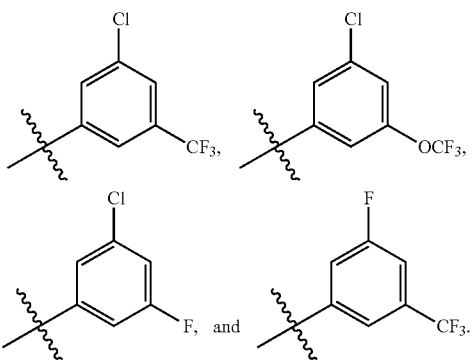

In some embodiments, in compounds described herein there is a trans stereochemical relationship between the piperidine substituent bearing the carboxamide group and the piperidine substituent bearing the lactam group.

In some embodiments, the present invention provides a compound of formula II-a:

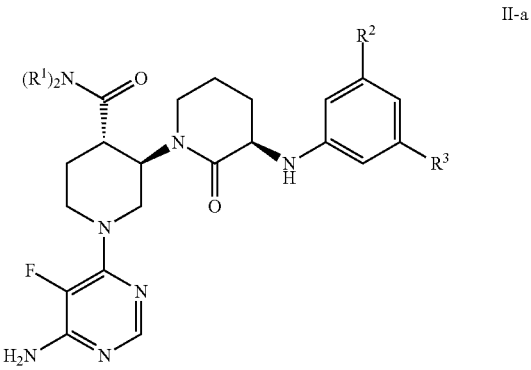

or a pharmaceutically acceptable salt thereof, wherein each of $R^1$, $R^2$, and $R^3$ is as defined above and described in classes and subclasses herein.

In some embodiments, the present invention provides a compound of formula II-b:

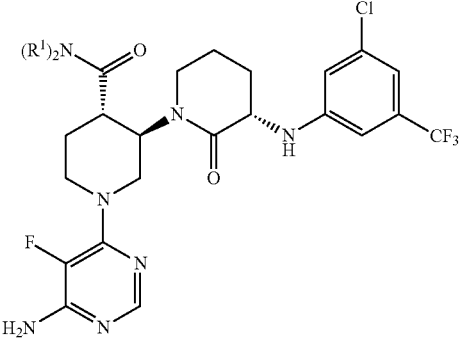

II-b or a pharmaceutically acceptable salt thereof, wherein each of $R^1$, $R^2$, and $R^3$ is as defined above and described in classes and subclasses herein.

In some embodiments, the present invention provides a compound of formula III:

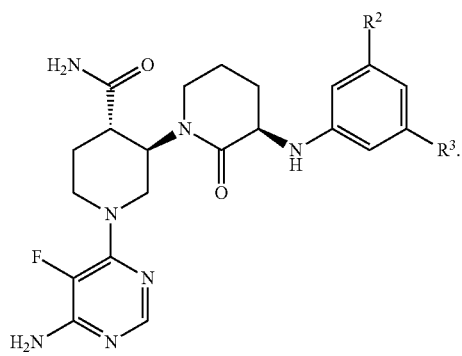

III or a pharmaceutically acceptable salt thereof, wherein each of $R^2$ and $R^3$ is as defined above and described in classes and subclasses herein.

In some embodiments, the present invention provides a compound of formula IV:

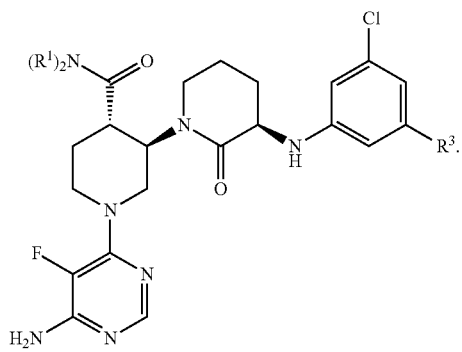

IV or a pharmaceutically acceptable salt thereof, wherein each of R and $R^3$ is as defined above and described in classes and subclasses herein. In some embodiments, both $R^1$ are hydrogen. In some embodiments, one $R^1$ is hydrogen and the other $R^1$ is methyl.

In some embodiments, a provided compound is a compound depicted in Table 1, below, or a pharmaceutically acceptable salt thereof.

TABLE 1

Selected compounds of formula I.

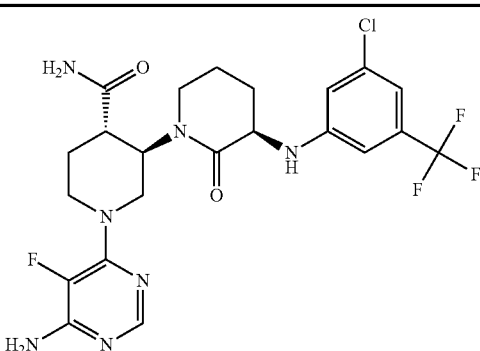

I-1

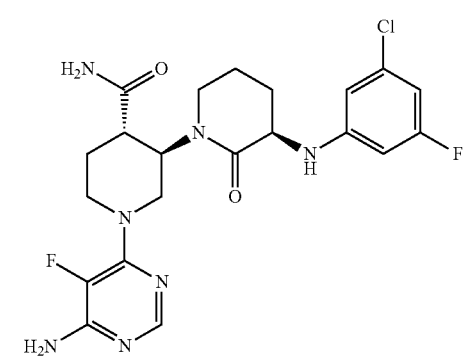

I-2

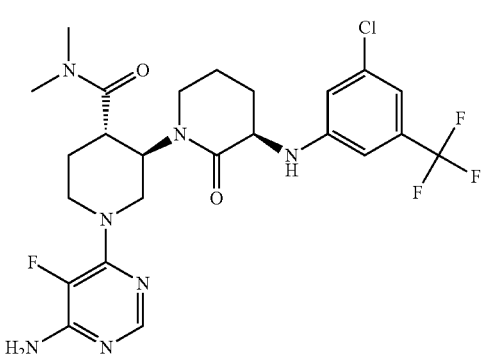

I-3

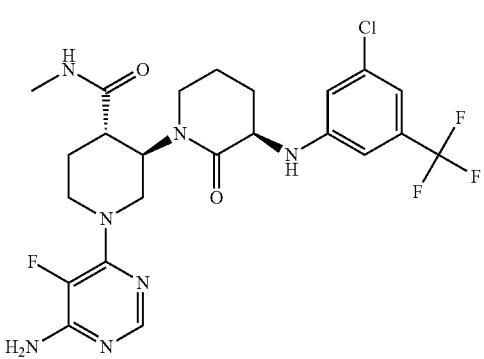 [SMILES: CNC(=O)[C@H]1CCN(c2ncnc(N)c2F)C[C@@H]1N1CCC[C@@H](Nc2cc(Cl)cc(C(F)(F)F)c2)C1=O]

I-4

TABLE 1-continued

Selected compounds of formula I.

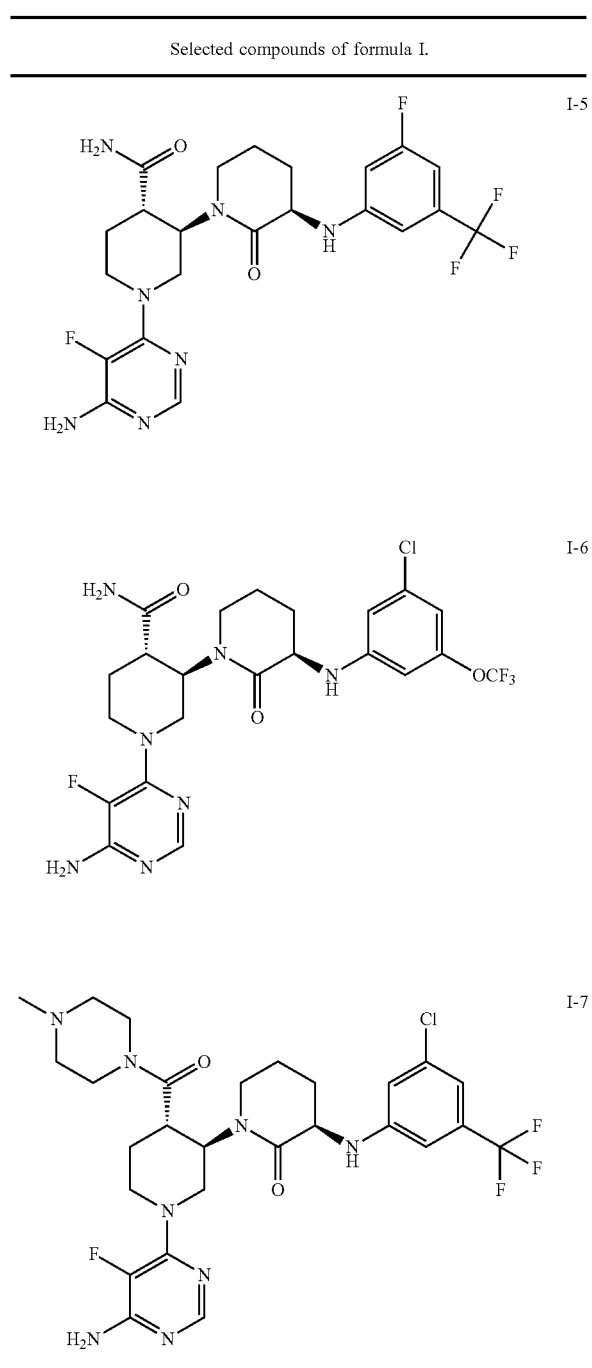

Compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

Compounds of formula I may be generally prepared according to Scheme 1.

Scheme 1

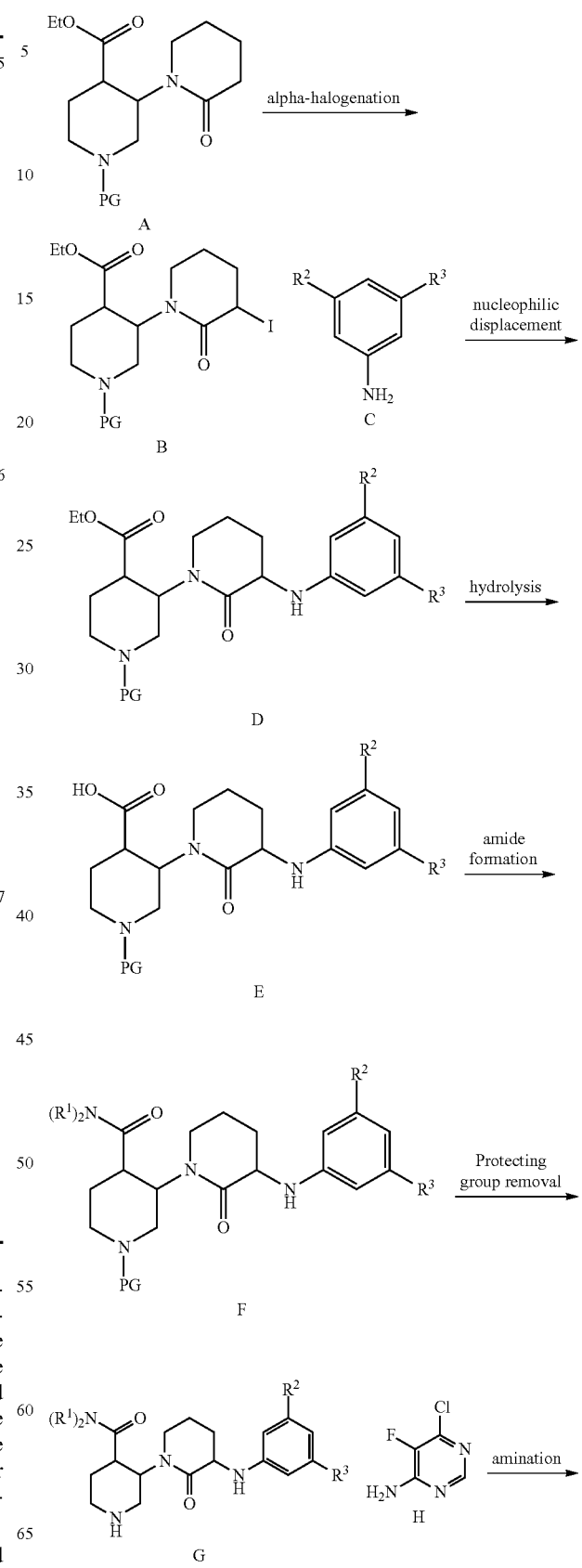

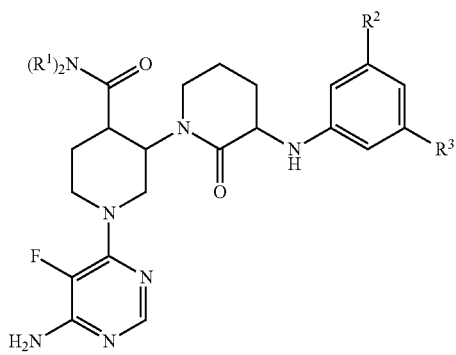
Wyatt, P.G. et al., "Identification of potent and selective oxytocin
Compounds of formula I may also be generally prepared according to Schemes 2, 3, 3a, 4, 4a, 5, or 5a.
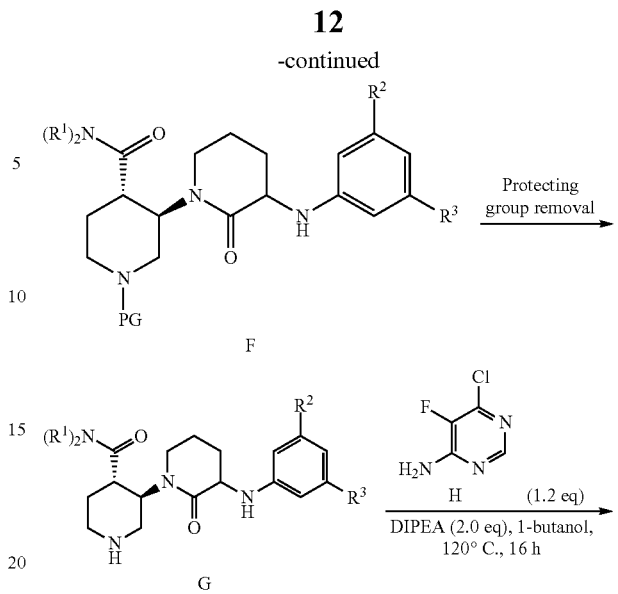
Scheme 2
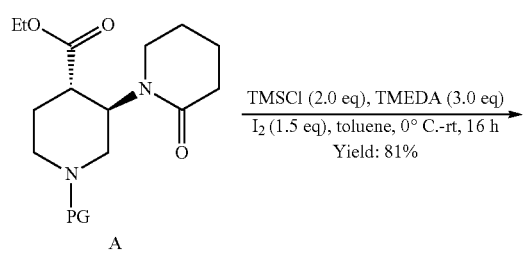
Scheme 3

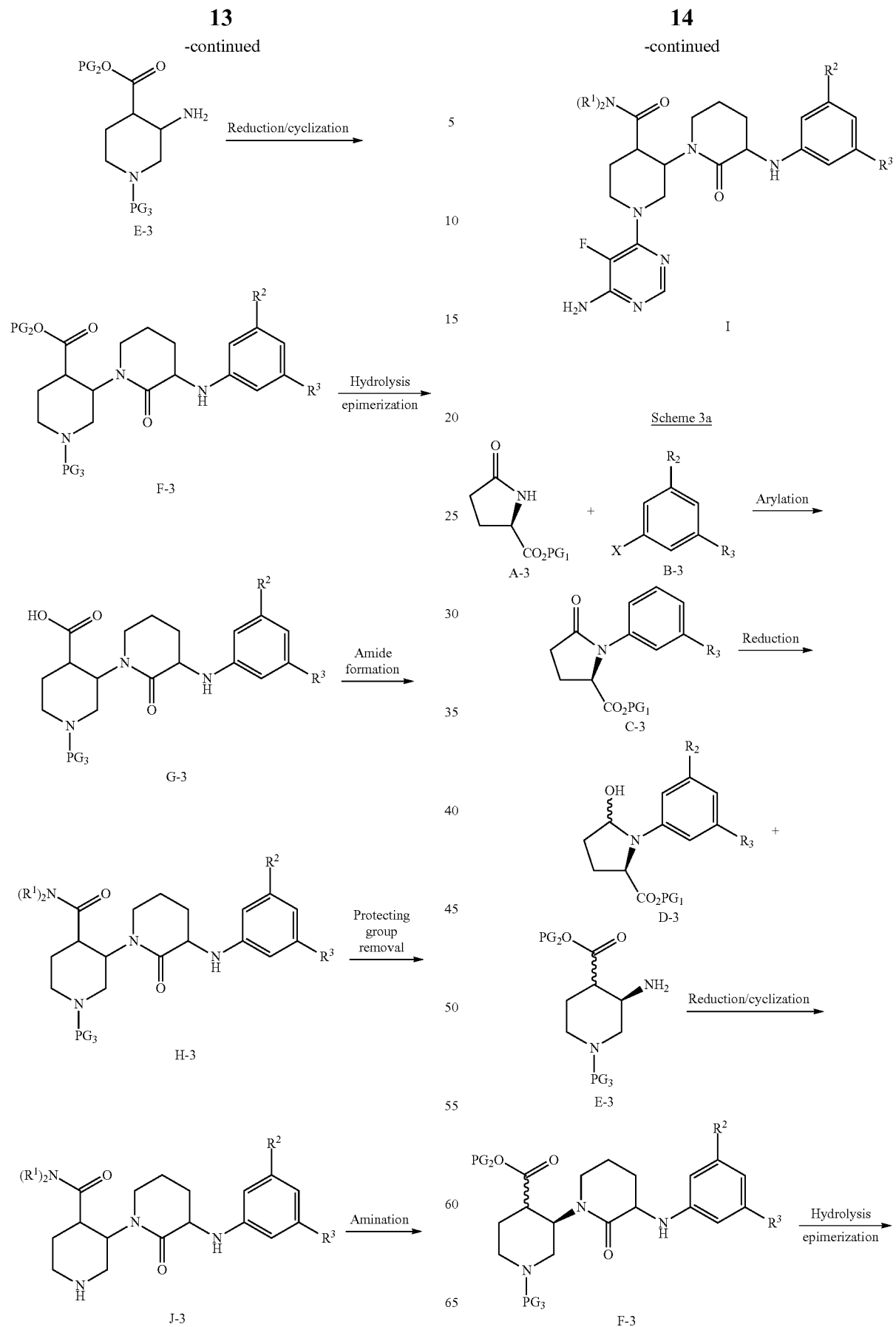

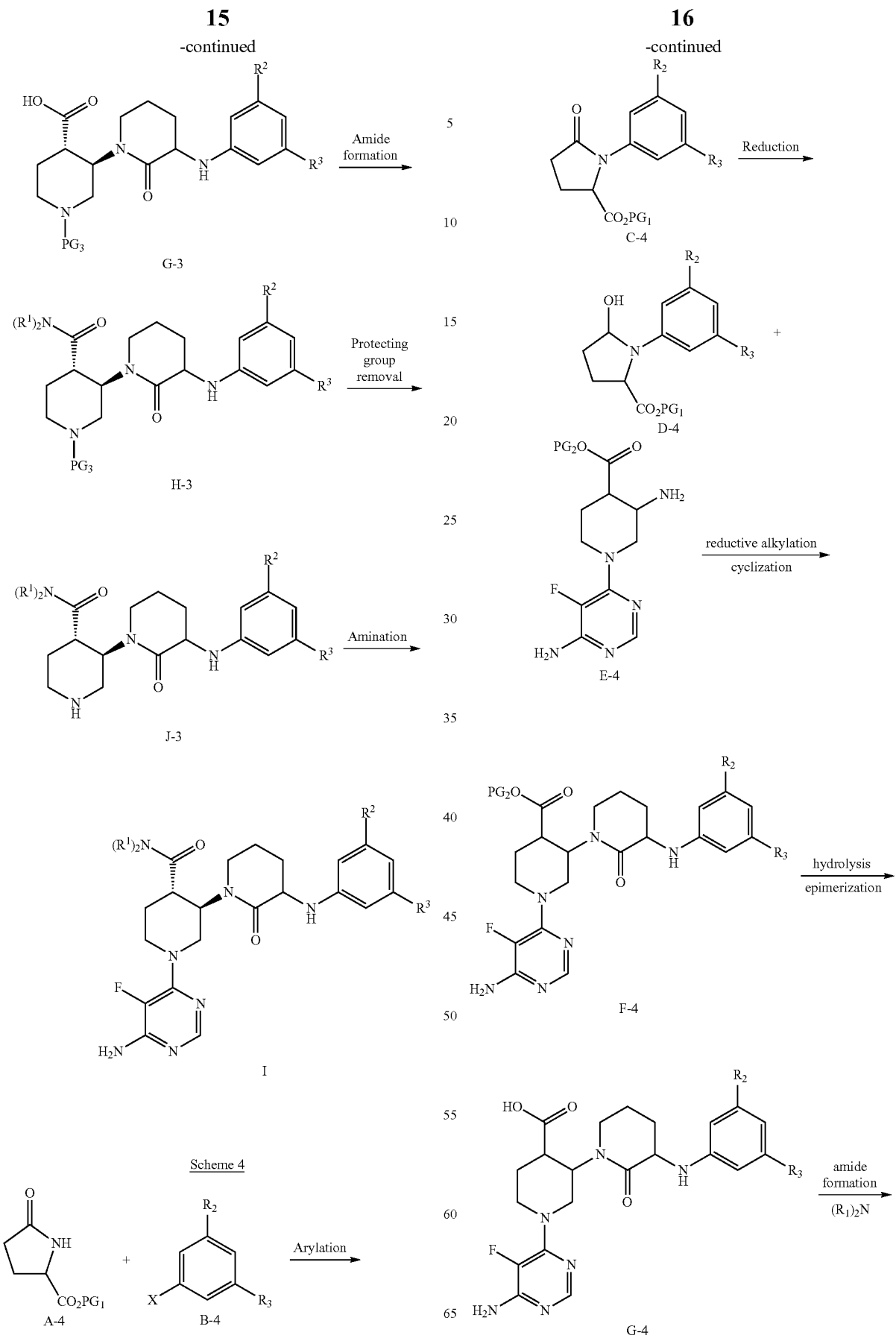

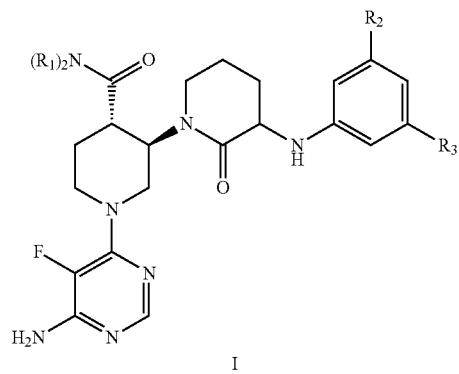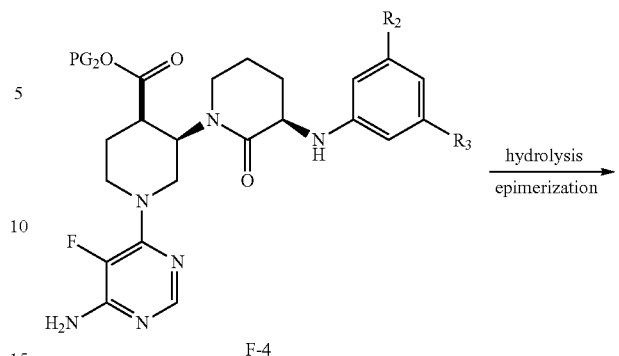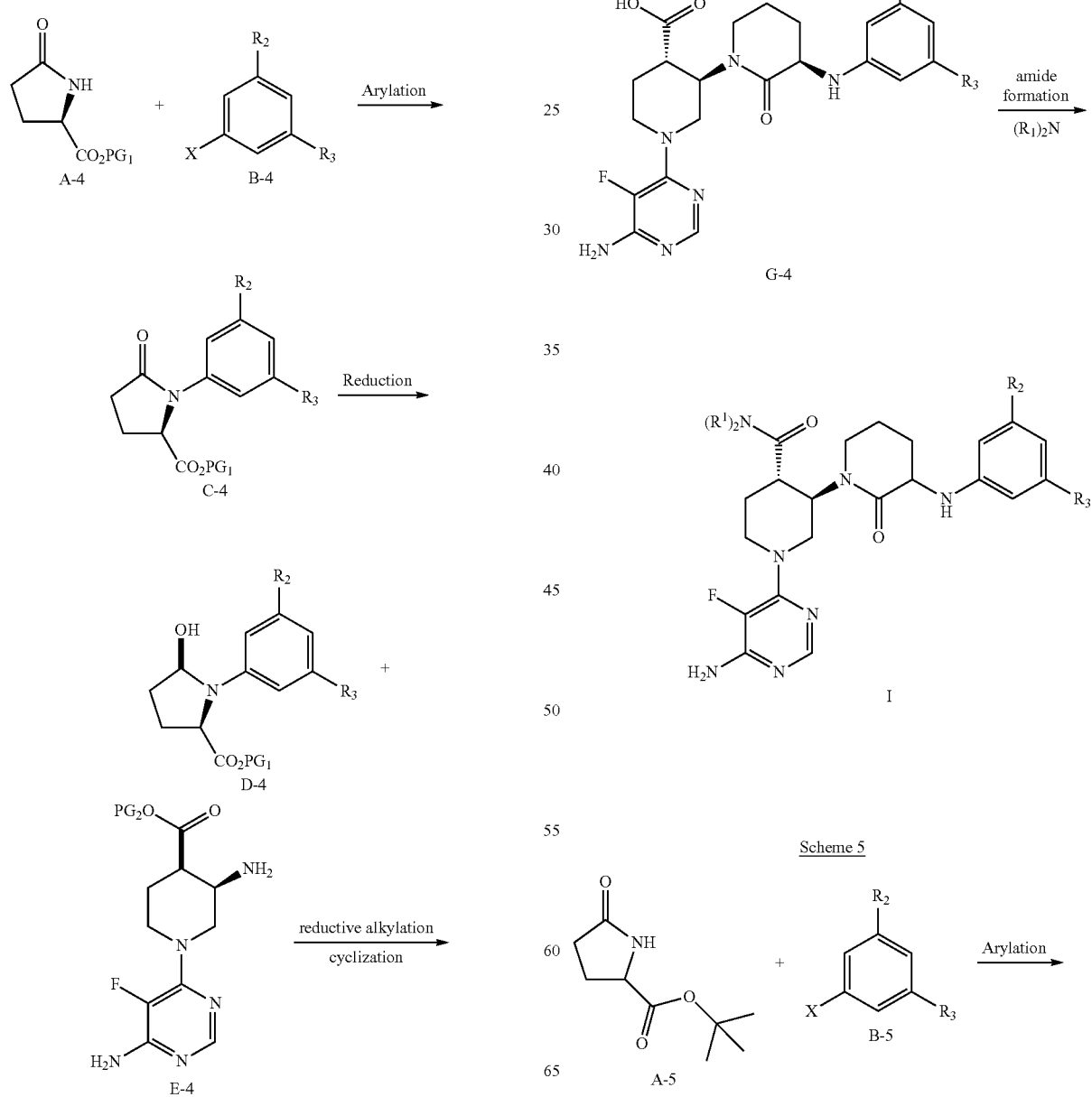

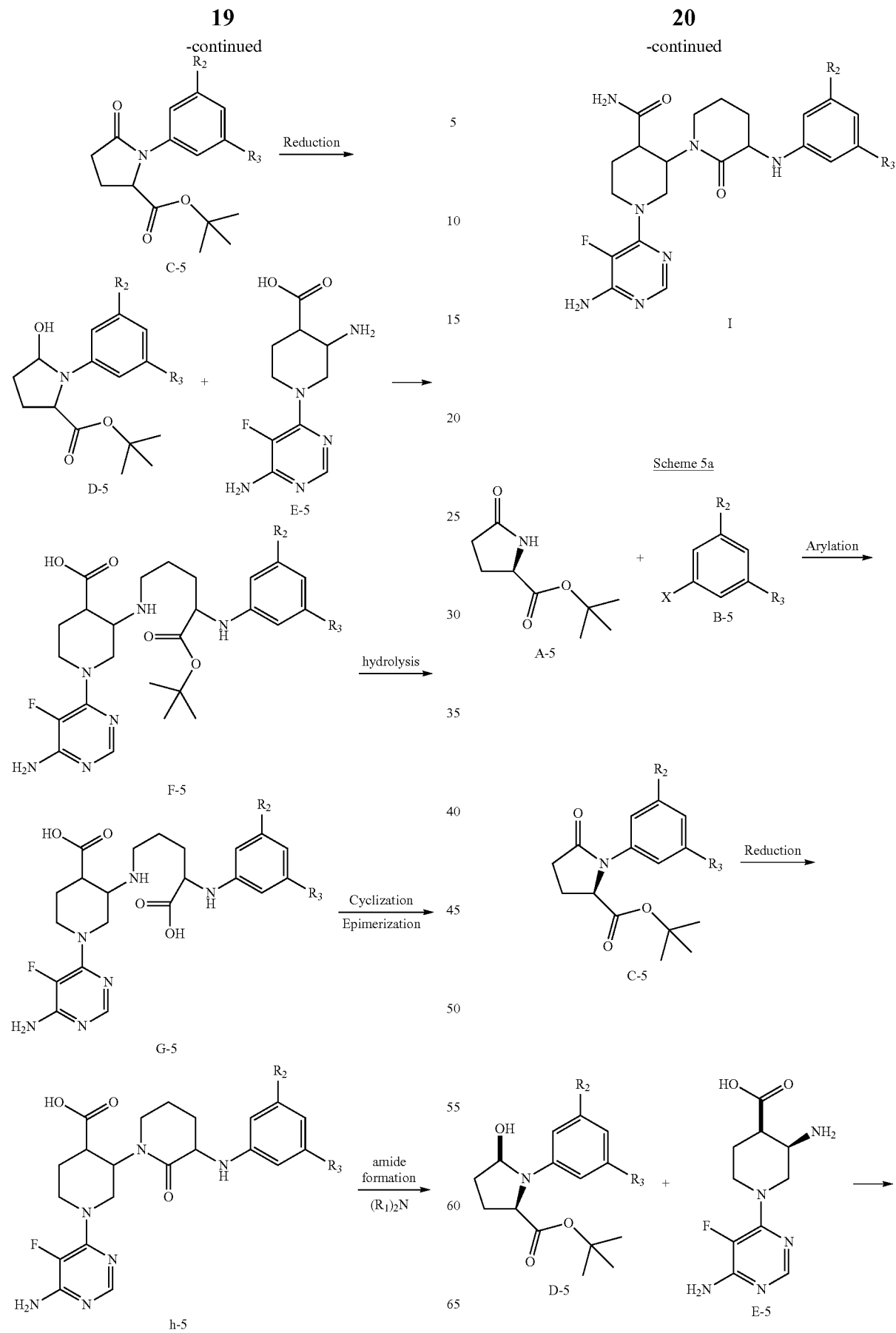

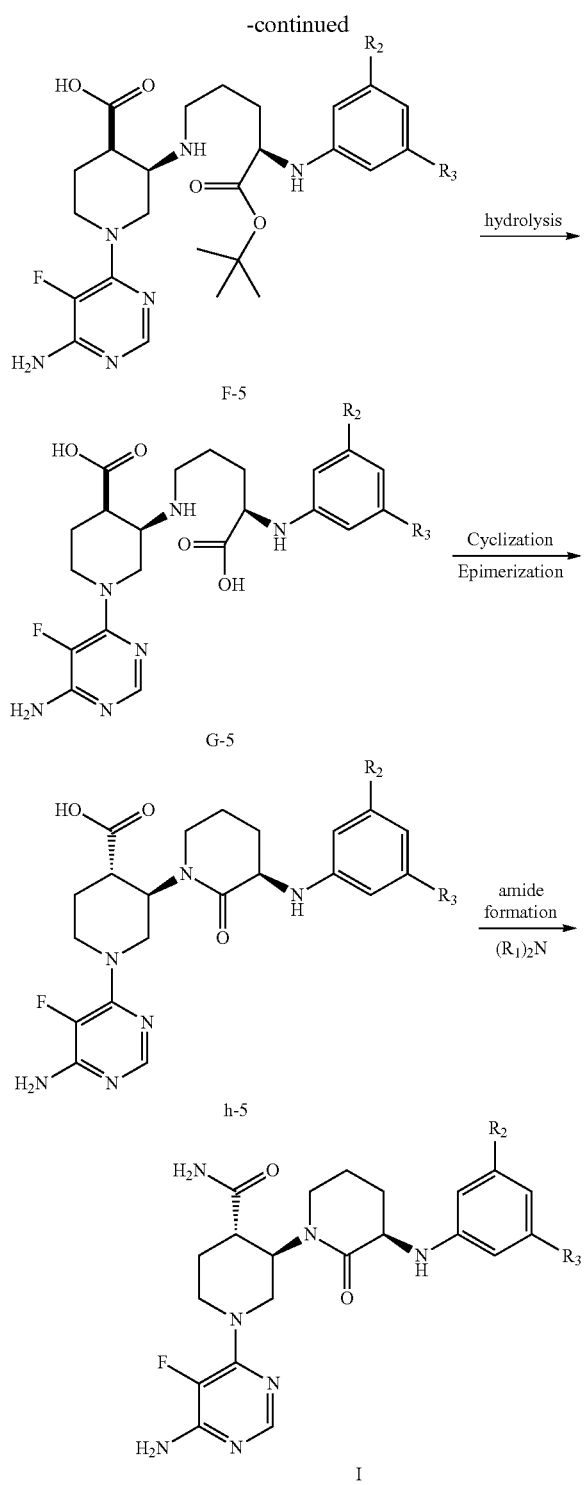

The PG, PG$_1$, PG$_2$, and PG$_3$ groups of compounds in Schemes 1 through 5a are each independently a suitable protecting group. Such ester and amine protecting groups are known in the art and are described in detail in *Protecting Groups in Organic Synthesis*, T. W. Greene and P. G. M. Wuts, 3$^{rd}$ edition, John Wiley & Sons, 1999, the entirety of which is incorporated herein by reference. In some embodiments, a protecting group is a Boc group.

In certain embodiments, each of the synthetic steps in Schemes 1 through 5a may be performed sequentially with isolation of each intermediate performed after each step. Alternatively, each of the steps as depicted in Schemes 1, 2, 3, and 4 above, may be performed in a manner whereby no isolation of one or more intermediates is performed.

In certain embodiments, all the steps of the aforementioned synthesis may be performed to prepare the desired final product. In other embodiments, two, three, four, five, or more sequential steps may be performed to prepare an intermediate or the desired final product.

Uses, Formulation and Administration

In certain embodiments, compounds of the present invention are for use in medicine. In some embodiments, the present invention provides method of decreasing enzymatic activity of a kinase in the Tec kinase family (e.g., Tec, Btk, Itk, Txk, Lck, and Bmx). In some embodiments, such methods include contacting a kinase of the Tec kinase family with an effective amount of a Tec kinase family inhibitor. Therefore, the present invention further provides methods of inhibiting Tec kinase family enzymatic activity by contacting a Tec kinase family member with a Tec kinase family inhibitor of the present invention. As used herein, the term "Tec kinase family member" refers to any non-receptor tyrosine kinase in the Tec kinase family. In some embodiments, Tec kinase family members are Tec, Btk, Itk, Txk, Lck, and Bmx.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

Btk enzymatic activity, as used herein, refers to Btk kinase enzymatic activity. For example, where Btk enzymatic activity is decreased, PIP3 binding and/or phosphorylation of PLCγ is decreased. In some embodiments, the half maximal inhibitory concentration (IC$_{50}$) of the Btk inhibitor against Btk is less than 1 µM. In some embodiments, the IC$_{50}$ of the Btk inhibitor against Btk is less than 500 nM. In some embodiments, the IC$_{50}$ of the Btk inhibitor against Btk is less than 100 nM. In some embodiments, the IC$_{50}$ of the Btk inhibitor against Btk is less than 10 nM. In some embodiments, the IC$_{50}$ of the Btk inhibitor against Btk is less than 1 nM. In some embodiments, the IC$_{50}$ of the Btk inhibitor against Btk is from 0.1 nM to 10 µM. In some embodiments, the IC$_{50}$ of the Btk inhibitor against Btk is from 0.1 nM to 1 µM. In some embodiments, the IC$_{50}$ of the Btk inhibitor against Btk is from 0.1 nM to 100 nM. In some embodiments, the IC$_{50}$ of the Btk inhibitor against Btk is from 0.1 nM to 10 nM.

In some embodiments, inhibitors of such Tec kinases are useful for the treatment of diseases and disorders that may be alleviated by inhibiting (i.e., decreasing) enzymatic activity of one or more Tec kinases. The compounds of the invention are effective inhibitors of Tec family kinases and would thus be useful in treating diseases associated with the activity of one or more of the Tec family kinases. The term "diseases" means diseases, syndromes, or disease symptoms. Thus, the present invention provides methods of treating autoimmune disorders, inflammatory disorders, and cancers in a subject in need thereof. Such methods include administering to the subject a therapeutically effective amount of an inhibitor of Tec, Btk, Itk, Txk, Lck, and/or Bmx kinase.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), hemolytic anemia, autoimmune hepatitis, bullous pemphigoid (BP), Coeliac disease, dermatomyositis, diabetes mellitus type 1, Good Pasture's syndrome, Graves' disease, Guillain-Barré syndrome (GBS), Hashimoto's disease, idiopathic thrombocytopenic purpura, lupus or systemic lupus erythematosus (SLE), mixed connective tissue disease, multiple sclerosis, myasthenia gravis, pemphigus vulgaris, hemophilia with inhibitors, pernicious anaemia, polymyositis, primary biliary cirrhosis, Sjögren's syndrome, temporal arteritis, and Wegener's granulomatosis. The term "inflammatory disorders" includes diseases or disorders involving acute or chronic inflammation such as allergies, asthma (e.g., allergic asthma), atopic dermatitis, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection (including transplant patients with a positive cross-match) and vasculitis. In certain embodiments, the present invention provides methods of treating disease, disorders, or conditions that approved for treatment with rituximab (a monoclonal antibody against $CD_2O$), including non-Hodgkin's lymphoma (NHL), chronic lymphocytic leukemia (CLL), RA, Wegener's granulomatosis (WG), and microscopic polyangiitis (MPA). In some embodiments, the present invention provides a method of treating rheumatoid arthritis (RA), SLE, or atopic dermatitis using compounds disclosed herein.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

The term "subject," as used herein, refers to a mammal to whom a pharmaceutical composition is administered. Exemplary subjects include humans, as well as veterinary and laboratory animals such as horses, pigs, cattle, dogs, cats, rabbits, rats, mice, and aquatic mammals.

Selected Indications and B Cell Inhibition

As described above, provided compounds are useful for the treatment of disease, including RA and SLE. As described in more detail below, these diseases are affiliated with B cells. Thus, the present disclosure encompasses the recognition that provided compounds are useful as therapeutics for these and other indications.

Dysregulation of the immune system is central to the pathogenesis (Panayi G S, et al. Rheum Dis Clin North Am 2001; 27:317-334) of RA. While most of the infiltrating leukocytes in the synovium are T lymphocytes (primarily activated CD4+ T cells) and cells of monocyte/macrophage origin (which release pro-inflammatory cytokines such as IL-1, TNF-alpha and IL-6 and proteolytic enzymes including collagenases and metalloproteinases), B-cells and plasma cells are also found in the synovial fluid (Zhang Z, Bridges S L. Rheum Dis Clin North Am 2001; 27:335-353). A clear role for B cells and their associated effector functions in RA have been demonstrated by the efficacy of rituximab, a selective B cell depleting therapeutic, which is approved for treatment of RA (Cohen S B, et al.; REFLEX Trial Group. Arthritis Rheum. 2006 September; 54(9):2793-806).

Although the etiology of SLE is not fully understood, pathogenic autoantibodies and deposition of immune complexes are felt to be critical to the development of widespread tissue damage (Klippel J H, et al. Primer on the rheumatic diseases. Atlanta: Arthritis Foundation; 2001). Autoantibody and immune-complex mediated activation can be studied by measuring inhibition of macrophage activation by macrophages stimulated through Fc receptors (see exemplification—FcγR activation of primary human macrophages). Loss of tolerance to self-antigens ultimately lead to the stimulation of B cells to produce auto-antibodies often directed against nuclear or cytoplasmic components. Antibodies against nuclear components (anti-nuclear antibodies [ANA]) target nuclear antigens including DNA (typically double-stranded DNA [dsDNA]), RNA, histones and small nuclear ribonucleoproteins. These antibodies combine with self-antigens forming immune complexes which deposit in tissues, incite inflammatory reactions and lead to tissue injury. In addition to their roles in pathogenic autoantibody production, B cells also function as antigen-presenting cells (APCs) to T-cells thus playing a role in the initiation of an antigen-specific response. Given the central role of the humoral arm of the immune system in the pathogenesis of SLE, B cells or the B-cell pathway represent desirable therapeutic targets. Belimumab, a monoclonal antibody recently approved for SLE, blocks the binding BAFF to its receptors that are expressed B cells. These receptors serve to activate and potentiate the survival of B cells consistent with a reduction of circulating B cells observed following treatment with belimumab. See also Chan O T, et al. Immunol Rev. 1999b; 169:107-121; Navarra S V, et al. Lancet. 2011 Feb. 26; 377(9767):721-31; Furie R, et al. Arthritis Rheum. 2011 December; 63(12):3918-30. The role of B cells and myeloid lineage cells in autoimmune diseases such as SLE is further supported by a recent publication which describes efficacy in a preclinical SLE animal model when mice are treated with a small molecule irreversible Btk inhibitor (Honigberg, L. A. PNAS. 2010; 107: 13075).

Combinations

In certain embodiments, a compound of the present invention is administered in combination with another agent. In some embodiments, a compound of the present invention is useful for treating RA and is administered in combination with a disease-modifying antirheumatic drugs (DMARD), including without limitation: methotrexate, abatacept, azathioprine, certolizumab, chloroquine and hydroxychloroquine, cyclosporin, D-penicillamine, adalimumab, etanercept, golimumab, gold salts (including auranofin and sodium aurothiomalate), infliximab, leflunomide, minocycline, rituximab, sulfasalazine, tocilizumab, or combinations thereof. In some embodiments, a compound of the present invention is administered in combination with a NSAID or corticosteroid. In some embodiments, a compound of the present invention is useful for treating SLE and is administered in combination with an agent for the treatment of SLE, including without limitation: corticosteroids, antimalarials, belimumab, mycophenolate mofetil (MMF) or mycophenolate sodium, azathioprine, or combinations thereof. In some embodiments, a compound of the present invention is useful for treating atopic dermatitis and is administered in combination with a topical agent for the treatment of atopic dermatitis, including without limitation:

topical steroids, tacrolimus, methotrexate, mometasone furoate (MMF), azathioprine, retinoids, or combinations thereof.

Assays

To develop useful Tec kinase family inhibitors, candidate inhibitors capable of decreasing Tec kinase family enzymatic activity may be identified in vitro. The activity of the inhibitor compounds can be assayed utilizing methods known in the art and/or those methods presented herein.

Compounds that decrease Tec kinase family members' enzymatic activity may be identified and tested using a biologically active Tec kinase family member, either recombinant or naturally occurring. Tec kinases can be found in native cells, isolated in vitro, or co-expressed or expressed in a cell. Measuring the reduction in the Tec kinase family member enzymatic activity in the presence of an inhibitor relative to the activity in the absence of the inhibitor may be performed using a variety of methods known in the art, such as the POLYGAT-LS assays described below in the Examples. Other methods for assaying the activity of Btk and other Tec kinases are known in the art. The selection of appropriate assay methods is well within the capabilities of those of skill in the art.

Once compounds are identified that are capable of reducing Tec kinase family members' enzymatic activity, the compounds may be further tested for their ability to selectively inhibit a Tec kinase family member relative to other enzymes.

Compounds may be further tested in cell models or animal models for their ability to cause a detectable changes in phenotype related to a Tec kinase family member activity. In addition to cell cultures, animal models may be used to test Tec kinase family member inhibitors for their ability to treat autoimmune disorders, inflammatory disorders, or cancer in an animal model.

Pharmaceutical Compositions

In another aspect, the present invention provides pharmaceutical compositions comprising a compound of formula I or a compound of formula I in combination with a pharmaceutically acceptable excipient (e.g., carrier).

The pharmaceutical compositions include optical isomers, diastereomers, or pharmaceutically acceptable salts of the inhibitors disclosed herein. The compound of formula I included in the pharmaceutical composition may be covalently attached to a carrier moiety, as described above. Alternatively, the compound of formula I included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be co-administered to the subject. Co-administration is meant to include simultaneous or sequential administration of the compounds individually or in combination (more than one compound). The preparations can also be combined, when desired, with other active substances (e.g. to reduce metabolic degradation).

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to Btk inhibition); presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of decreasing kinase enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above. In certain embodiments, the administered dose is in the range of about 10 mg to about 1000 mg per day, either once, twice, or more than twice daily.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

Synthetic of (3'R,4'S)-1'-tert-butyl 4'-ethyl 2-oxo-[1,3'-bipiperidine]-1',4'-dicarboxylate

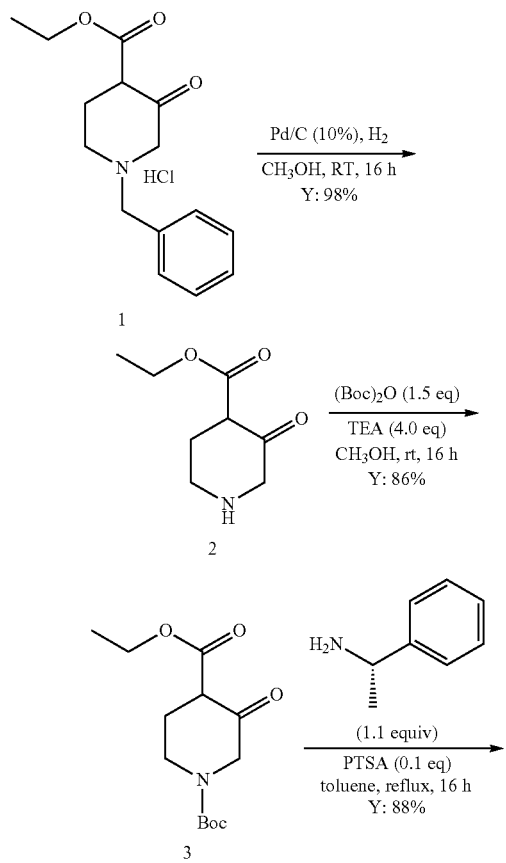

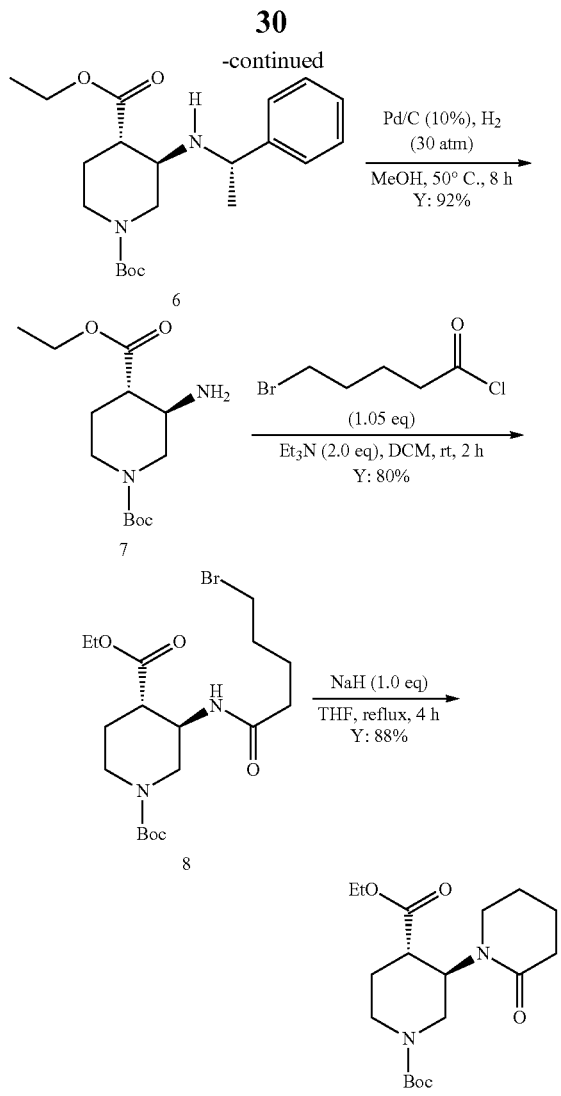

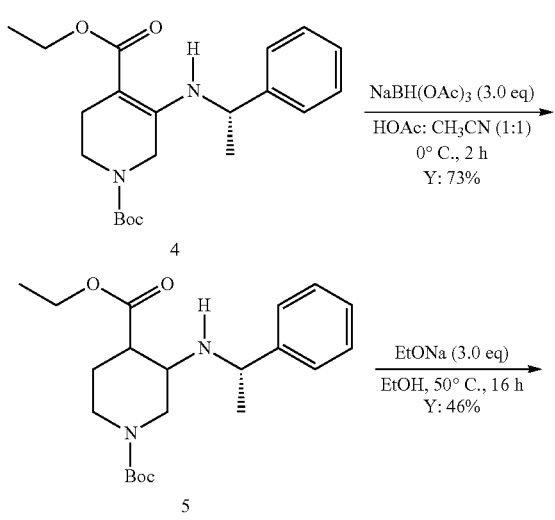

Preparation of ethyl 3-oxopiperidine-4-carboxylate intermediate

Ethyl 1-benzyl-3-oxopiperidine-4-carboxylate 1 (15.0 g, 50.5 mmol, 1.0 equiv) was hydrogenated in the presence of 10% Pd/C (1.5 g) catalyst under $H_2$ at atmospheric pressure in MeOH (250 mL) for 16 h. The catalyst was filtered off and the solvent was concentrated in vacuo to give ethyl 3-oxopiperidine-4-carboxylate 2 as a light yellow solid (10.2 g, yield: 98.0%). ESI-MS (M+H)$^+$: 172.1. $^1$H NMR (400 MHz, DMSO-$d_6$) δ: 4.23 (q, 2H), 3.75 (s, 2H), 3.37 (s, 2H), 3.20-3.16 (m, 2H), 2.44 (t, 1H), 1.25 (t, 3H).

Preparation of 1-tert-butyl 4-ethyl 3-oxopiperidine-1,4-dicarboxylate

Ethyl 3-oxopiperidine-4-carboxylate 2 (10.2 g, 60.0 mmol, 1.0 equiv) was dissolved in dry MeOH (200 mL), and Et$_3$N (33.1 mL, 240 mmol, 4.0 equiv) was added. The mixture was stirred for 1 h and Boc$_2$O (19.5 g, 90.0 mmol, 1.5 equiv) was added and stirred for 16 h. The solvent was concentrated in vacuo and the crude was purified by column chromatography (silica, petroleum ether/EtOAc=9:1) to give 1-tert-butyl 4-ethyl 3-oxopiperidine-1,4-dicarboxylate 3 light yellow oil (11.5 g, yield: 86%). ESI-MS (M+H−56)[+]: 216.0. $^1$H NMR (400 MHz, CDCl$_3$) δ: 4.24 (q, 2H), 4.03 (s, 2H), 3.49 (t, 2H), 2.33 (t, 2H), 1.47 (s, 9H), 1.31 (t, 3H).

Preparation of (S)-1-tert-butyl 4-ethyl 3-((1-phenylethyl)amino)-5,6-dihydro pyridine-1,4-(2H)-dicarboxylate In a dry flask equipped with a Dean-stark trap and reflux condenser, 1-tert-butyl 4-ethyl 3-oxopiperidine-1,4-dicarboxylate 3 (10.0 g, 37.0 mmol, 1.1 equiv) was dissolved in toluene (100 mL). S-(−)-α-Methylbenzylamine (4.9 g, 40.5 mmol, 1.1 equiv) and p-toluenesulfonic acid monohydrate (0.7 g, 3.7 mmol, 0.1 equiv) were added and the mixture was heated to reflux for 16 h. The crude reaction mixture was concentrated in vacuo to give (S)-1-tert-butyl 4-ethyl 3-((1-phenylethyl)amino)-5,6-dihydro pyridine-1,4(2H)-dicarboxylate 4 (12.0 g, Y: 88%) as thick orange oil which was used in next step without further purification, ESI-MS (M+H)[+]: 375.2.

Preparation of 1-tert-butyl 4-ethyl 3-(((S)1-phenylethyl)amino)-5,6-dihydro pyridine-1,4(2H)-dicarboxylate 1-tert-Butyl 4-ethyl 3-(((S)-1-phenylethyl)amino)piperidine-1,4-dicarboxylate 4 (11.2 g, 30.0 mmol, 1.0 equiv) was dissolved in a mixture of CH$_3$CN (60 mL) and acetic acid (60 mL) and cooled to 0° C. NaBH(OAc)$_3$ (19.0 g, 90.0 mmol, 3.0 equiv) was slowly added and the reaction mixture was allowed to stir for 2 h at 0° C. Saturated NaHCO$_3$ was slowly added to neutralize the solution to maintain the internal temperature of the flask below 10° C. The mixture was extracted with EtOAc (50 mL×3). The combined organic layer was dried (Na$_2$SO$_4$), filtered, concentrated in vacuo, and then purified by column chromatography (silica, petroleum ether/EtOAc=9:1) to give 4-ethyl 3-(((S)1-phenylethyl)amino)-5,6-dihydro pyridine-1,4(2H)-dicarboxylate 5 (8.2 g, Y: 73%) as light yellow oil. ESI-MS (M+H)[+]: 377.2. $^1$H NMR (400 MHz, CD$_3$OD) δ: 7.31-7.22 (m, 5H), 4.20 (q, 2H), 4.11-3.86 (m, 3H), 3.15 (s, 1H), 3.00-2.90 (m, 2H), 2.64 (d, 2H), 1.87-1.85 (m, 1H), 1.68 (s, 1H), 1.50-1.25 (m, 15H).

Preparation of trans-1-tert-butyl 4-ethyl 3-(((S)-1-phenylethyl)amino) piperidine-1,4-dicarboxylate The 1-tert-butyl 4-ethyl 3-(((S)-1-phenylethyl)amino)piperidine-1,4-dicarboxylate 5 (8.0 g, 21.2 mmol, 1.0 equiv) was dissolved in dry EtOH (20 mL) under N$_2$. In a separate flame-dried Schlenk flask was placed dry EtOH (150 mL), and sodium (0.450 g, 63.6 mmol, 3.0 equiv) was added portion-wise under N$_2$. The mixture was kept under N$_2$ and vented to remove evolved gases until all of the sodium had dissolved. The clear solution of 1-tert-butyl 4-ethyl 3-(((S)-1-phenylethyl)amino)piperidine-1,4-dicarboxylate was then transferred to the NaOEt solution, and the mixture was stirred at 80° C. under N$_2$ for 16 h. The solvent was removed under in vacuo, and brine (150 mL) was added and the mixture was brought to pH=10 with 1 N NaOH and extracted with EtOAc (100 mL×3). The combined organic layers were dried (Na$_2$SO$_4$) and concentrated in vacuo. The residue was purified by column chromatography (silica, petroleum ether/EtOAc=5:1) to give (trans)-1-tert-butyl 4-ethyl 3-(((S)-1-phenylethyl) amino)piperidine-1,4-dicarboxylate 6 as a slight yellow solid (3.7 g, yield: 46%). ESI-MS (M+H)[+]: 377.2.

Preparation of trans-1-tert-butyl 4-ethyl 3-aminopiperidine-1,4-dicarboxylate

Trans-1-tert-butyl 4-ethyl 3-(((S)-1-phenylethyl)amino) piperidine-1,4-dicarboxylate 6 (3.7 g, 8.3 mmol, 1.0 equiv) was hydrogenated in the presence of 10% Pd/C (0.37 g) catalyst under H$_2$ at 30 atmospheric pressure in MeOH (100 mL) at 50° C. for 8 h. The catalyst was filtered off and the solvent was removed in vacuo to give (trans)-1-tert-butyl 4-ethyl 3-aminopiperidine-1,4-dicarboxylate 7 as light yellow oil (2.5 g, yield: 92%). ESI-MS (M+H)[+]: 273.1. $^1$H NMR (400 MHz, CDCl$_3$) δ: 4.18 (q, 2H), 3.97-3.94 (m, 2H), 3.37 (s, 1H), 3.07-3.02 (m, 1H), 2.89-2.85 (m, 1H), 2.60-2.55 (m, 1H), 2.01-1.91 (m, 1H), 1.70-1.54 (m, 3H), 1.46 (s, 9H), 1.28 (t, 3H).

Synthesis of trans-1-tert-butyl 4-ethyl 3-(5-bromopentanamido)piperidine-1,4-dicarboxylate To a solution of trans-1-tert-butyl 4-ethyl 3-aminopiperidine-1,4-dicarboxylate 7 (2.5 g, 9.2 mmol, 1.0 equiv) in CH$_2$Cl$_2$ (50 mL), Et$_3$N (2.5 mL, 18.4 mmol, 2.0 equiv) was added at rt. After the reaction solution was stirred at rt for 10 min, 5-bromovaleryl chloride (1.9 g, 9.6 mmol, 1.05 eq) was added. The reaction solution was stirred at rt for 2 h. The mixture was quenched with H$_2$O (20 mL) and extracted with CH$_2$Cl$_2$ (50 mL×3). The organic layer was collected, concentrated in vacuo, and the residue was purified by column chromatography (silica, petroleum ether/EtOAc=1:1) to give (trans)-1-tert-butyl 4-ethyl 3-(5-bromopentanamido)piperidine-1,4-dicarboxylate 8 as yellow oil (3.2 g, yield: 80%). ESI-MS (M+H−56)[+]: 379.0. $^1$H NMR (400 MHz, CDCl$_3$) δ: 5.99 (d, 1H), 4.39-4.38 (m, 1H), 4.15 (q, 2H), 3.79-3.74 (m, 1H), 3.66-3.60 (m, 1H), 3.41 (t, 2H), 3.30-3.26 (m, 1H), 3.21-3.14 (m, 1H), 2.78-2.74 (m, 1H), 2.19 (t, 2H), 1.99-1.85 (m, 3H), 1.80-1.72 (m, 3H), 1.45 (s, 9H), 1.27 (t, 3H).

Synthesis of trans-1'-tert-butyl 4'-ethyl 2-oxo-[1,3'-bipiperidine]-1',4'-dicarboxylate To a solution of trans-1-tert-butyl 4-ethyl 3-(5-bromopentanamido)piperidine-1,4-dicarboxylate 8 (3.0 g, 6.9 mmol, 1.0 equiv) in THF (20 mL), NaH (276 mg, 6.9 mmol, 1.0 equiv) was carefully added in small portions at 0° C. The reaction solution was stirred at reflux condition for 4 h. The mixture was quenched with H$_2$O (20 mL), and extracted with EtOAc (30 mL×3). The organic layer was collected, dried (Na$_2$SO$_4$), filtered, and concentrated in vacuo. The residue was purified by column chromatography (silica, petroleum ether/EtOAc=1:2) to give (trans)-1'-tert-butyl 4'-ethyl 2-oxo-[1,3'-bipiperidine]-1',4'-dicarboxylate 9 as a slight yellow oil (2.1 g, yield: 88%). ESI-MS (M+H−56)[+]: 299.1. $^1$H NMR (400 MHz, CDCl$_3$) δ: 4.10 (q, 4H), 3.38-3.19 (m, 4H), 2.70-2.61 (m, 1H), 2.36-2.31 (m, 2H), 1.95-1.92 (m, 1H), 1.75-1.71 (m, 6H), 1.46 (s, 9H), 1.23 (t, 3H).

Example 2

Preparation of trans-1'-(6-amino-5-fluoropyrimidin-4-yl)-3-((3-chloro-5-(trifluoromethyl)phenyl)amino)-2-oxo-[1,3'-bipiperidine]-4'-carboxamide

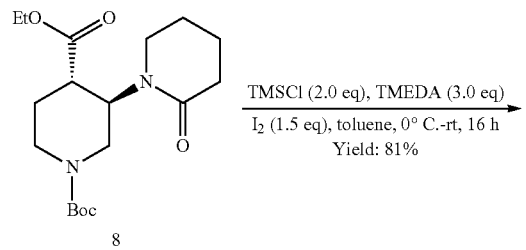

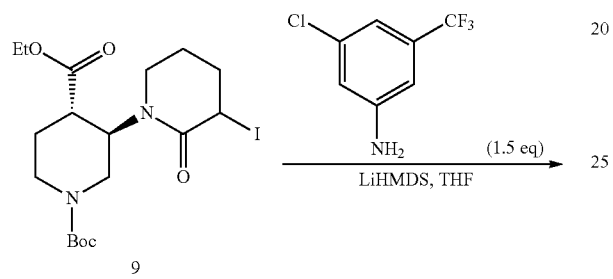

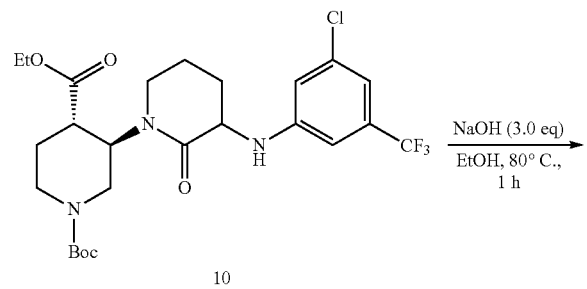

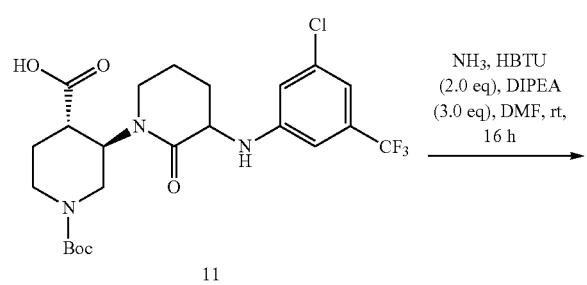

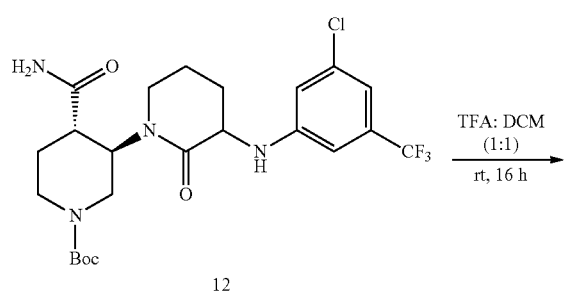

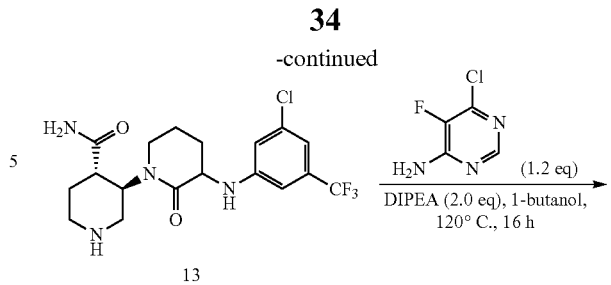

Synthesis of trans-1'-tert-butyl-4'-ethyl-3-iodo-2-oxo-[1,3'-bipiperidine]-1',4'-dicarboxylate To the solution of trans-1'-tert-butyl 4'-ethyl 2-oxo-[1,3'-bipiperidine]-1',4'-dicarboxylate 8 (141 mg, 2.58 mmol, 1.0 equiv) in dry toluene (10 mL) at 0° C., TMEDA (0.89 g, 7.7 mmol, 3.0 equiv) and TMSCl (0.6 mg, 1.0 mmol, 2.0 equiv) were added successively under $N_2$. After 0.5 h, $I_2$ (0.98 g, 3.87 mmol, 1.5 equiv) was carefully added in small portions. The reaction solution was stirred at 0° C. to rt for 16 h. The mixture was diluted with EtOAc (100 mL), washed with saturated $Na_2S_2O_3$ (20 mL×2) and brine (20 mL), dried ($Na_2SO_4$), filtered, and concentrated in vacuo. The crude product 9 (2.2 g, Y: 81%) was used directly in the next step without further purification. ESI-MS (M+H−56)$^+$: 424.9. $^1$H NMR (400 MHz, CDCl$_3$) δ: 4.78-4.73 (m, 1H), 4.19-4.04 (m, 4H), 3.55-3.30 (m, 4H), 3.24-3.16 (m, 2H), 2.73-2.60 (m, 1H), 2.22-2.14 (m, 2H), 1.96-1.78 (m, 2H), 1.70-1.60 (m, 1H), 1.44 (s, 9H), 1.25 (t, J=7.2 Hz, 3H).

Synthesis of trans-1'-tert-butyl 4'-ethyl 3-((3-chloro-5-(trifluoromethyl) phenyl)amino)-2-oxo-[1,3'-bipiperidine]-1',4'-dicarboxylate A 1.0 M solution of lithium bis(trimethyldisilyl)amide in THF (13 mL, 12 mmol, 2.0 equiv) was added through an addition funnel at 10-15° C. to a solution of 3-chloro-5-(trifluoromethyl)aniline (15 g, 78 mmol, 1.2 equiv) in THF (13 mL). The mixture was allowed to stir at room temperature for 20 min and a solution of crude trans-1'-tert-butyl-4'-ethyl-3-iodo-2-oxo-[1,3'-bipiperidine]-1',4'-dicarboxylate 9 (3.7 g, 65 mmol, 1.0 equiv) in THF (13 mL) was added through an addition funnel at 10-15° C. over 30 min. After addition, the reaction was allowed to stir at the temperature for 30 min. Upon completion, the reaction was cooled to 5° C. and quenched slowly with water (10 mL), keeping the temperature below 20° C. The quenched reaction was extracted with EtOAc (2×30 mL). The combined organic layers were washed with saturated brine (30 mL), dried ($Na_2SO_4$), filtered, and concentrated in vacuo. The resulting crude product was purified over silica gel eluting with a gradient of 10% to 75% of EtOAc in heptanes to give the desire product 10. ESI-MS (M+H−56)⁺: 463.1. ¹H NMR (400 MHz, CDCl₃) δ: 6.92 (s, 1H), 6.71-6.69 (m, 2H), 4.17-4.06 (m, 4H), 3.78-3.68 (m, 2H), 3.46-3.36 (m, 3H), 3.23-3.07 (m, 2H), 2.73-2.65 (m, 1H), 2.44-2.37 (m, 1H), 2.03-1.85 (m, 3H), 1.71-1.61 (m, 2H), 1.46 (s, 9H), 1.27-1.19 (m, 3H).

Synthesis of trans-1'-(tert-butoxycarbonyl)-3-((3-chloro-5-(trifluoromethyl) phenyl) amino)-2-oxo-[1,3'-bipiperidine]-4'-carboxylic acid To a solution of trans-1'-tert-butyl 4'-ethyl 3-((3-chloro-5-(trifluoromethyl)phenyl)amino)-2-oxo-[1,3'-bipiperidine]-1',4'-dicarboxylate 10 (180 mg, 0.33 mmol, 1.0 equiv) in EtOH (5 mL) was added NaOH (40 mg, 0.99 mmol, 3.0 equiv) and solution was stirred at 80° C. for 1 h. The solvent was concentrated in vacuo and the residue was suspended in water (10 mL) and adjusted to pH=6 with HCl (4 N). The precipitate was filtered to afford (trans)-1'-(tert-butoxycarbonyl)-3-((3-chloro-5-(trifluoromethyl)phenyl)amino)-2-oxo-[1,3'-bipiperidine]-4'-carboxylic acid 11 (150 mg, Y: 82%) as yellow solid which was used next step without further purification. ESI-MS (M+H−85)⁺: 463.1. ¹H NMR (400 MHz, CDCl₃) δ: 6.85 (s, 1H), 6.82 (s, 1H), 6.78 (s, 1H), 4.12-3.96 (m, 4H), 3.53-3.37 (m, 2H), 3.11-3.04 (m, 2H), 2.75-2.67 (m, 1H), 2.24-2.18 (m, 1H), 1.98-1.89 (m, 3H), 1.71-1.58 (m, 2H), 1.44 (s, 9H).

Synthesis of trans-tert-butyl 4'-carbamoyl-3-((3-chloro-5-(trifluoromethyl) phenyl)amino)-2-oxo-[1,3'-bipiperidine]-1'-carboxylate To the solution of trans 1'-(tert-butoxycarbonyl)-3-((3-chloro-5-(trifluoromethyl)phenyl)amino)-2-oxo-[1,3'-bipiperidine]-4'-carboxylic acid 11 (70 mg, 0.14 mmol, 1.0 equiv) in DMF (2 mL), was added NH₄Cl (22 mg, 0.41 mmol, 3.0 equiv), HBTU (103 mg, 0.270 mmol, 2.0 equiv) and DIPEA (52 mg, 0.41 mmol, 3.0 equiv). The reaction solution was stirred at rt for 16 h, diluted with EtOAc (10 mL) and washed with water (5 mL) and brine (5 mL). The organic phase was separated and concentrated in vacuo to afford a crude oil which was purified by pre-HPLC (MeOH/H₂O with 0.05% TFA as mobile phase) to give the compound (trans)-tert-butyl4'-carbamoyl-3-((3-chloro-5-(trifluoromethyl) phenyl) amino)-2-oxo-[1,3'-bipiperidine]-1'-carboxylate 12 (60 mg, yield: 86%) as a light solid. ESI-MS (M+H−56)⁺: 463.1. ¹H NMR (400 MHz, CD₃OD) δ: 6.87-6.86 (m, 1H), 6.84-6.83 (m, 1H), 6.80 (s, 1H), 4.11-4.03 (m, 3H), 3.53-3.35 (m, 2H), 3.20-3.08 (m, 2H), 2.77-2.74 (m, 1H), 2.25-2.18 (m, 1H), 1.99-1.88 (m, 3H), 1.70-1.60 (m, 2H), 1.46 (s, 9H).

Synthesis of trans-3-((3-chloro-5-(trifluoromethyl) phenyl)amino)-2-oxo-[1,3'-bipiperidine]-4'-carboxamide To the solution of trans-tert-butyl 4'-carbamoyl-3-((3-chloro-5-(trifluoromethyl)phenyl)amino)-2-oxo-[1,3'-bipiperidine]-1'-carboxylate 12 (60 mg, 0.11 mmol) in CH₂Cl₂ (1.0 mL) was added CF₃CO₂H (1.0 mL) at rt. The reaction mixture was stirred at rt for 2 h, concentrated in vacuo to give desired product 13 (43 mg, 90%) which was used directly in the next step without further purification. ESI-MS (M+H)⁺: 419.0.

Synthesis of trans-1'-(6-amino-5-fluoropyrimidin-4-yl)-3-((3-chloro-5-(trifluoromethyl)phenyl)amino)-2-oxo-[1,3'-bipiperidine]-4'-carboxamide To a solution of trans-3-((3-chloro-5-(trifluoromethyl)phenyl)amino)-2-oxo-[1,3'-bipiperidine]-4'-carboxamide 13 (42 mg, 0.10 mmol, 1.0 equiv) in 1-butanol (2 mL), 6-chloro-5-fluoropyrimidin-4-amine (18 mg, 0.12 mmol, 1.2 equiv) was added DIPEA (26 mg, 0.20 mmol, 2.0 equiv). The reaction solution was stirred at 120° C. for 16 h. The mixture was diluted with EtOAc (20 mL), washed with H₂O (10 mL) and brine (10 mL), dried (Na₂SO₄), filtered, and concentrated in vacuo. The crude was by purified by pre-HPLC (MeOH/H₂O with 0.05% TFA as mobile phase) to give the compound (trans)-1'-(6-amino-5-fluoropyrimidin-4-yl)-3-((3-chloro-5-(trifluoromethyl)phenyl)amino)-2-oxo-[1,3'-bipiperidine]-4'-carboxamide 14 (44 mg, yield: 83%) as a yellow solid. ESI-MS (M+H)⁺: 530.0. HPLC: (214 nm: 100%, 254 nm: 100%). ¹H NMR (400 MHz, CD₃OD) δ: 7.97 (s, 1H), 6.84 (s, 1H), 6.81 (s, 1H), 6.76 (s, 1H), 4.58-4.52 (m, 2H), 4.09-4.03 (m, 1H), 3.52-3.35 (m, 3H), 3.29-3.27 (m, 4H), 3.12-3.05 (m, 1H), 2.24-2.17 (m, 1H), 2.02-1.91 (m, 3H), 1.80-1.63 (m, 2H).

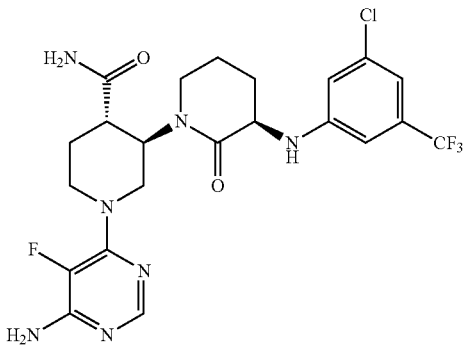 [SMILES: NC(=O)[C@H]1CCN(c2ncnc(N)c2F)C[C@@H]1N1CCC[C@@H](Nc2cc(Cl)cc(C(F)(F)F)c2)C1=O]

(3R,3'R,4'S)-1'-(6-amino-5-fluoropyrimidin-4-yl)-3-((3-chloro-5-(trifluoromethyl) phenyl)amino)-2-oxo-[1,3'-bipiperidine]-4'-carboxamide The mixture of four diastereomers of compound 14 was separated into three peaks by SFC (IA (2×15 cm), 30% EtOH (0.1% DEA)/CO₂, 100 bar, 60 ml/min) and the title compound corresponded to peak 3. LCMS (Agilent460, 254 nm): ES (+) MS m/e=530.1 (M+1) @ 1.20 min. ¹H NMR (400 MHz, DMSO-d₆) δ: 7.77 (d, J=2.01 Hz, 1H), 7.38 (br. s., 1H), 6.94 (s, 2H), 6.75-6.87 (m, 2H), 6.41-6.66 (m, 3H), 4.29 (br. s., 1H), 4.23 (d, J=13.05 Hz, 1H), 3.96-4.18 (m, 2H), 3.44 (td, J=6.15, 12.30 Hz, 1H), 3.24-3.33 (m, 1H), 3.10 (br. s., 1H), 2.88 (br. s., 1H), 2.82 (t, J=12.30 Hz, 1H), 2.13 (qd, J=5.94, 12.30 Hz, 1H), 1.74-1.93 (m, 3H), 1.58-1.74 (m, 1H), 1.41-1.58 (m, 1H).

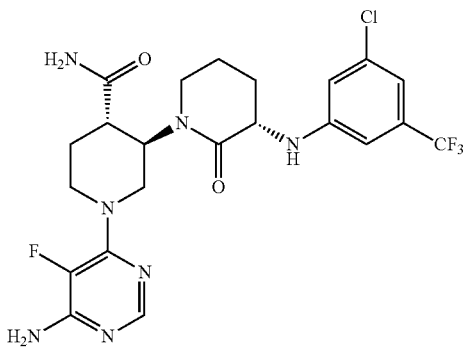

(3S,3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxamide The mixture of four diastereomers of compound 14 was separated into three peaks by SFC (IA (2×15 cm), 30% EtOH (0.1% DEA)/CO$_2$, 100 bar, 60 ml/min) and the title compound corresponded to peak 2. LCMS (Agilent460, 254 nm): ES (+) MS m/e=530.1 (M+1) @ 1.19 min. $^1$H NMR (400 MHz, DMSO-d$_6$) δ: 7.77 (d, J=1.76 Hz, 1H), 7.39 (br. s., 1H), 6.98 (s, 1H), 6.96 (s, 1H), 6.72-6.88 (m, 2H), 6.57 (s, 2H), 6.54 (d, J=7.78 Hz, 1H), 4.05-4.33 (m, 4H), 3.37 (t, J=6.27 Hz, 2H), 3.11 (br. s., 1H), 2.94 (br. s., 1H), 2.82 (t, J=12.30 Hz, 1H), 2.02-2.16 (m, 1H), 1.75-1.92 (m, 3H), 1.57-1.74 (m, 1H), 1.36-1.54 (m, 1H).

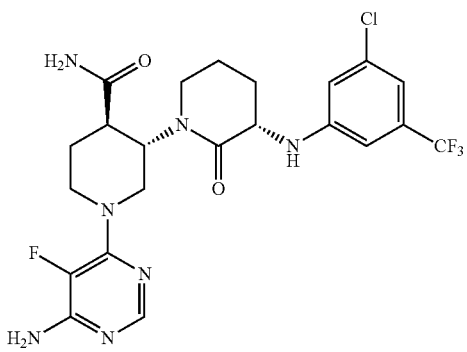

(3S,3'S,4'R)-1'-(6-amino-5-fluoropyrimidin-4-yl)-3-((3-chloro-5-(trifluoromethyl)phenyl)amino)-2-oxo-[1,3'-bipiperidine]-4'-carboxamide The mixture of four diastereomers of compound 14 was separated into three peaks by SFC (IA (2×15 cm), 30% EtOH (0.1% DEA)/CO$_2$, 100 bar, 60 ml/min). Peak 1 of 3 was further purified SFC (AD-H (2×15 cm), 30% iPrOH (0.1% DEA)/CO$_2$, 100 bar, 60 ml/min) to afford the title compound. LCMS (Agilent 460, 254 nm): ES (+) MS m/e=530.1 (M+1) @ 1.20 min. $^1$H NMR (400 MHz, DMSO-d$_6$) δ: 7.77 (d, J=1.76 Hz, 1H), 7.38 (br. s., 1H), 6.94 (s, 2H), 6.83 (s, 1H), 6.80 (s, 1H), 6.42-6.66 (m, 3H), 4.18-4.47 (m, 2H), 3.95-4.18 (m, 2H), 3.39-3.52 (m, 1H), 3.24-3.31 (m, 1H), 3.10 (br. s., 1H), 2.88 (br. s., 1H), 2.82 (t, J=12.30 Hz, 1H), 2.13 (qd, J=5.91, 12.39 Hz, 1H), 1.73-1.92 (m, 3H), 1.58-1.73 (m, 1H), 1.42-1.58 (m, 1H).

(3R,3'S,4'R)-1'-(6-amino-5-fluoropyrimidin-4-yl)-3-((3-chloro-5-(trifluoromethyl)phenyl)amino)-2-oxo-[1,3'-bipiperidine]-4'-carboxamide The mixture of four diastereomers of compound 14 was separated into three peaks by SFC (IA (2×15 cm), 30% EtOH (0.1% DEA)/CO$_2$, 100 bar, 60 ml/min). Peak 1 of 3 was further purified SFC (AD-H (2×15 cm), 30% iPrOH (0.1% DEA)/CO$_2$, 100 bar, 60 ml/min) to afford the titled compound. LCMS (Agilent 460, 254 nm): ES (+) MS m/e=530.1 (M+1) @ 1.20 min. $^1$H NMR (400 MHz, DMSO-d$_6$) δ: 7.77 (d, J=1.76 Hz, 1H), 7.39 (br. s., 1H), 6.98 (s, 1H), 6.96 (s, 1H), 6.73-6.88 (m, 2H), 6.57 (s, 2H), 6.54 (d, J=7.78 Hz, 1H), 4.05-4.35 (m, 4H), 3.37 (t, J=6.15 Hz, 2H), 3.12 (br. s., 1H), 2.94 (br. s., 1H), 2.82 (t, J=12.30 Hz, 1H), 2.09 (sxt, J=5.80 Hz, 1H), 1.74-1.92 (m, 3H), 1.56-1.73 (m, 1H), 1.36-1.52 (m, 1H).

Example 3

Alternative Synthesis of (3R,3'R,4'S)-1'-(6-amino-5-fluoropyrimidin-4-yl)-3-((3-chloro-5-(trifluoromethyl) phenyl)amino)-2-oxo-[1,3'-bipiperidine]-4'-carboxamide In addition to the methods described in Example 2, (3R,3'R,4'S)-1'-(6-amino-5-fluoropyrimidin-4-yl)-3-((3-chloro-5-(trifluoromethyl) phenyl)amino)-2-oxo-[1,3'-bipiperidine]-4'-carboxamide (compound I-1) was also synthesized according to Scheme 6.

Scheme 6

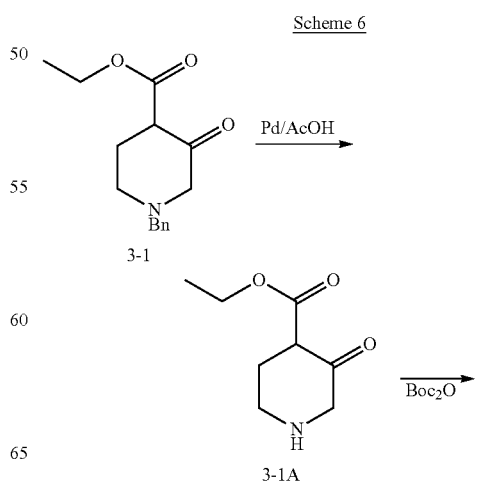

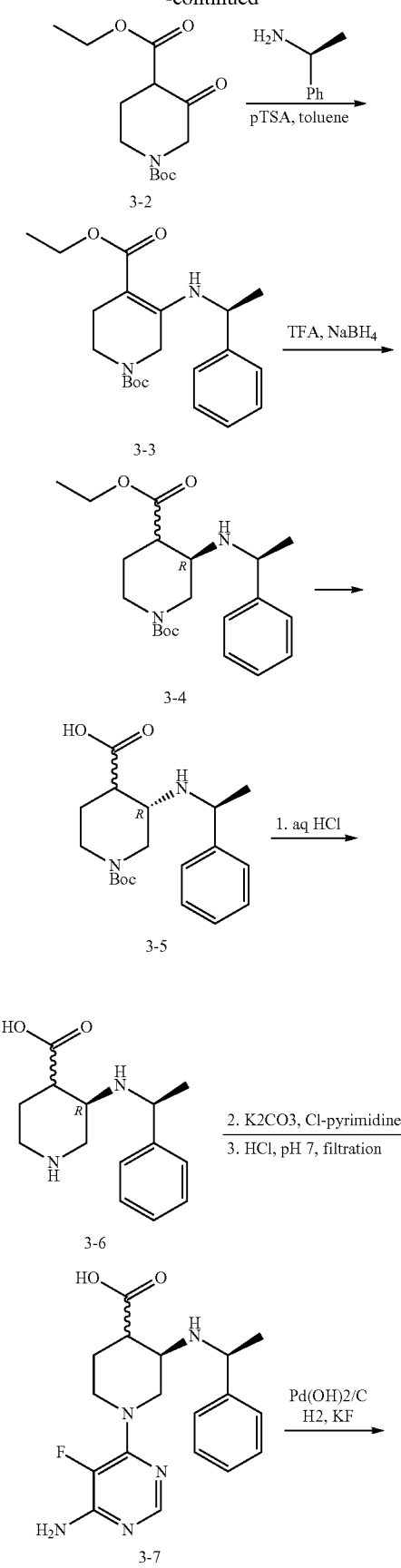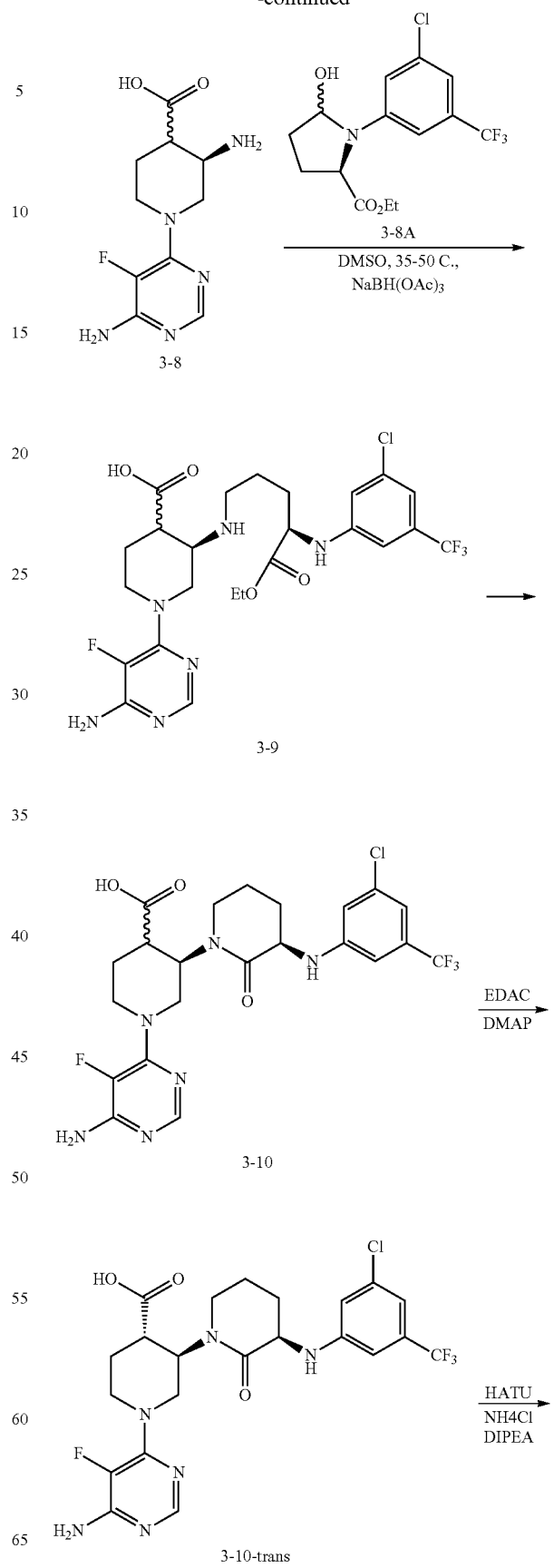

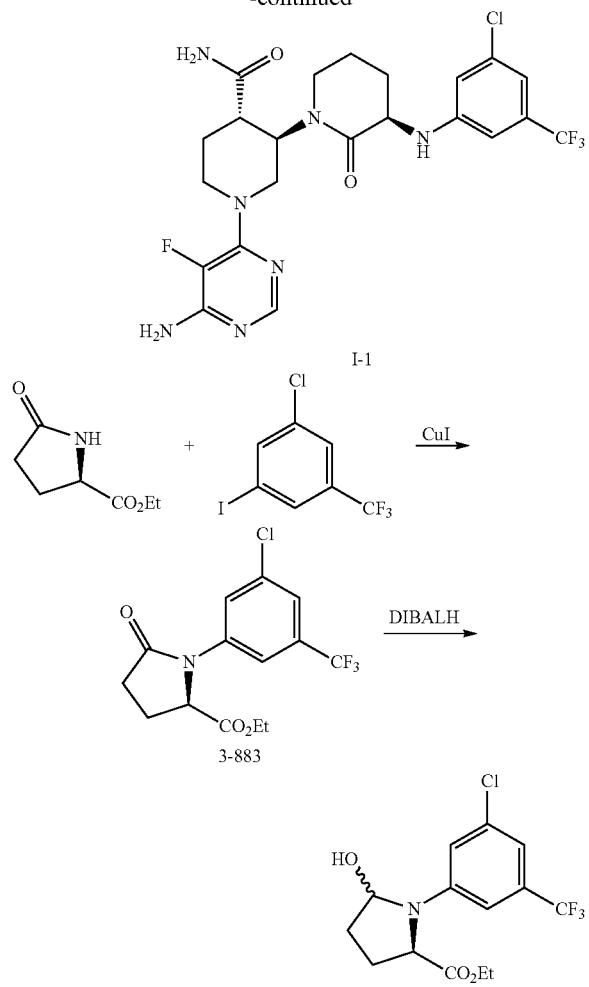

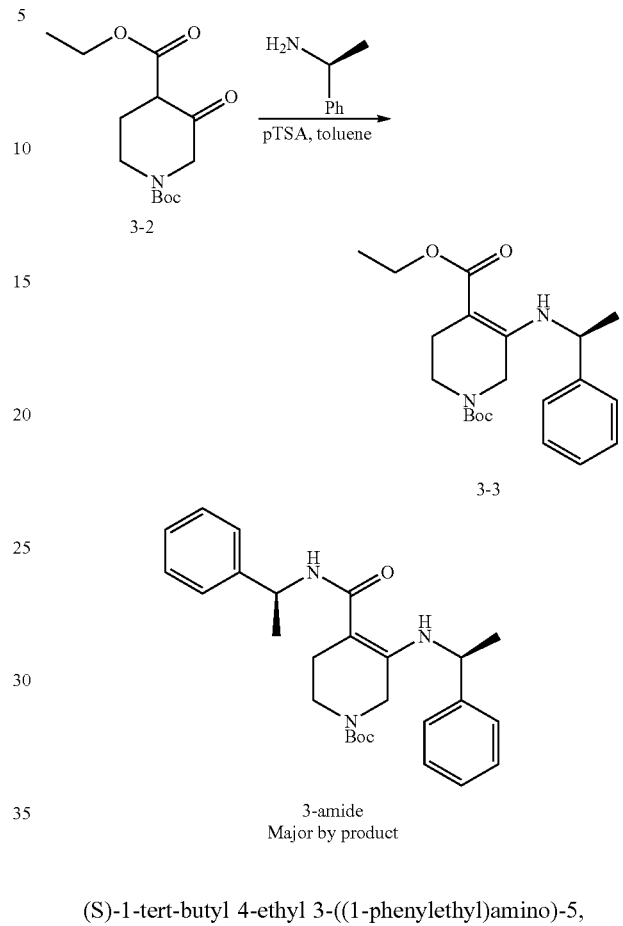

filtrate was concentrated in vacuo to afford crude 3-2 (5.2 kg) as an oil, which was used in next step without further purification.

(S)-1-tert-butyl 4-ethyl 3-((1-phenylethyl)amino)-5,6-dihydropyridine-1,4 (2H)-dicarboxylate (3-3)

To a 100 L reactor equipped with Dean-Stark apparatus was charged toluene (20 L), crude compound 3-2 (5.2 kg, 19.1 mol, 1.0 equiv) rinsed with toluene (30 L), pTSA (329 g, 0.2 mol, 0.01 equiv), and S-(−)-α-methylbenzylamine 0.95 kg, 16.2 mol, 0.85 equiv). The mixture was heated to reflux with a nitrogen blanket and the water was removed through Dean-Stark. After 18 hours, LC-MS indicated complete consumption of 3-2. The mixture was then cooled to the ambient temperature. The insolubles were removed by filtration, and the filtrate was concentrated in vacuo to dryness to afford crude 3-3 as a thick oil. This crude product was used in the next step without further purification. 3-10% of amide byproduct formed in this reaction and its structure was tentatively assigned based on LC-MS data.

1-tert-Butyl 4-ethyl 3-oxopiperidine-1,4-dicarboxylate 3-2

To a solution of 3-1 (5.0 kg, 19.1 mol, 1.0 equiv) in EtOH (50 L) under $N_2$ was added (Boc)$_2$O (4.2 kg, 19.1 mol, 1.0 equiv), Et$_3$N (1.9 kg, 19.1 mol, 1.0 equiv) and 10% Pd(OH)$_2$/C (250 g, 10% w/w). After evacuated and refilled with hydrogenation three times, the mixture was stirred under 1 atm of hydrogen at 50° C. for 15 hr. LC-MS indicated completely consumption of 3-1. After the mixture was cooled to ambient temperature, the catalyst was filtered through a layer of celite and washed with EtOH (2.5 L). The

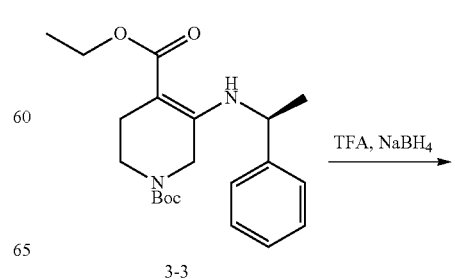

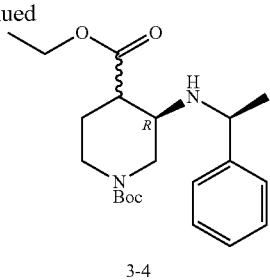

3-4

(70:30 cis/trans; 13-16:1 3R/3S)

(3R)-1-tert-butyl 4-ethyl 3-(((S)-1-phenylethyl) amino)piperidine-1,4-dicarboxylate (3-4)

To a 100 L reactor charged with NaBH$_4$ (1.16 kg, 30.5 mol, 2.0 equiv) and anhydrous THF (60 L) under nitrogen was added TFA (10.5 kg, 92 mol, 6.0 equiv) slowly over 30 min while maintaining temperature at 0-5° C. The mixture was then cooled to −45° C. In a separation reactor, crude product 3-3 was dissolved in anhydrous acetonitrile (30 L), which was added slowly to the above solution of NaBH$_4$/TFA while maintaining the internal temperature between −45~−30° C. The mixture was stirred at −45° C. for 1 h, after which time, HPLC indicated complete consumption of compound 3-3. The mixture was slowly diluted with ice water (50 kg) and the mixture was then warmed to 10° C. The product was extracted with EtOAc (2×40 L) and the combined organic layers were washed with saturated NaHCO$_3$ solution (20 L). pH of the aqueous was ~8. The organic layers were dried (Na$_2$SO$_4$) and concentrated in vacuo to nearly dryness to afford a residue which was further azeotroped with MeOH (10 L×3) to remove excess EtOAc. In the end, a 10 L solution of crude 3-4 in MeOH was obtained, which was used directly in the subsequent step without further purification. ESI-MS (M+H−1)$^+$: 377.2. $^1$H NMR (400 MHz, CD$_3$OD) δ: 7.31-7.22 (m, 5H), 4.20 (q, 2H), 4.11-3.86 (m, 3H), 3.15 (s, 1H), 3.00-2.90 (m, 2H), 2.64 (d, 2H), 1.87-1.85 (m, 1H), 1.68 (s, 1H), 1.50-1.25 (m, 15H).

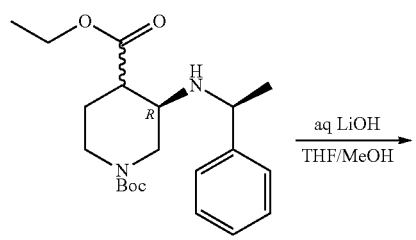

3-4

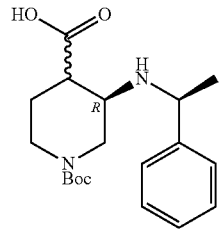

3-5

(3R)-1-(tert-butoxycarbonyl)-3-(((S)-1-phenylethyl) amino)piperidine-4-carboxylic acid (3-5)

To a 100 L reactor were charged a with THF/MeOH (1:1, 80 L), was added a solution of LiOH.H$_2$O (2.5 kg, 60 mol, 4.0 equiv) in water (10 L) and a solution of crude 3-4 in MeOH (10 L) from the above step. The resulting mixture was stirred at 22° C. for 18 hours, at which time LC/MS indicated complete consumption of starting material 3-4. The solution was diluted with MTBE (40 L) and stirred for 20 min. The aqueous layer was separated, cooled to 0° C. and neutralized with 3N HCl solution to pH between 7-8, while maintaining the internal temperature below 10° C. The solution was washed with DCM (5×30 L) or until the LC/MS indicated no product 3-5 remained in the aqueous layer. The combined organic layers were concentrated in vacuo to dryness, suspended in EtOAc and petroleum ether (2:1, 10 L) and stirred for 2 hours, the solids were filtered, washed by petroleum ether (5 L) and dried under vacuum at 50° C. for 18 hours to give product (3.5 Kg, 53% yield) as a solid with 95% purity. Compound 3-5 is a mixture of ~30:70 trans/cis at C-4 and ~93:7 R:S at C-3. The average overall yield from 3-1 is 43-55%. ESI-MS (M+H−1)$^+$: 349.2. $^1$H NMR (400 MHz, CD$_3$OD) δ: 8.22-8.06 (m, 5H) 4.11 (m, 1H), 3.86-3.82 (m, 1H), 3.59-3.56 (m, 1H), 2.79-2.65 (m, 1H), 3.22-2.62 (m, 2H), 2.06-2.16 (m, 12H).

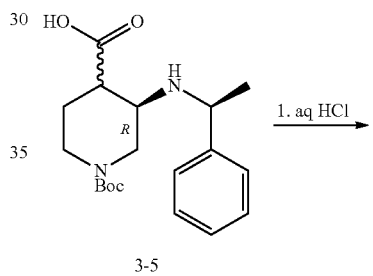

3-5

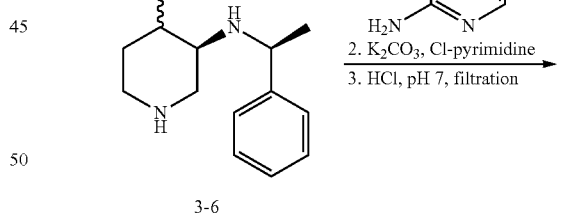

3-6

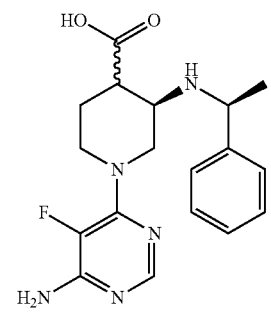

3-7

(3R)-1-(6-amino-5-fluoropyrimidin-4-yl)-3-(((S)-1-phenylethyl)amino)piperidine-4-carboxylic acid (3-7)

To a 50 L reactor was charged with 10 L of 2N HCl and 3-5 (850 g, 2.44 mol, 1.0 equiv). The mixture was warmed to 30° C. and stirred for 2 hours, at which time HPLC indicted complete consumption of starting 3-5. The solution was diluted with MTBE (4 L) and stirred for 20 min, layers were separated and to the aqueous layer was added solid $K_2CO_3$ (660 g) over 1 hour to pH ~7. Additional $K_2CO_3$ (660 g, 4.8 mol, 2.0 equiv) was added following by 6-chloro-5-fluoropyrimidine-4-ylamine (360 g, 2.44 mole 1.0 equiv) and 1,4-dioxane (5 L). The mixture was heated to gentle reflux at 100° C. and stirred at this temperature for 16 hours. HPLC indicated <2% of compound 3-6 remained. The mixture was washed with DCM (2×5 L) and the organic wash solutions were discarded. The aqueous layer was treated with active carbon (425 g) by stirring the slurry for 1 hour at 30° C. followed by filtration through diatomite. This active carbon treatment was repeated. The resulting aqueous solution was neutralized to pH ~7 with concentrated HCl, and stirred at 22° C. for 3 hours, the resulting slurry was filtered and the wet cake was washed with washed with 1,4-dioxane/water (1:1, 1.2 L), dried under vacuum at 50° C. for 18 hr until KF ~0.5%. of product 3-7 was obtained as a pale white solid (690 g, 81% yield) with purity of 98.6%. The product contains a mixture of 1:9 cis/trans iomers at the C3 and C4 positions. ESI-MS (M+H−1)$^+$: 460.2. $^1$H NMR (400 MHz, CD$_3$OD) δ: 8.49 (d, J=2.01 Hz, 1H), 8.21-8.14 (m, 5H) 4.94-4.90 (m, 1H), 4.63 (d, J=11.55 Hz, 1H), 4.42 (m, 1H), 4.03 (m, 2H), 3.59-3.72 (m, 3H), 2.84-2.93 (m, 1H), 2.20-2.31 (m, 1H), 2.15 (d, J=6.78 Hz, 3H).

(3R)-3-amino-1-(6-amino-5-fluoropyrimidin-4-yl)piperidine-4-carboxylic acid (3-8)

To a 10 L reaction were charged under $N_2$, i-PrOH (3.5 L), $H_2O$ (3.5 L), 3-7 (1.0 equiv, 0.97 mol, 350 g), potassium fluoride mono hydrate (290 g, 3.0 eq, 3.0 mol) and 35 g of 20% Pd(OH)$_2$/C (10% v/w). After evacuated/refilled with hydrogen three times, the mixture was warmed to 40-50° C. and vigorously stirred at that temperature under 1 atmosphere of hydrogen. After 18 hours, LC/MS indicated <1% of starting material 3-7 remained. The mixture was purged with $N_2$ for 20 min, cooled to 22° C., and filtered. Both the wet cake and filtrate contained the product and processed separately.

The filtrate was concentrated in vacuo at 50° C. to a volume of ~200 mL. After cooled to 20° C. and stirred at this temperature for 2 hours, a slurry was obtained, and the solid was filtered, washed with water (400 mL) and dried under vacuum and at 50° C. to give product 3-8 (65 g). The wet cake from the reaction filtration was stirred in 1N HCl (1 L) for 2 hours to dissolve the product and the remaining catalyst solid was then removed by filtration. The acidic filtrate was neutralized with solid LiOH to pH ~7 to precipitate the product 3-8. The product was washed with water (200 mL), dried under vacuum and at 50° C. to give 120 g of product. A total of 185 g of product was obtained with 98.7% purity and in 75% yield based on H NMR. All the mother liquors were combined and concentrated to a volume of ~400 mL result in a slurry, filtration, wash with water and drying gave additional 64 g solid with ~50% purity. $^1$H NMR (400 MHz, D$_2$O): δ 7.77 (s, 1H) 4.12 (d, J=14.05 Hz, 1H), 4.01 (d, J=13.05 Hz, 1H), 3.26 (d, J=13.80 Hz, 1), 2.99-3.10 (m, 1H), 2.64-2.73 (m, 1H), 1.98 (dd, J=3.39, 14.18 Hz, 1H), 1.74-1.87 (m, 1H).

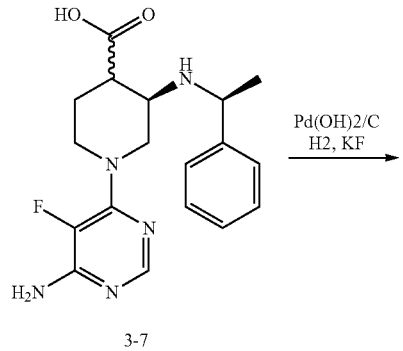

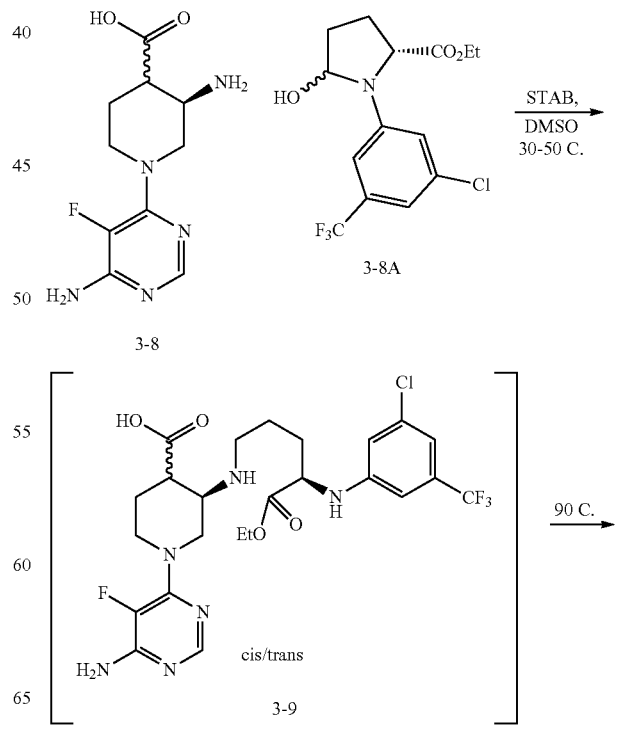

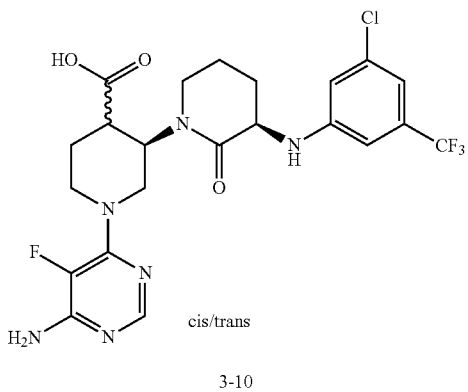

((3R,3'R)-1'-(tert-butoxycarbonyl)-3-((3-chloro-5-(trifluoromethyl)phenyl)amino)-2-oxo-[1,3'-bipiperidine]-4'-carboxylic acid (3-10)

To a solution of 3-8 (440 g, 1.9 mole, 1.0 equiv) in DMSO (10 L) was added 3-8A sequentially (640 g, 1.9 mole, 1.0 equiv) and sodium triacetoxyborohydride (STAB, 402.0 g, 3.8 mole, 2 equiv) and Et$_3$N (, 190 g, 1.9 mol, 1.0 equiv). The mixture was heated to 50° C. and stirred for 3 hours to show complete conversion by HPLC to intermediate 3-9.

The solution was diluted with MeOH (182 g, 5.7 mol, 3.0 eq,) to quench the excess of STAB, and the reaction was heated to 70-80° C. After 16 hours, HPLC indicated 22% of product 3-10 formed and 61% intermediate 3-9 remained and chiral HPLC indicated ~3% lactam epimer. The mixture was held at 70-80° C. for additional 24 hours to give 50% 3-10, 35% 3-9, and 7% lactam epimer. After another 40 hours stirring, 80% 3-10 formed, 4% 3-9 remained, and the lactam epimer increased to 14%. The mixture was cooled to 22° C., and quenched with 2N NH$_4$Cl solution (5 L) to give a slurry mixture. After 30 minute stirring, the mixture was filtered and the wet cake was washed with water (3 L), dried under vacuum and at 55° C. until KF<0.1. Crude 3-10 was obtained as a brown solid (850 g, 97.7%); chiral HPLC indicted 12.5% lactam epimer. This product was used directly without further purification

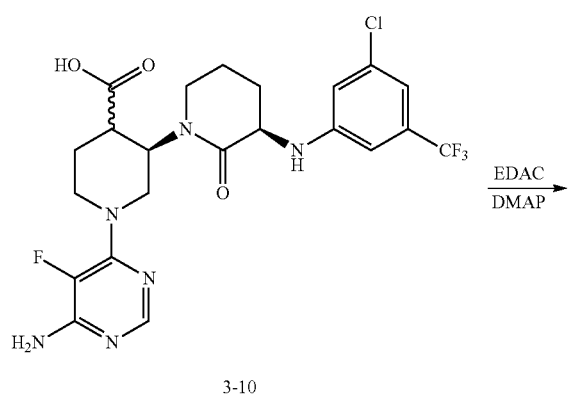

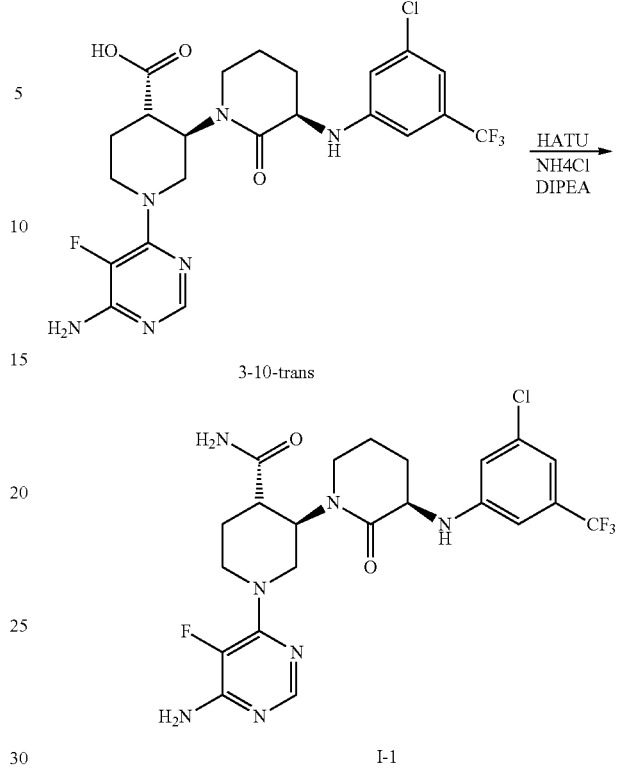

(3R,3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxylic acid (3-10-trans)

To a 10 L reactor was charged under N$_2$ with 3-10 (850 g, 1.9 mol, 1.0 equiv) in DMF (4.25 L, 5 v/w) to give a clear solution, was added 4-dimethylaminopyridine (DMAP 116 g, 0.95 mol, 0.5 equiv) and 1-ethyl-3-(3-dimethylaminopropyl)carbodiimide (EDCI, 36.5 g, 0.19 mol, 0.1 equiv). After the mixture was stirred at 15 to 22° C. for about 1 hour, additional EDCI (36.5 g, 0.19 mol, 0.1 equiv) was added and stirred for another 1 hour. HPLC indicated a 69:1 trans/cis mixture. The product 3-10-trans was not isolated and was converted to compound I-1 in one-pot. $^1$H NMR (300 MHz, DMSO d$_6$): δ 1.47-1.55 (m, 1H), 1.63-1.68 (m, 1H), 1.81-1.87 (m, 1H), 1.90-1.97 (m, 1H), 2.93-3.19 (m, 1H), 3.16-3.23 (m, 1H), 3.33-3.45 (m, 2H) 4.07-4.33 (m, 3H), 6.80 (m, 1H), 6.94-6.98 (m, 1H), 7.10-7.16 (m, 2H), 7.91 (s, 1H).

(3R,3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxamide (I-1)

To the above reaction mixture, was charged at 22° C., with O-(7-azabenzotriazol-1-yl)-N,N,N',N'-tetramethyluronium hexafluorophosphate (HATU, 600 g, 1.9 mol, 1.0 equiv), N,N-diisopropylethylamine (DIPEA, 1.0 kg, 9.5 mol, 5.0 equiv) and finally NH$_4$Cl (260 g, 5.7 mol, 3.0 equiv). The resulting mixture was stirred at 15° C. for 1 hour, HPLC indicated complete consumption of 3-10-trans, the mixture was poured into brine (25 L) and extracted with EtOAc (2×2 L). The combined organics were washed with brine (2×2 L) and concentrated in vacuo below 45° C. to dryness to result in a crude I-1, which was purified by chromatograph with EtOAc/petroleum ether/MeOH (1:1:0 to 50:50:10) to give three fractions, which contained 316 g, 98.8% chemical purity and 10.8% epimer, 160 g, 82.3% chemical purity and 17.5% epimer and 180 g, 61% purity and 11.3% epimer, respectively. The above first two fractions were combined and further purified by prep-HPLC to give 200 g product with >99% purity and <1% epimer. $^1$H NMR (400 MHz, DMSO d$_6$): δ 1.48-1.53 (m, 1H), 1.66-1.69 (m, 1H), 1.77-1.79 (m, 3H), 2.11-2.16 (m, 1H), 2.80-2.88 (m, 2H), 3.11 (s, 1H), 3.42-3.48 (m, 1H), 4.0-4.25 (m, 4H), 6.58 (s, 3H), 6.80-6.85 (d, J=10.2, 2H), 6.95 (s, 2H), 7.40 (s, 1H), 7.77 (s, 1H).

Example 4

Alternative Syntheses of (3R,3'R,4'S)-1'-(6-amino-5-fluoropyrimidin-4-yl)-3-((3-chloro-5-(trifluoromethyl) phenyl)amino)-2-oxo-[1,3'-bipiperidine]-4'-carboxamide In addition to the methods described in Examples 2 and 3, (3R,3'R,4'S)-1'-(6-amino-5-fluoropyrimidin-4-yl)-3-((3-chloro-5-(trifluoromethyl) phenyl)amino)-2-oxo-[1,3'-bipiperidine]-4'-carboxamide (compound I-1) was also synthesized according to Scheme 6.

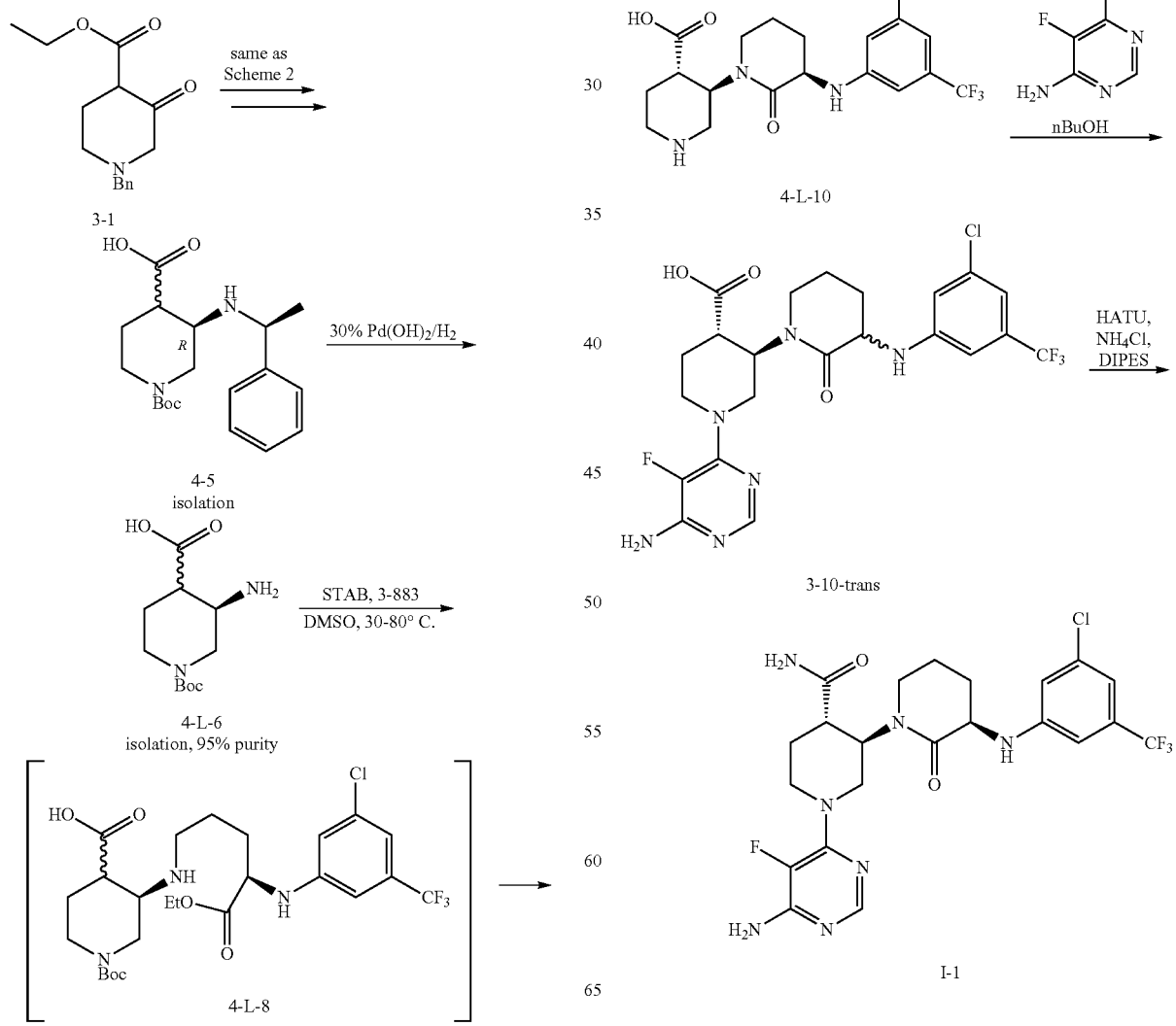

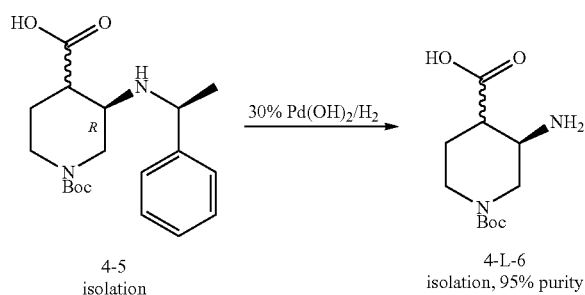

4-5
isolation

4-L-6
isolation, 95% purity

(3R)-3-amino-1-(tert-butoxycarbonyl)piperidine-4-carboxylic acid (4-L-6)

To a 10 L reactor charged under nitrogen with compound 4-5 (100 g, 0.287 mole), MeOH (6 L, 60 v/w) and 10 g 20% Pd(OH)$_2$/C. The reactor was evacuated/refilled with hydrogen three times and the mixture was warmed to 40-50° C. while stirring under 3 Mpa of hydrogen for 40 hours. LC/MS indicated complete consumption of starting material 4-5. The mixture was cooled to 22° C. and filtered, and the filtrate was concentrated in vacuo to dryness to afford a solid product. This crude product was slurried in EtOH (500 mL) at 22° C. for 2 hours, filtered and dried under vacuum at 50° C. to afford a 85% yield of product 4-L-6 (60 g, 0.245 mole) as a white solid.

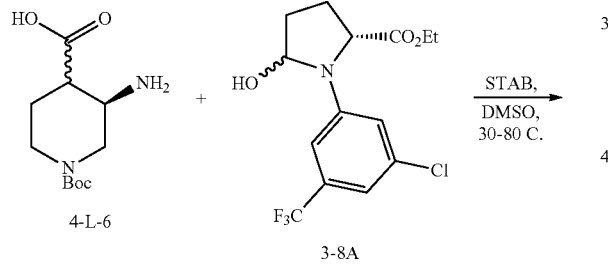

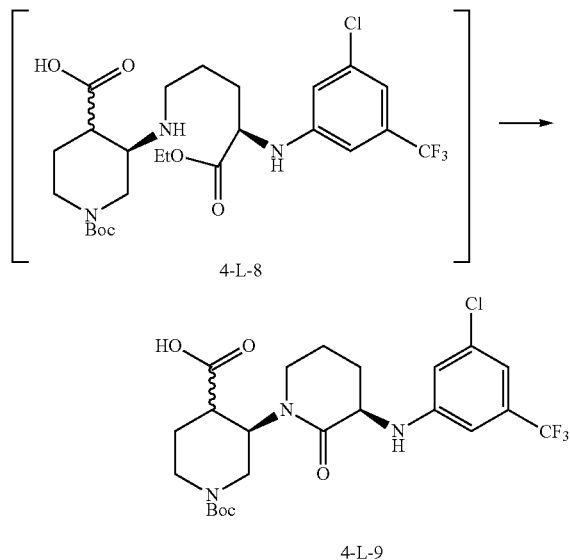

(3R)-1-(tert-butoxycarbonyl)-3-(((R)-4-((3-chloro-5-(trifluoromethyl)phenyl)amino)-5-ethoxy-5-oxopentyl)amino)piperidine-4-carboxylic acid (4-L-8)

To a solution of 4-L-6 (48.4 g, 0.197 mole) in DMSO (450 mL) was added Et$_3$N (20.2 g, 0.199 mole, 1 equiv), 3-8A (67.4 g, 0.199 mole, 1 equiv) and sodium triacetoxyborohydride (STAB, 84.8 g, 0.40 mole, 2.0 equiv). The mixture was heated to 50° C. over 30 min and stirred at that temperature for 3 hours. LC/MS indicated consumption of most of starting material 4-L-6 and formation of 4-L-8.

The reaction was quenched by adding EtOH (35 mL) and stirring at 50° C. for 30 min. The mixture was heated at 75-85° C. for 3 days. The mixture was cooled to 18° C. and transferred slowly into water (6 L) while vigorously stirring to afford a slurry. After 2 hours, the solids were filtered and washed with water (3×3 L), dried under vacuum at 60-70° C. for 24 hours to give 4-L-9 (114 g) as a brown solid. The solid was used directly in the subsequent step.

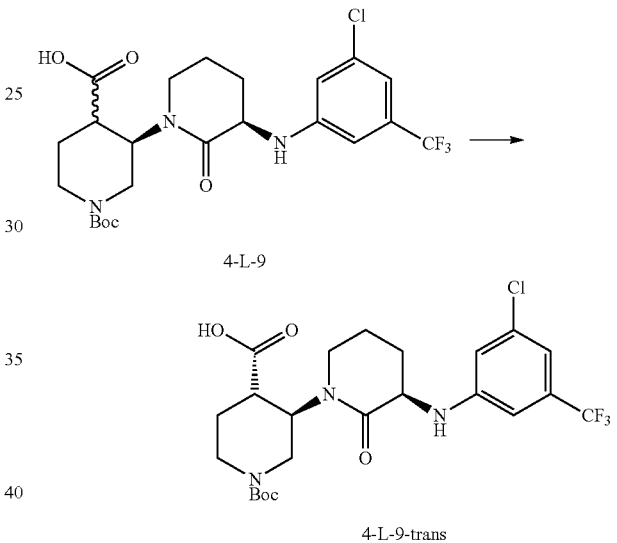

4-L-9

4-L-9-trans

(3R,3'R,4'S)-1'-(tert-butoxycarbonyl)-3-((3-chloro-5-(trifluoromethyl)phenyl)amino)-2-oxo-[1,3'-bipiperidine]-4'-carboxylic acid (4-L-9-trans)

To a solution of crude 4-L-9 (100 g), in DMF (500 mL) was added 4-dimethylaminopyridine (11 g, 0.09 mole, 0.5 equiv) and stirred at 20° C. for 10 min. 1-Ethyl-3-(3-dimethylaminopropyl)carbodiimide (7.0 g, 0.036 mole, 0.2 equiv) was added and the reaction was stirred 20 OC for 3 hours. HPLC indicated a ratio of 57:43 cis/trans mixture and additional EDAC (3.5 g, 0.018 mole, 0.1 equiv) was added. After 5 hours, HPLC indicated complete conversion to 4-L-9-trans. The mixture was transferred to water (2.25 L) slowly and the mixture was extracted with EtOAc (2×500 mL), and the organic layers were washed with brine (500 mL) and water (500 mL), concentrated in vacuo to dryness to give crude 4-L-9-trans (100 g) as a brown solid. The crude was dissolved in EtOAc (135 mL) at 60° C. and then cooled to 20° C. over 1 hour followed by adding 50 mL petroleum ether. The mixture was aged for 2 hours. The solids were filtered and washed with 3:1 EtOAc/petroleum ether (50 mL), dried under vacuum at 50° C. for 16 hours to give 4-L-9-trans (23 g, 22% yield with 99% purity). $^1$H NMR (400 MHz, DMSO-d$_6$) δ 6.94 (s, 2H), 6.81 (s, 1H), 6.54-6.61 (m, 1H), 3.99-4.08 (m, 1H), 3.42-3.38 (m, 2H), 2.07-2.16 (m, 1H), 1.74-1.92 (m, 3H), 1.39 (s, 9H).

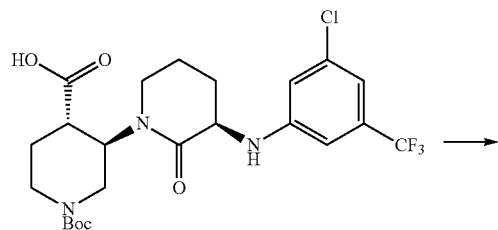

4-L-9 trans

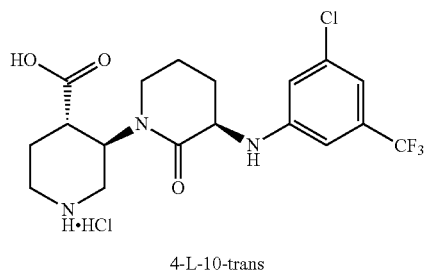

4-L-10-trans (3R,3'R,4'S)-3-((3-chloro-5-(trifluoromethyl)phenyl) amino)-2-oxo-[1,3'-bipiperidine]-4'-carboxylic acid hydrochloride (4-L-10 trans). To a solution of 0.5N HCl in EtOAc (76 mL) was added 4-L-9 trans (20 g, 38 mmol) and heated at 20° C. for 18 h to give a slurry. The solid was filtered, washed with EtOAc (5 mL) and dried under vacuum at 45° C. for 18 h to afford 4-L-10 as the HCl salt (17 g, 97% yield).

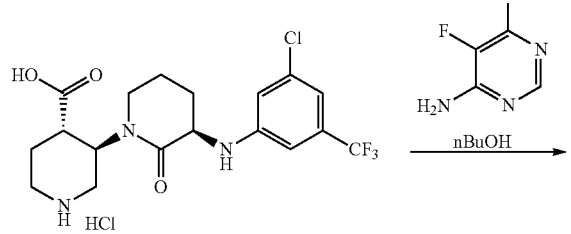

4-L-10

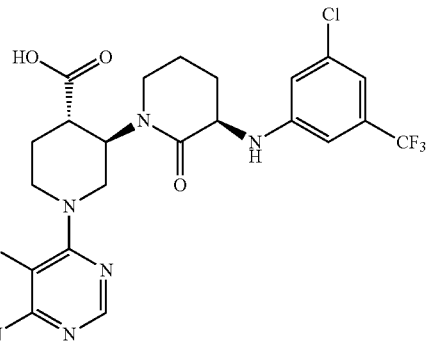

3-10-trans (3R,3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxylic acid (3-10-trans). A solution of 4-L-10 (2.0 g, 4.38 mole), 6-chloro-5-fluoro-pyrimidin-4-ylamine (711 mg, 4.82 mmole, 1.1 equiv), DIPEA (1.52 mL, 8.77 mole, 2 eq.) in 40 mL nBuOH was heated to 130-140° C. for 72 h. The mixture was cooled to 22° C. and concentrated in vacuo to afford a residue which purified by column to give 3-10-trans (1.1 g, 47%). A relatively minor amount of epimer (3 S,3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxylic acid was also observed. Intermediate 3-10-trans can be converted to compound I-1 via procedure described above.

Compound I-1 was also synthesized according to Scheme 8.

Scheme 8

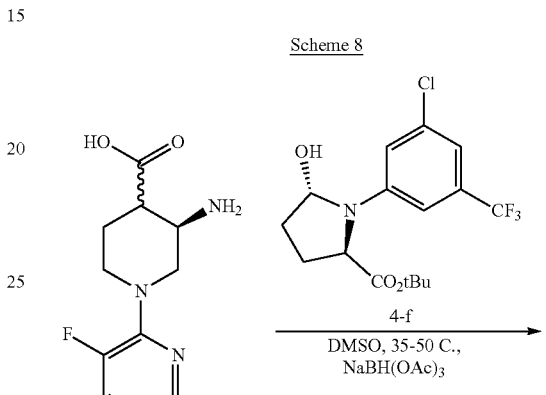

3-8

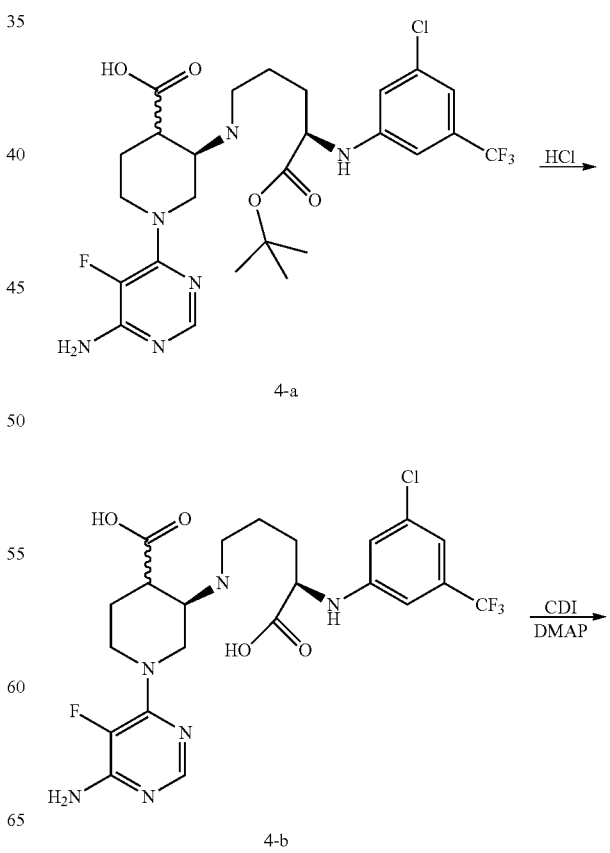

4-a 4-b

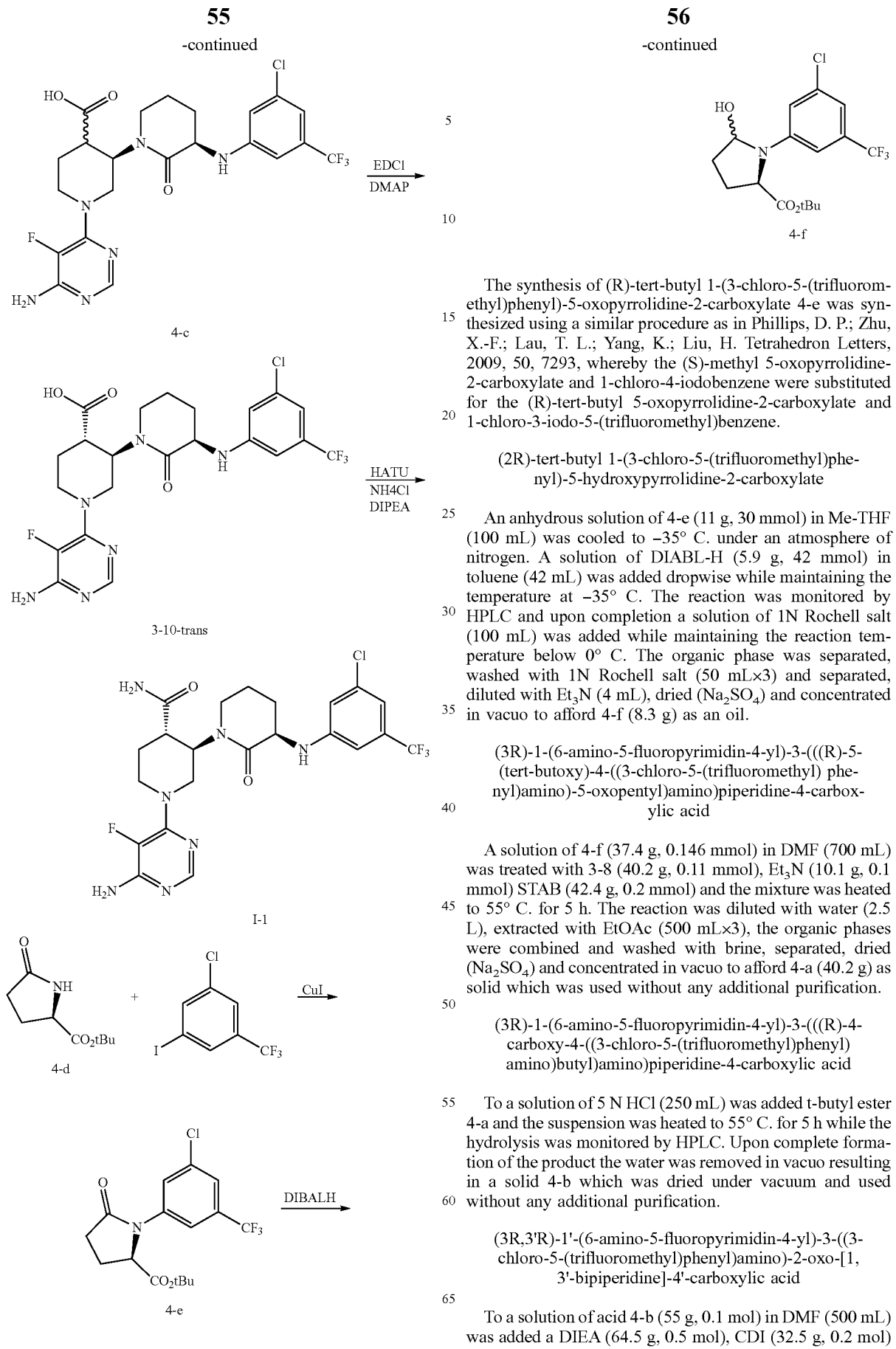

The synthesis of (R)-tert-butyl 1-(3-chloro-5-(trifluoromethyl)phenyl)-5-oxopyrrolidine-2-carboxylate 4-e was synthesized using a similar procedure as in Phillips, D. P.; Zhu, X.-F.; Lau, T. L.; Yang, K.; Liu, H. Tetrahedron Letters, 2009, 50, 7293, whereby the (S)-methyl 5-oxopyrrolidine-2-carboxylate and 1-chloro-4-iodobenzene were substituted for the (R)-tert-butyl 5-oxopyrrolidine-2-carboxylate and 1-chloro-3-iodo-5-(trifluoromethyl)benzene.

(2R)-tert-butyl 1-(3-chloro-5-(trifluoromethyl)phenyl)-5-hydroxypyrrolidine-2-carboxylate An anhydrous solution of 4-e (11 g, 30 mmol) in Me-THF (100 mL) was cooled to −35° C. under an atmosphere of nitrogen. A solution of DIABL-H (5.9 g, 42 mmol) in toluene (42 mL) was added dropwise while maintaining the temperature at −35° C. The reaction was monitored by HPLC and upon completion a solution of 1N Rochell salt (100 mL) was added while maintaining the reaction temperature below 0° C. The organic phase was separated, washed with 1N Rochell salt (50 mL×3) and separated, diluted with Et$_3$N (4 mL), dried (Na$_2$SO$_4$) and concentrated in vacuo to afford 4-f (8.3 g) as an oil.

(3R)-1-(6-amino-5-fluoropyrimidin-4-yl)-3-(((R)-5-(tert-butoxy)-4-((3-chloro-5-(trifluoromethyl) phenyl)amino)-5-oxopentyl)amino)piperidine-4-carboxylic acid A solution of 4-f (37.4 g, 0.146 mmol) in DMF (700 mL) was treated with 3-8 (40.2 g, 0.11 mmol), Et$_3$N (10.1 g, 0.1 mmol) STAB (42.4 g, 0.2 mmol) and the mixture was heated to 55° C. for 5 h. The reaction was diluted with water (2.5 L), extracted with EtOAc (500 mL×3), the organic phases were combined and washed with brine, separated, dried (Na$_2$SO$_4$) and concentrated in vacuo to afford 4-a (40.2 g) as solid which was used without any additional purification.

(3R)-1-(6-amino-5-fluoropyrimidin-4-yl)-3-(((R)-4-carboxy-4-((3-chloro-5-(trifluoromethyl)phenyl) amino)butyl)amino)piperidine-4-carboxylic acid To a solution of 5 N HCl (250 mL) was added t-butyl ester 4-a and the suspension was heated to 55° C. for 5 h while the hydrolysis was monitored by HPLC. Upon complete formation of the product the water was removed in vacuo resulting in a solid 4-b which was dried under vacuum and used without any additional purification.

(3R,3'R)-1'-(6-amino-5-fluoropyrimidin-4-yl)-3-((3-chloro-5-(trifluoromethyl)phenyl)amino)-2-oxo-[1,3'-bipiperidine]-4'-carboxylic acid To a solution of acid 4-b (55 g, 0.1 mol) in DMF (500 mL) was added a DIEA (64.5 g, 0.5 mol), CDI (32.5 g, 0.2 mol)

at 0° C. The solution was stirred for 1.5 h at 0° C., diluted with water (3 L), adjusted to a pH 3 with HCl and extracted with EtOAc (2 L×3). The organic phase were combined, dried (Na₂SO₄) and concentrated in vacuo to afford 4-c (48 g).

The remaining steps to compound I-1 are completed via procedures described above.

Example 5

Synthesis of trans-tert-butyl 3-((3-chloro-5-(trifluoromethyl)phenyl) amino)-4'-(methylcarbamoyl)-2-oxo-[1,3'-bipiperidine]-1'-carboxylate Synthesis of trans-tert-butyl 3-((3-chloro-5-(trifluoromethyl)phenyl) amino)-4'-(methylcarbamoyl)-2-oxo-[1,3'-bipiperidine]-1'-carboxylate A similar procedure was used as described for the synthesis of (3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxamide 14 to afford the crude material which was purified by pre-HPLC (MeOH/H₂O with 0.05% NH₃.H₂O as mobile phase) to give the title compound (360 mg, yield: 67%) as a yellow solid. ESI-MS (M+H)⁺: 544.18. HPLC: (214 nm: 100.0%, 254 nm: 100.0%). ¹H NMR (400 MHz, CD₃OD) (mixture of isomers) δ: 7.69-7.68 (m, 1H), 6.78 (s, 1H), 6.75 (s, 1H), 6.71 (s, 1H), 4.39-4.36 (m, 2H), 4.09-4.03 (m, 1H), 3.53-3.31 (m, 3H), 3.20-3.10 (m, 1H), 2.99-2.92 (m, 1H), 2.55 (s, 3H), 2.28-2.19 (m, 1H), 1.96-1.77 (m, 5H), 1.68-1.58 (m, 1H).

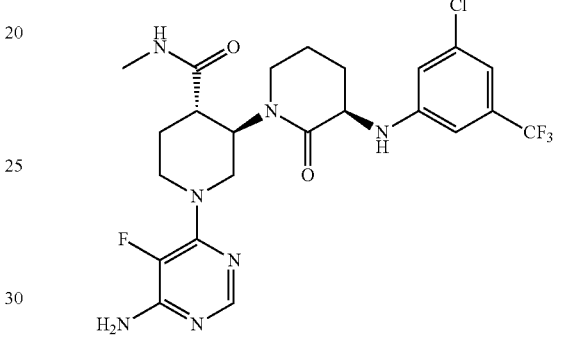

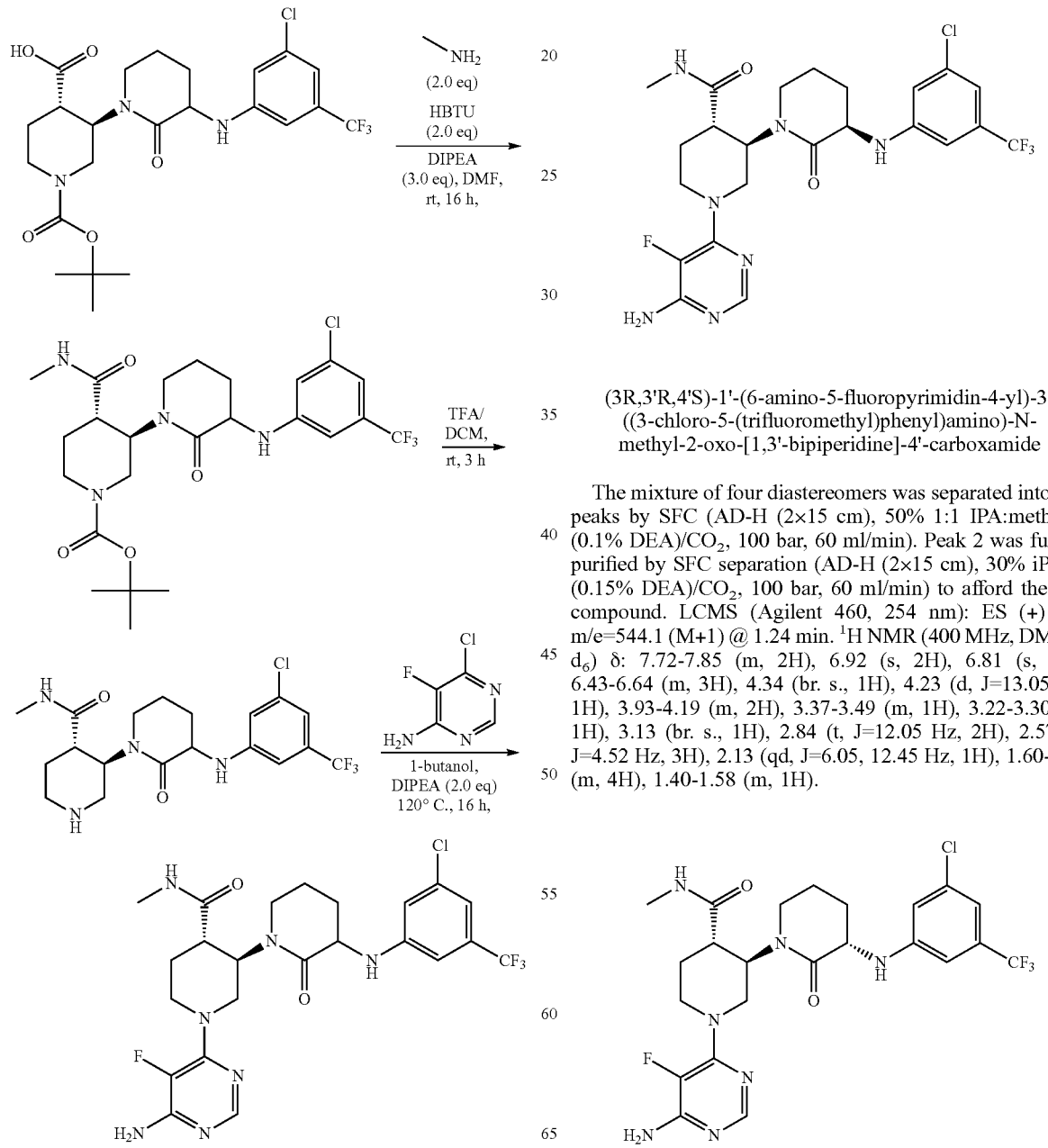

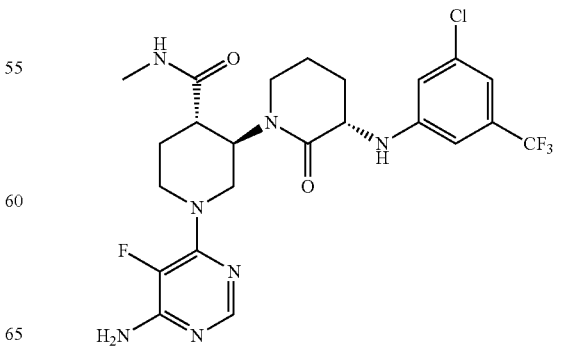

(3R,3'R,4'S)-1'-(6-amino-5-fluoropyrimidin-4-yl)-3-((3-chloro-5-(trifluoromethyl)phenyl)amino)-N-methyl-2-oxo-[1,3'-bipiperidine]-4'-carboxamide The mixture of four diastereomers was separated into two peaks by SFC (AD-H (2×15 cm), 50% 1:1 IPA:methanol (0.1% DEA)/CO₂, 100 bar, 60 ml/min). Peak 2 was further purified by SFC separation (AD-H (2×15 cm), 30% iPrOH (0.15% DEA)/CO₂, 100 bar, 60 ml/min) to afford the title compound. LCMS (Agilent 460, 254 nm): ES (+) MS m/e=544.1 (M+1) @ 1.24 min. ¹H NMR (400 MHz, DMSO-d₆) δ: 7.72-7.85 (m, 2H), 6.92 (s, 2H), 6.81 (s, 1H), 6.43-6.64 (m, 3H), 4.34 (br. s., 1H), 4.23 (d, J=13.05 Hz, 1H), 3.93-4.19 (m, 2H), 3.37-3.49 (m, 1H), 3.22-3.30 (m, 1H), 3.13 (br. s., 1H), 2.84 (t, J=12.05 Hz, 2H), 2.57 (d, J=4.52 Hz, 3H), 2.13 (qd, J=6.05, 12.45 Hz, 1H), 1.60-1.89 (m, 4H), 1.40-1.58 (m, 1H).

(3S,3'R,4'S)-1'-(6-amino-5-fluoropyrimidin-4-yl)-3-((3-chloro-5-(trifluoromethyl)phenyl)amino)-N-methyl-2-oxo-[1,3'-bipiperidine]-4'-carboxamide The mixture of four diastereomers was separated into two peaks by SFC (AD-H (2×15 cm), 50% 1:1 IPA:methanol (0.1% DEA)/CO$_2$, 100 bar, 60 ml/min). Peak 2 was further purified by SFC separation (AD-H (2×15 cm), 30% iPrOH (0.15% DEA)/CO$_2$, 100 bar, 60 ml/min) to afford the title compound. LCMS (Agilent 460, 254 nm): ES (+) MS m/e=544.1 (M+1) @ 1.24 min. $^1$H NMR (400 MHz, DMSO-d$_6$) δ: 7.83 (q, J=4.60 Hz, 1H), 7.77 (d, J=1.76 Hz, 1H), 6.97 (d, J=6.78 Hz, 2H), 6.81 (s, 1H), 6.58 (s, 2H), 6.53 (d, J=7.78 Hz, 1H), 4.23 (d, J=13.05 Hz, 2H), 3.90-4.19 (m, 2H), 3.14 (br. s., 1H), 2.92 (br. s., 1H), 2.74-2.90 (m, 1H), 2.55 (d, J=4.52 Hz, 3H), 2.00-2.18 (m, 1H), 1.74-1.89 (m, 3H), 1.56-1.74 (m, 1H), 1.34-1.50 (m, 1H).

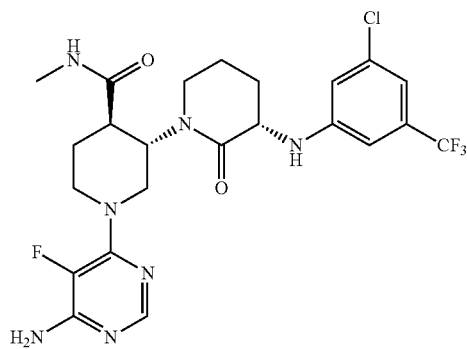

(3S,3'S,4'R)-1'-(6-amino-5-fluoropyrimidin-4-yl)-3-((3-chloro-5-(trifluoromethyl)phenyl)amino)-N-methyl-2-oxo-[1,3'-bipiperidine]-4'-carboxamide The mixture of four diastereomers was separated into two peaks by SFC (AD-H (2×15 cm), 50% 1:1 IPA:methanol (0.1% DEA)/CO$_2$, 100 bar, 60 ml/min). Peak 1 was further purified by SFC (AD-H (2×15 cm), 30% MeOH (0.15% DEA)/CO$_2$, 100 bar, 60 ml/min) to afford the titled compound. LCMS (Agilent 460, 254 nm): ES (+) MS m/e=544.1 (M+1) @ 1.23 min. $^1$H NMR (400 MHz, DMSO-d$_6$) δ: 7.72-7.85 (m, 2H), 6.92 (s, 2H), 6.81 (s, 1H), 6.57 (s, 2H), 6.54 (d, J=7.53 Hz, 1H), 4.23 (d, J=13.30 Hz, 1H), 4.15 (dd, J=3.26, 12.30 Hz, 1H), 4.08 (td, J=7.06, 10.48 Hz, 1H), 3.36-3.47 (m, 1H), 3.23-3.30 (m, 1H), 3.13 (br. s., 1H), 2.84 (t, J=11.80 Hz, 2H), 2.57 (d, J=4.52 Hz, 3H), 2.13 (qd, J=6.17, 12.61 Hz, 1H), 1.62-1.91 (m, 4H), 1.42-1.57 (m, 1H).

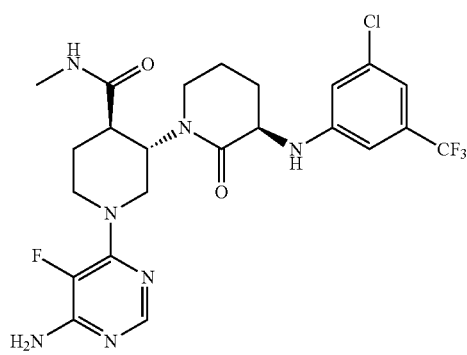 [SMILES: CNC(=O)[C@@H]1CCN(c2ncnc(N)c2F)C[C@H]1N1CCC[C@@H](Nc2cc(Cl)cc(C(F)(F)F)c2)C1=O]

trans-1'-(6-amino-5-fluoropyrimidin-4-yl)-3-((3-chloro-5-(trifluoromethyl)phenyl)amino)-N-methyl-2-oxo-[1,3'-bipiperidine]-4'-carboxamide The mixture of four diastereomers was separated into two peaks by SFC (AD-H (2×15 cm), 50% 1:1 IPA:methanol (0.1% DEA)/CO$_2$, 100 bar, 60 ml/min). Peak 1 was further purified by SFC (AD-H (2×15 cm), 30% MeOH (0.15% DEA)/CO$_2$, 100 bar, 60 ml/min) to afford the titled cmpd. LCMS (Agilent 460, 254 nm): ES (+) MS m/e=544.1 (M+1) @ 1.23 min. LCMS (Agilent 460, 254 nm): ES (+) MS m/e=544.1 (M+1) @ 1.24 min. $^1$H NMR (400 MHz, DMSO-d$_6$) δ: 7.80-7.89 (m, 1H), 7.72-7.80 (m, 1H), 6.97 (d, J=6.53 Hz, 2H), 6.81 (s, 1H), 6.58 (s, 2H), 6.53 (d, J=7.78 Hz, 1H), 4.23 (d, J=13.05 Hz, 2H), 3.89-4.19 (m, 2H), 3.13 (br. s., 1H), 2.74-3.02 (m, J=12.42, 12.42 Hz, 2H), 2.55 (d, J=4.52 Hz, 3H), 2.08 (qd, J=5.97, 12.20 Hz, 1H), 1.81 (td, J=6.24, 12.36 Hz, 3H), 1.56-1.74 (m, 1H), 1.33-1.51 (m, 1H).

Example 6

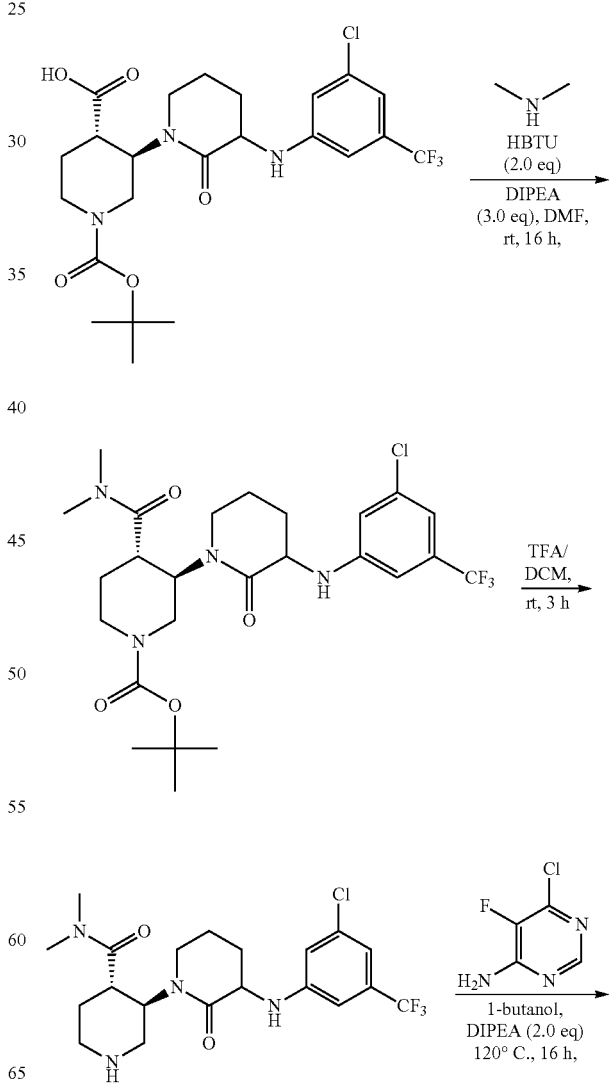

-continued

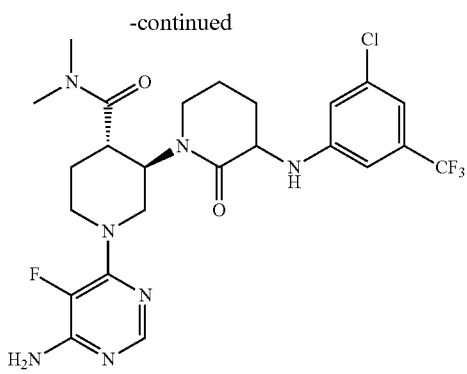

Synthesis of trans-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide A similar procedure was used as described for the synthesis of (3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxamide 14 to afford the crude material which was purified by pre-HPLC (MeOH/H$_2$O with 0.05% TFA as mobile phase) to give the title compound (45 mg, yield: 90%) as a yellow solid. ESI-MS (M+H)$^+$: 558.0. HPLC: (214 nm: 98.2%, 254 nm: 100.0%). $^1$H NMR (400 MHz, CD$_3$OD) δ: 7.77 (s, 1H), 6.92-6.89 (m, 1H), 6.83-6.81 (m, 1H), 6.79 (s, 1H), 4.38-4.38 (m, 2H), 4.05-4.00 (m, 2H), 3.55-3.53 (m, 1H), 3.45-3.40 (m, 2H), 3.15-2.89 (m, 7H), 2.21-2.16 (m, 1H), 1.90-1.86 (m, 3H), 1.66-1.56 (m, 2H).

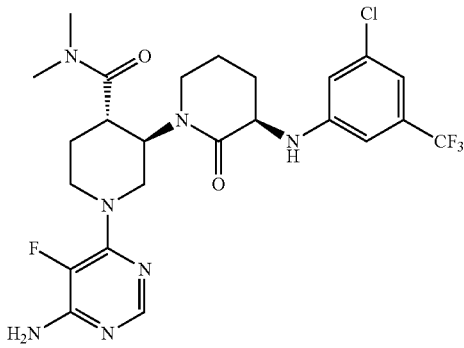 [SMILES: CN(C)C(=O)[C@H]1CCN(c2ncnc(N)c2F)C[C@@H]1N1CCC[C@@H](Nc2cc(Cl)cc(C(F)(F)F)c2)C1=O]

(3R,3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide The title compound was obtained from chiral separation of trans-1'-(6-amino-5-fluoropyrimidin-4-yl)-3-((3-chloro-5-(trifluoromethyl)phenyl) amino)-N,N-dimethyl-2-oxo-[1, 3'-bipiperidine]-4'-carboxamide using a two step chiral SFC separation. Firstly, the mixture was separated into two peaks containing a mixture of two diastereomers ((3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide and (3'S,4'R)-1'-(6-amino-5-fluoropyrimidin-4-yl)-3-((3-chloro-5 (trifluoromethyl) phenyl)amino)-N,N-dimethyl-2-oxo-[1,3'-bipiperidine]-4'-carb oxamide) using a ChiralPak IC (2×15 cm, 30% methanol w/0.1 DEA) column, and then the resulting mixture containing a pair of isomers was further separated into the single enantiomers using a ChiralPak IA (2×15 cm, 30% methanol w/0.1% DEA 100 bar) column. ESI-MS (M+H)$^+$: 558.0. $^1$H NMR (400 MHz, CDCl$_3$) δ: 7.92 (d, J=1.76 Hz, 1H), 6.94 (s, 1H), 6.72 (d, J=7.78 Hz, 2H), 5.21 (d, J=3.51 Hz, 1H), 4.70 (s, 2H), 4.45 (dd, J=2.76, 12.80 Hz, 2H), 4.17-4.32 (m, 1H), 3.64-3.80 (m, 2H), 3.44-3.58 (s, 3H), 3.09 (s, 3H), 3.00-3.09 (m, 1H), 2.95 (s, 3H), 2.40 (dd, J=5.52, 13.30 Hz, 1H), 1.63-1.99 (m, 3H), 1.26-1.43 (m, 1H).

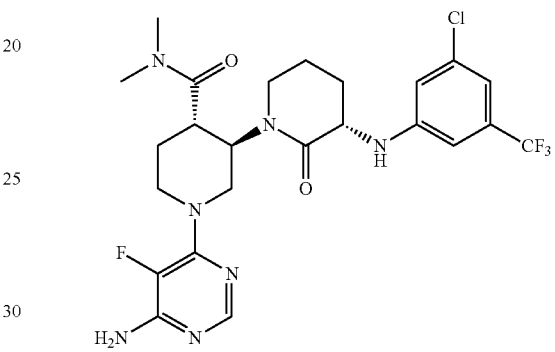

(3S,3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide The title compound was obtained from chiral separation of trans-1'-(6-amino-5-fluoropyrimidin-4-yl)-3-((3-chloro-5-(trifluoromethyl)phenyl) amino)-N,N-dimethyl-2-oxo-[1, 3'-bipiperidine]-4'-carboxamide using a two step chiral SFC separation. Firstly, the mixture was separated into two peaks containing a mixture of two diastereomers ((3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide and (3'S,4'R)-1'-(6-amino-5-fluoropyrimidin-4-yl)-3-((3-chloro-5 (trifluoromethyl) phenyl)amino)-N,N-dimethyl-2-oxo-[1,3'-bipiperidine]-4'-carb oxamide) using a ChiralPak IC (2×15 cm, 30% methanol w/0.1 DEA) column, and then the resulting mixture containing a pair of isomers was further separated into the single enantiomers using a ChiralPak IA (2×15 cm, 30% methanol w/0.1% DEA 100 bar) column. ESI-MS (M+H)$^+$: 558.0 $^1$H NMR (400 MHz, (400 MHz, CDCl$_3$) δ: 7.93 (d, J=1.26 Hz, 1H), 6.93 (s, 1H), 6.69 (br. s., 2H), 5.06 (d, J=4.27 Hz, 1H), 4.71 (s, 1H), 4.45 (d, J=12.55 Hz, 2H), 4.16-4.26 (m, 1H), 3.66-3.81 (m, 2H), 3.54-3.64 (m, 1H), 3.40-3.54 (m, 2H), 3.01-3.10 (m, 4H), 2.95 (s, 3H), 2.37 (dd, J=5.27, 13.05 Hz, 1H), 1.91-2.02 (m, 2H), 1.48-1.75 (m, 2H).

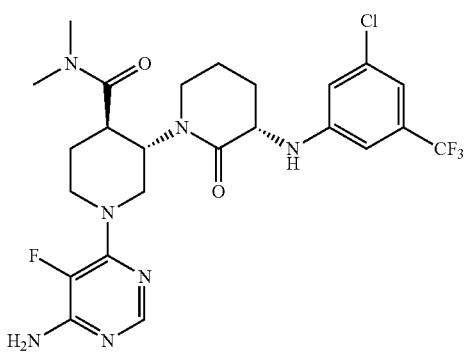 [SMILES: CN(C)C(=O)[C@@H]1CCN(c2ncnc(N)c2F)C[C@H]1N1CCC[C@H](Nc2cc(Cl)cc(C(F)(F)F)c2)C1=O]

(3S,3'S,4'R)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide The title compound was obtained from chiral separation of trans-1'-(6-amino-5-fluoropyrimidin-4-yl)-3-((3-chloro-5-(trifluoromethyl)phenyl) amino)-N,N-dimethyl-2-oxo-[1,3'-bipiperidine]-4'-carboxamide using a two step chiral SFC separation. Firstly, the mixture was separated into two peaks containing a mixture of two diastereomers ((3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide and (3'S,4'R)-1'-(6-amino-5-fluoropyrimidin-4-yl)-3-((3-chloro-5-(trifluoromethyl) phenyl)amino)-N,N-dimethyl-2-oxo-[1,3'-bipiperidine]-4'-carb oxamide) using a ChiralPak IC (2×15 cm, 30% methanol w/0.1 DEA) column, and then the resulting mixture containing a pair of isomers was further separated into the single enantiomers using a ChiralPak IA (2×15 cm, 30% methanol w/0.1% DEA 100 bar) column. ESI-MS (M+H)+: 558.0 1H NMR (400 MHz, CDCl3) δ: 7.92 (d, J=1.76 Hz, 1H), 6.94 (s, 1H), 6.72 (d, J=7.78 Hz, 2H), 5.21 (d, J=3.51 Hz, 1H), 4.70 (s, 2H), 4.45 (dd, J=2.76, 12.80 Hz, 2H), 4.19-4.30 (m, 1H), 3.66-3.79 (m, 2H), 3.47-3.56 (m, 3H), 3.09 (s, 3H), 2.97-3.07 (m, 1H), 2.95 (s, 3H), 2.40 (dd, J=5.52, 13.30 Hz, 1H), 1.81-1.97 (m, 3H), 1.73 (dd, J=3.76, 12.80 Hz, 1H).

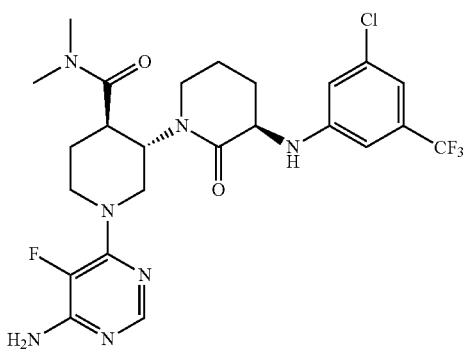 [SMILES: CN(C)C(=O)[C@@H]1CCN(c2ncnc(N)c2F)C[C@H]1N1CCC[C@@H](Nc2cc(Cl)cc(C(F)(F)F)c2)C1=O]

(3R,3'S,4'R)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide The title compound was obtained from chiral separation of trans-1'-(6-amino-5-fluoropyrimidin-4-yl)-3-((3-chloro-5-(trifluoromethyl)phenyl) amino)-N,N-dimethyl-2-oxo-[1, 3'-bipiperidine]-4'-carboxamide using a two step chiral SFC separation. Firstly, the mixture was separated into two peaks containing a mixture of two diastereomers ((3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide and (3'S,4'R)-1'-(6-amino-5-fluoropyrimidin-4-yl)-3-((3-chloro-5 (trifluoromethyl) phenyl)amino)-N,N-dimethyl-2-oxo-[1,3'-bipiperidine]-4'-carb oxamide) using a ChiralPak IC (2×15 cm, 30% methanol w/0.1 DEA) column, and then each mixture containing a pair of isomers was further separated into the single enantiomers using a ChiralPak IA (2×15 cm, 30% methanol w/0.1% DEA 100 bar) column. ESI-MS (M+H)+: 558.0 1H NMR (400 MHz, (400 MHz, CDCl3) δ: 7.93 (d, J=1.26 Hz, 1H), 6.93 (s, 1H), 6.69 (br. s., 2H), 5.06 (d, J=4.27 Hz, 1H), 4.71 (s, 1H), 4.45 (d, J=12.55 Hz, 2H), 4.16-4.26 (m, 1H), 3.66-3.81 (m, 2H), 3.54-3.64 (m, 1H), 3.40-3.54 (m, 2H), 3.01-3.10 (m, 4H), 2.95 (s, 3H), 2.37 (dd, J=5.27, 13.05 Hz, 1H), 1.91-2.02 (m, 2H), 1.48-1.75 (m, 2H).

Example 7

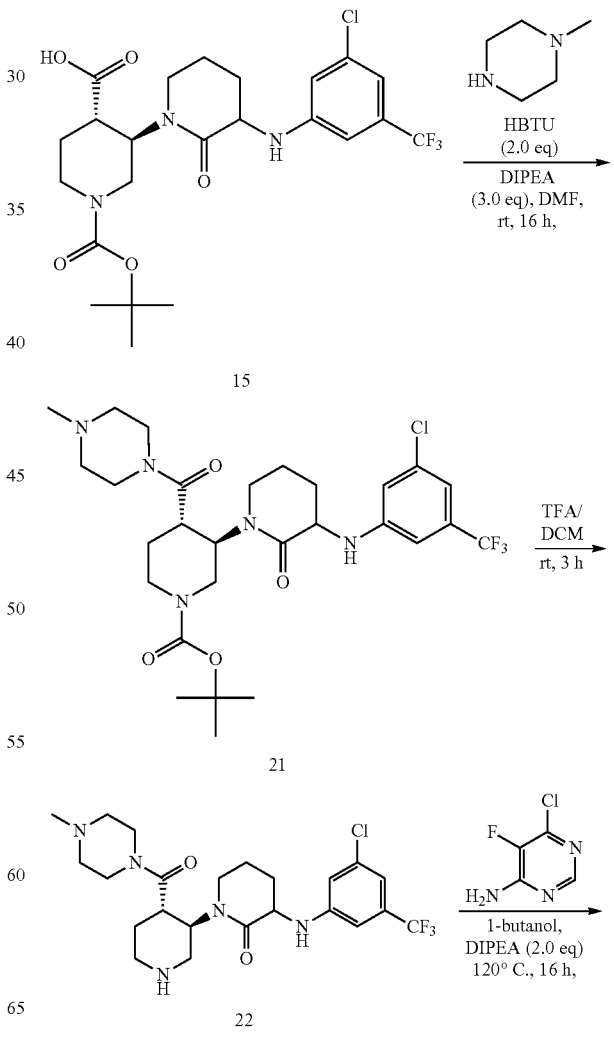

-continued

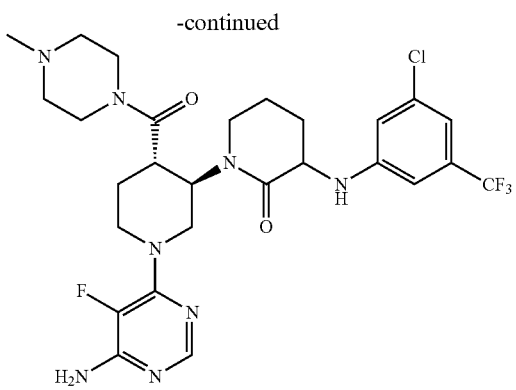

23

Synthesis of trans-1'-(6-amino-5-fluoropyrimidin-4-yl)-3-((3-chloro-5-(trifluoromethyl)phenyl)amino)-4'-(4-methylpiperazine-1-carbonyl)-[1,3'-bipiperidin]-2-one A similar procedure was used as described for the synthesis of trans-1'-(6-amino-5-fluoropyrimidin-4-yl)-3-((3-chloro-5-(trifluoromethyl)phenyl)amino)-2-oxo-[1,3'-bipiperidine]-4'-carboxamide 14 to afford 23 which was purified by reverse phase HPLC (MeOH/H$_2$O with 0.05% NH$_3$.H$_2$O as mobile phase) to afford the title compound (100 mg, yield: 70%) as a yellow solid. ESI-MS (M+H)$^+$: 613.24. $^1$H NMR (400 MHz, CDCl$_3$) δ: 7.94 (s, 1H), 6.94 (s, 1H), 6.73-6.67 (m, 2H), 5.25-5.03 (m, 1H), 4.71 (s, 2H), 4.49-4.40 (m, 2H), 4.35-4.16 (m, 1H), 3.82-3.64 (m, 3H), 3.62-3.41 (m, 6H), 3.08-2.97 (m, 1H), 2.52-2.34 (m, 3H), 2.30-2.25 (m, 2H), 2.20 (s, 3H), 1.85-1.64 (m, 2H), 1.72-1.64 (m, 2H), 1.49-1.31 (m, 1H).

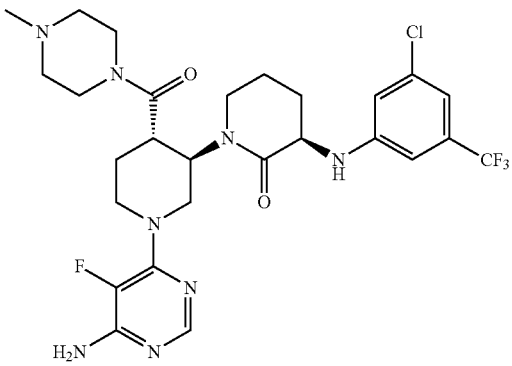 [SMILES: CN1CCN(C(=O)[C@H]2CCN(c3ncnc(N)c3F)C[C@@H]2N2CCC[C@@H](Nc3cc(Cl)cc(C(F)(F)F)c3)C2=O)CC1]

(3R,3'R,4'S)-1'-(6-amino-5-fluoropyrimidin-4-yl)-3-((3-chloro-5-(trifluoromethyl)phenyl)amino)-4'-(4-methylpiperazine-1-carbonyl)-[1,3'-bipiperidin]-2-one The title compound was obtained from chiral separation of trans-1'-(6-amino-5-fluoropyrimidin-4-yl)-3-((3-chloro-5-(trifluoromethyl)phenyl) amino)-N,N-dimethyl-2-oxo-[1,3'-bipiperidine]-4'-carboxamide 23 using a two step chiral SFC separation. Firstly, the mixture was separated into two peaks containing a mixture of two diastereomers ((3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide and (3'S,4'R)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carb oxamide) using a ChiralPak IC (2×15 cm, 30% methanol w/0.1 DEA) column, and then the resulting mixture containing a pair of isomers was further separated into the single enantiomers using a ChiralPak IA (2×15 cm, 30% methanol w/0.1% DEA 100 bar) column. ESI-MS (M+H)$^+$: 613.2 $^1$H NMR (400 MHz, CD$_3$OD) δ: 7.95 (s, 1H), 6.83-6.97 (m, 3H), 4.50-4.68 (m, 2H), 4.28-4.40 (m, 1H), 3.66-3.91 (m, 8H), 3.30-3.52 (m, 4H), 3.14 (t, J=12.42 Hz, 2H), 2.73 (br. s., 2H), 2.27 (dd, J=5.65, 12.93 Hz, 1H), 1.83-2.05 (m, 2H), 1.54-1.79 (m, 2H).

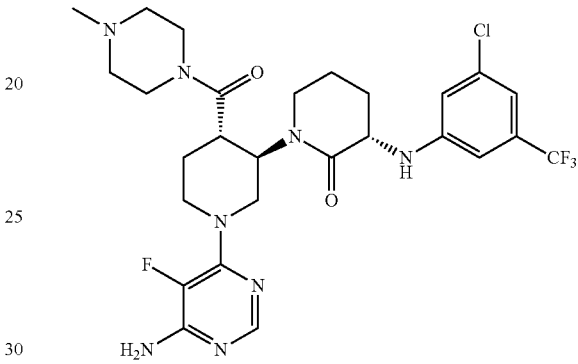

(3S,3'R,4'S)-1'-(6-amino-5-fluoropyrimidin-4-yl)-3-((3-chloro-5-(trifluoromethyl)phenyl)amino)-4'-(4-methylpiperazine-1-carbonyl)-[1,3'-bipiperidin]-2-one The title compound was obtained from chiral separation of trans-1'-(6-amino-5-fluoropyrimidin-4-yl)-3-((3-chloro-5-(trifluoromethyl)phenyl) amino)-N,N-dimethyl-2-oxo-[1,3'-bipiperidine]-4'-carboxamide 23 using a two step chiral SFC separation. Firstly, the mixture was separated into two peaks containing a mixture of two diastereomers ((3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide and (3'S,4'R)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carb oxamide) using a ChiralPak IC (2×15 cm, 30% methanol w/0.1 DEA) column, and then the resulting mixture containing a pair of isomers was further separated into the single enantiomers using a ChiralPak IA (2×15 cm, 30% methanol w/0.1% DEA 100 bar) column. ESI-MS (M+H)$^+$: 613.2. $^1$H NMR (400 MHz, CD$_3$OD) δ: 7.91-7.99 (m, 1H), 6.84-6.97 (m, 3H), 4.57 (dd, J=14.18, 19.70 Hz, 2H), 4.34 (br. s., 1H), 3.42-3.53 (m, 1H), 3.37 (d, J=1.51 Hz, 3H), 3.05-3.19 (m, 1H), 2.86 (t, J=7.53 Hz, 1H), 2.68-2.78 (m, 2H), 2.26 (dd, J=5.65, 12.93 Hz, 1H), 1.82-2.03 (m, 3H), 1.55-1.79 (m, 2H).

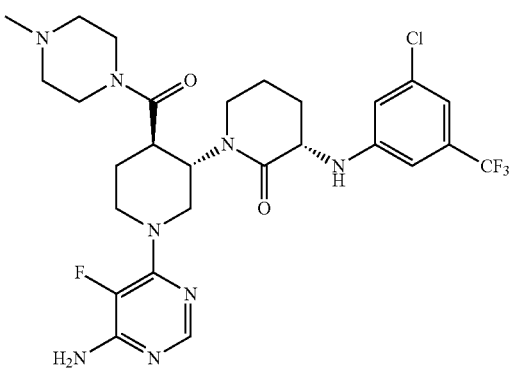 [SMILES: CN1CCN(C(=O)[C@@H]2CCN(c3ncnc(N)c3F)C[C@H]2N2CCC[C@H](Nc3cc(Cl)cc(C(F)(F)F)c3)C2=O)CC1]

(3S,3'S,4'R)-1'-(6-amino-5-fluoropyrimidin-4-yl)-3-((3-chloro-5-(trifluoromethyl)phenyl)amino)-4'-(4-methylpiperazine-1-carbonyl)-[1,3'-bipiperidin]-2-one The title compound was obtained from chiral separation of trans-1'-(6-amino-5-fluoropyrimidin-4-yl)-3-((3-chloro-5-(trifluoromethyl)phenyl) amino)-N,N-dimethyl-2-oxo-[1,3'-bipiperidine]-4'-carboxamide 23 using a two step chiral SFC separation. Firstly, the mixture was separated into two peaks containing a mixture of two diastereomers ((3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide and (3'S,4'R)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carb oxamide) using a ChiralPak IC (2×15 cm, 30% methanol w/0.1 DEA) column, and then the resulting mixture containing a pair of isomers was further separated into the single enantiomers using a ChiralPak IA (2×15 cm, 30% methanol w/0.1% DEA 100 bar) column. ESI-MS (M+H)⁺: 613.2. ¹H NMR (400 MHz, CD₃OD) δ: 7.94 (s, 1H), 6.87-6.93 (m, 3H), 4.57 (dd, J=14.18, 19.70 Hz, 1H), 4.34 (br. s., 1H), 3.43-3.51 (m, 1H), 3.36-3.38 (m, 2H), 3.13 (t, J=12.30 Hz, 1H), 2.86 (t, J=7.53 Hz, 1H), 2.73 (br. s., 1H), 2.26 (dd, J=5.65, 12.93 Hz, 1H), 1.96-2.03 (m, 1H), 1.83-1.94 (m, 1H), 1.51-1.75 (m, 1H).

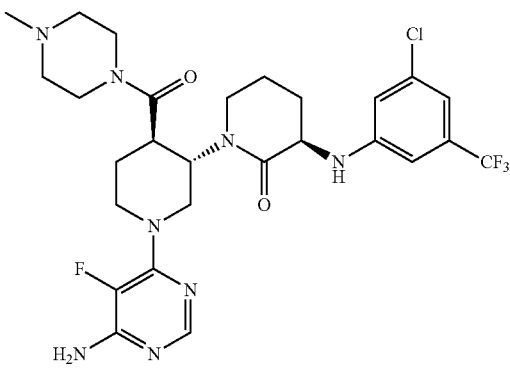 [SMILES: CN1CCN(C(=O)[C@@H]2CCN(c3ncnc(N)c3F)C[C@H]2N2CCC[C@@H](Nc3cc(Cl)cc(C(F)(F)F)c3)C2=O)CC1]

((3R,3'S,4'R)-1'-(6-amino-5-fluoropyrimidin-4-yl)-3-((3-chloro-5-(trifluoromethyl)phenyl)amino)-4'-(4-methylpiperazine-1-carbonyl)-[1,3'-bipiperidin]-2-one The title compound was obtained from chiral separation of trans-1'-(6-amino-5-fluoropyrimidin-4-yl)-3-((3-chloro-5-(trifluoromethyl)phenyl) amino)-N,N-dimethyl-2-oxo-[1,3'-bipiperidine]-4'-carboxamide 23 using a two step chiral SFC separation. Firstly, the mixture was separated into two peaks containing a mixture of two diastereomers ((3'R,4'S)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carboxamide and (3'S,4'R)-1'-(6-amino-5-fluoropyrimidin-4-yl)-3-((3-chloro-5-(trifluoromethyl)phenyl)amino)-N,N-dimethyl-2-oxo-[1,3'-bipiperidine]-4'-carb oxamide) using a ChiralPak IC (2×15 cm, 30% methanol w/0.1 DEA) column, and then each mixture containing a pair of isomers was further separated into the single enantiomers using a ChiralPak IA (2×15 cm, 30% methanol w/0.1% DEA 100 bar) column. ¹H NMR (400 MHz, CD₃OD) δ: 7.96 (br. s., 1H), 6.90 (br. s., 1H), 6.76 (d, J=10.04 Hz, 2H), 4.60 (t, J=14.06 Hz, 2H), 4.19-4.32 (m, 1H), 3.67-3.78 (m, 1H), 3.43-3.54 (m, 3H), 3.35-3.38 (m, 3H), 3.16 (t, J=12.42 Hz, 1H), 2.86 (t, J=7.40 Hz, 2H), 2.79 (s, 3H), 2.32 (dd, J=5.02, 12.80 Hz, 1H), 1.89-2.07 (m, 4H), 1.62-1.76 (m, 5H), Example 8

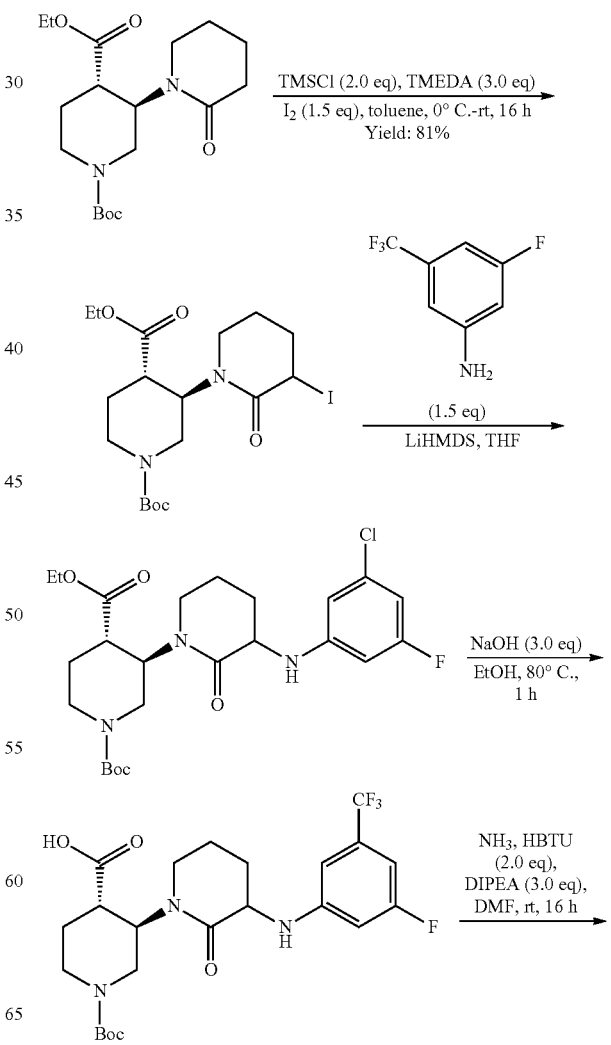

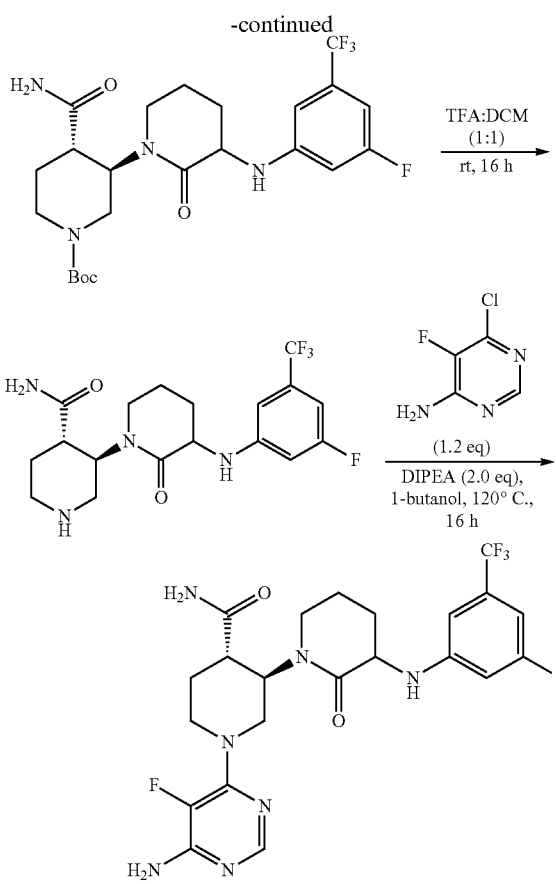

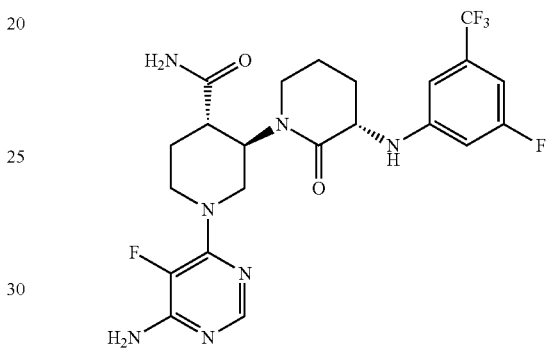

The synthesis of 1'-(6-amino-5-fluoropyrimidin-4-yl)-3-((3-fluoro-5-(trifluoromethyl)phenyl)amino)-2-oxo-[1,3'-bipiperidine]-4'-carboxamide A similar procedure was used as described for the synthesis of (3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxamide 14 to afford the crude material which was purified by pre-HPLC (MeOH/H$_2$O with 0.05% NH$_3$.H$_2$O as mobile phase) to give the title compound (175 mg, yield: 69%) as a yellow solid. ESI-MS (M+H)$^+$: 514.19. HPLC: (214 nm: 96.13%, 254 nm: 96.53%). $^1$H NMR (400 MHz, CD$_3$OD) δ: 7.79-7.78 (m, 1H), 6.76 (s, 1H), 6.63-6.54 (m, 2H), 4.41-4.36 (m, 2H), 4.08-4.06 (m, 1H), 3.55-3.41 (m, 3H), 3.28-3.25 (m, 1H), 2.99-2.93 (m, 1H), 2.28-2.21 (m, 1H), 1.98-1.78 (m, 6H).

(3R,3'R,4'S)-1'-(6-amino-5-fluoropyrimidin-4-yl)-3-((3-fluoro-5-(trifluoromethyl)phenyl)amino)-2-oxo-[1,3'-bipiperidine]-4'-carboxamide The mixture of four diastereomers was separated into three peaks by SFC (IA (3×15 cm), 30% EtOH (0.1% DEA)/CO$_2$, 100 bar, 70 ml/min) and peak 3 corresponded to the titled compound. LCMS (Agilent 460, 254 nm): ES (+) MS m/e=514.0 (M+1) @ 1.09 min. $^1$H NMR (400 MHz, CDCl$_3$) δ: 7.91 (br. s., 1H), 6.66 (d, J=8.53 Hz, 1H), 6.63 (s, 1H), 6.46 (d, J=10.79 Hz, 1H), 6.12 (br. s., 1H), 5.47 (br. s., 1H), 5.16 (d, J=3.51 Hz, 1H), 4.91 (br. s., 2H), 4.35-4.54 (m, 2H), 3.82 (td, J=5.11, 10.60 Hz, 2H), 3.51-3.60 (m, 1H), 3.34-3.48 (m, 3H), 2.96 (t, J=12.30 Hz, 1H), 2.35-2.47 (m, 1H), 1.91-2.06 (m, 3H), 1.84 (dq, J=3.89, 12.76 Hz, 1H), 1.48-1.62 (m, 1H).

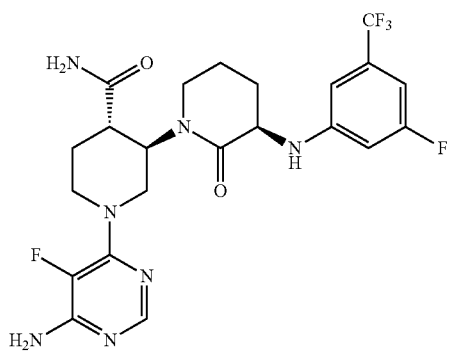

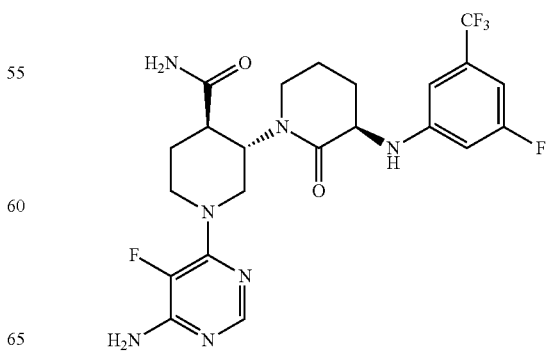

(3S,3'R,4'S)-1'-(6-amino-5-fluoropyrimidin-4-yl)-3-((3-fluoro-5-(trifluoromethyl)phenyl)amino)-2-oxo-[1,3'-bipiperidine]-4'-carboxamide The mixture of four diastereomers was separated into three peaks by SFC (IA (3×15 cm), 30% EtOH (0.1% DEA)/CO$_2$, 100 bar, 70 ml/min). Peak 2 of 3 corresponded to desired compound. LCMS (Agilent 460, 254 nm): ES (+) MS m/e=514.0 (M+1) @ 1.10 min. $^1$H NMR (400 MHz, DMSO-d$_6$) δ: 7.77 (d, J=1.76 Hz, 1H), 7.39 (s, 1H), 6.85 (s, 1H), 6.81 (s, 1H), 6.74 (d, J=12.30 Hz, 1H), 6.47-6.66 (m, 4H), 4.23 (d, J=12.80 Hz, 2H), 3.90-4.18 (m, 2H), 3.34-3.46 (m, 2H), 3.12 (br. s., 1H), 2.94 (br. s., 1H), 2.82 (t, J=12.42 Hz, 1H), 2.10 (qd, J=5.75, 12.11 Hz, 1H), 1.74-1.92 (m, 3H), 1.56-1.72 (m, 1H), 1.37-1.52 (m, 1H).

(3R,3'S,4'R)-1'-(6-amino-5-fluoropyrimidin-4-yl)-3-((3-fluoro-5-(trifluoromethyl)phenyl)amino)-2-oxo-[1,3'-bipiperidine]-4'-carboxamide The mixture of four diastereomers was separated into three peaks by SFC (IA (3×15 cm), 30% EtOH (0.1% DEA)/CO₂, 100 bar, 70 ml/min). Peak 1 of 3 was further purified by SFC (IA (3×15 cm), 30% iPrOH (0.1% DEA)/CO₂, 100 bar, 70 ml/min) to afford the titled compound. LCMS (Agilent 460, 254 nm): ES (+) MS m/e=514.0 (M+1) @ 1.10 min. ¹H NMR (400 MHz, DMSO-d₆) δ: 7.77 (d, 1.5 Hz, 1H), 7.39 (s., 1H), 6.85 (s, 1H), 6.81 (s., 1H), 6.74 (d, J=12.30 Hz, 1H), 6.47-6.66 (m, 4H), 4.16-4.46 (m, 2H), 3.95-4.16 (m, 2H), 3.34-3.48 (m, 2H), 3.12 (br. s., 1H), 2.87-3.01 (m, 2H), 2.82 (t, J=12.30 Hz, 1H), 2.10 (qd, J=5.75, 12.11 Hz, 1H), 1.74-1.92 (m, 3H), 1.54-1.74 (m, 1H), 1.35-1.52 (m, 1H).

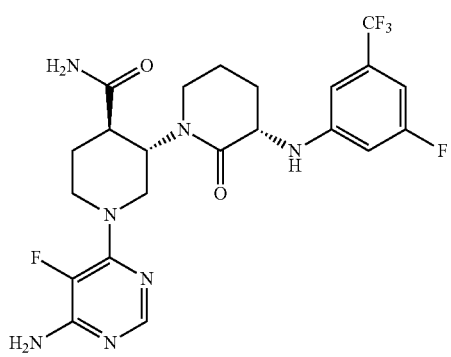

(3S,3'R,4'S)-1'-(6-amino-5-fluoropyrimidin-4-yl)-3-((3-fluoro-5-(trifluoromethyl)phenyl)amino)-2-oxo-[1,3'-bipiperidine]-4'-carboxamide The mixture of four diastereomers was separated into three peaks by SFC (IA (3×15 cm), 30% EtOH (0.1% DEA)/CO₂, 100 bar, 70 ml/min). Peak 1 of 3 was further purified by SFC (IA (3×15 cm), 30% iPrOH (0.1% DEA)/CO₂, 100 bar, 70 ml/min) to afford the titled compound.

LCMS (Agilent 460, 254 nm): ES (+) MS m/e=514.0 (M+1) @ 1.10 min. ¹H NMR (400 MHz, DMSO-d₆) δ: 7.77 (d, J=1.76 Hz, 1H), 7.38 (br. s., 1H), 6.84 (s, 2H), 6.70 (d, J=12.30 Hz, 1H), 6.47-6.65 (m, 4H), 4.18-4.48 (m, 2H), 3.92-4.18 (m, 2H), 3.38-3.49 (m, 1H), 3.20-3.30 (m, 1H), 3.11 (br. s., 1H), 2.88-2.99 (m, 1H), 2.83 (t, J=12.30 Hz, 1H), 2.14 (qd, J=6.03, 12.52 Hz, 1H), 1.74-1.92 (m, 3H), 1.59-1.74 (m, 1H), 1.41-1.58 (m, 1H).

Example 9

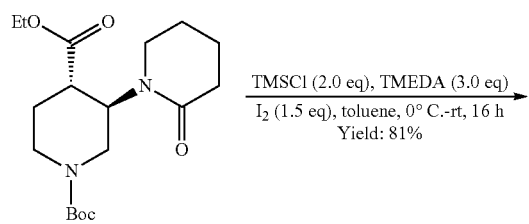

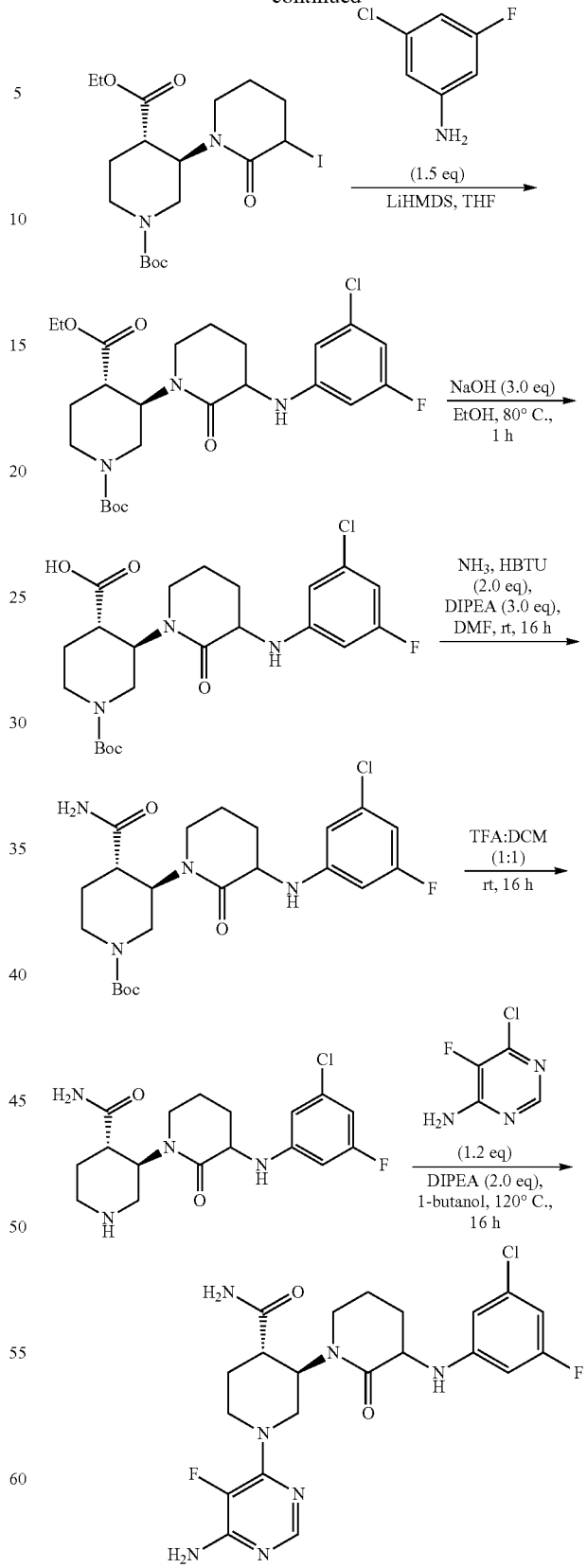

The synthesis of (3'R,4'S)-1'-(6-amino-5-fluoropyrimidin-4-yl)-3-((3-chloro-5-fluorophenyl) amino)-2-oxo-[1,3'- bipiperidine]-4'-carboxamide. A similar procedure was used as described for the synthesis of (3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxamide 14 to afford the crude material which was purified by pre-HPLC (MeOH/H$_2$O with 0.05% NH$_3$.H$_2$O as mobile phase) to give the title compound (141 mg, Y: 30%) as a white solid. ESI-MS (M+H)$^+$: 479.9. HPLC: (214 nm: 100%, 254 nm: 100%). $^1$H NMR (400 MHz, DMSO d$_6$) δ: 7.78-7.77 (m, 1H), 7.40-7.38 (m, 1H), 6.86-6.82 (m, 1H), 6.62-6.55 (m, 3H), 6.45-6.37 (m, 3H), 4.26-3.94 (m, 4H), 3.47-3.39 (m, 1H), 3.20-3.03 (m, 2H), 2.90-2.78 (m, 2H), 2.18-2.04 (m, 1H), 1.86-1.34 (m, 5H).

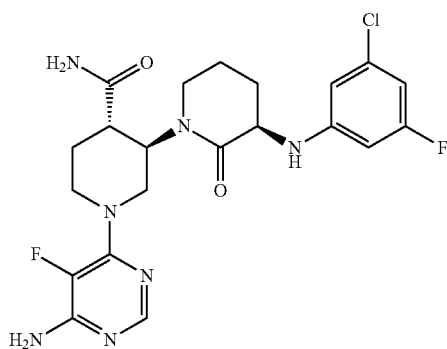 [SMILES: NC(=O)[C@H]1CCN(c2ncnc(N)c2F)C[C@@H]1N1CCC[C@@H](Nc2cc(F)cc(Cl)c2)C1=O]

(3R,3'R,4'S)-1'-(6-amino-5-fluoropyrimidin-4-yl)-3-((3-chloro-5-fluorophenyl)amino)-2-oxo-[1,3'-bipiperidine]-4'-carboxamide Wyatt, P.G. et al., "Identification of potent and selective oxytocin The mixture of four diastereomers was separated into three peaks by SFC (IC (2×15 cm), 25% MeOH (0.1% DEA)/CO$_2$, 100 bar, 60 ml/min) to afford the title compound as peak 3 respectively. LCMS (Agilent 460, 254 nm): ES (+) MS m/e=480.0 (M+1) @ 1.01 min. $^1$H NMR (400 MHz, CDCl$_3$) δ: 7.90 (br. s., 1H), 6.44 (d, J=8.53 Hz, 1H), 6.40 (s, 1H), 6.30 (br. s., 1H), 6.23 (d, J=11.04 Hz, 1H), 5.63 (br. s., 1H), 5.09 (br. s., 1H), 4.94 (br. s., 2H), 4.45 (d, J=12.80 Hz, 2H), 3.68-3.95 (m, 2H), 3.49-3.56 (m, 2H), 3.35-3.46 (m, 2H), 2.89-2.99 (m, 1H), 2.31-2.44 (m, 1H), 1.90-2.04 (m, 3H), 1.76-1.89 (m, 1H), 1.49-1.61 (m, 1H).

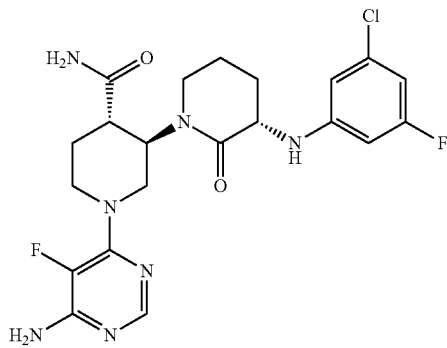 [SMILES: NC(=O)[C@H]1CCN(c2ncnc(N)c2F)C[C@@H]1N1CCC[C@H](Nc2cc(F)cc(Cl)c2)C1=O]

(3S,3'R,4'S)-1'-(6-amino-5-fluoropyrimidin-4-yl)-3-((3-chloro-5-fluorophenyl)amino)-2-oxo-[1,3'-bipiperidine]-4'-carboxamide The mixture of four diastereomers was separated into three peaks by SFC (IC (2×15 cm), 25% MeOH (0.1% DEA)/CO$_2$, 100 bar, 60 ml/min) to afford the title compound as peak 1 respectively.

LCMS (Agilent 460, 254 nm): ES (+) MS m/e=480.0 (M+1) @ 1.01 min. $^1$H NMR (400 MHz, DMSO-d$_6$) δ: 7.77 (d, J=1.76 Hz, 1H), 7.39 (s., 1H), 6.81 (s, 1H), 6.57 (s, 3H), 6.46 (d, J=12.30 Hz, 1H), 6.39 (dd, J=1.76, 8.78 Hz, 1H), 6.34 (d, J=7.53 Hz, 1H), 4.28 (br. s., 1H), 4.23 (d, J=13.05 Hz, 1H), 4.13 (dd, J=2.76, 12.30 Hz, 1H), 4.03 (td, J=6.56, 10.98 Hz, 1H), 3.33-3.46 (m, 2H), 3.11 (br. s., 1H), 2.94 (br. s., 1H), 2.82 (t, J=12.30 Hz, 1H), 2.09 (qd, J=5.75, 12.11 Hz, 1H), 1.72-1.92 (m, 3H), 1.56-1.72 (m, 1H), 1.29-1.50 (m, 1H).

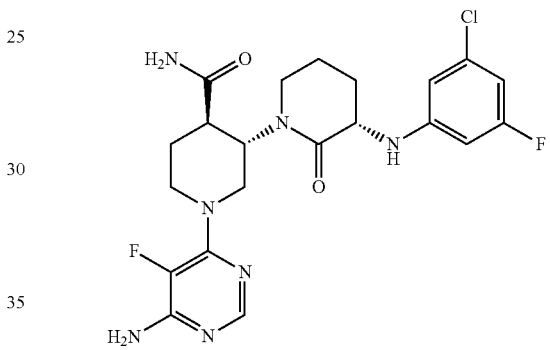

(3S,3'S,4'R)-1'-(6-amino-5-fluoropyrimidin-4-yl)-3-((3-chloro-5-fluorophenyl)amino)-2-oxo-[1,3'-bipiperidine]-4'-carboxamide The mixture of four diastereomers was separated into three peaks by SFC (IC (2×15 cm), 25% MeOH (0.1% DEA)/CO$_2$, 100 bar, 60 ml/min). Peak 2 of 3 was further purified by SFC (IA (3×15 cm), 30% iPrOH (0.1% DEA)/CO$_2$, 100 bar, 60 ml/min) to afford the title compound. LCMS (Agilent460, 254 nm): ES (+) MS m/e=480.0 (M+1) @ 1.01 min. $^1$H NMR (400 MHz, DMSO-d$_6$) δ: 7.77 (d, J=2.01 Hz, 1H), 7.37 (br. s., 1H), 6.84 (s, 1H), 6.57 (s, 2H), 6.55 (br. s., 1H), 6.30-6.48 (m, 3H), 4.28 (br. s., 1H), 4.23 (d, J=13.05 Hz, 1H), 4.13 (dd, J=3.39, 12.67 Hz, 1H), 3.97 (td, J=6.84, 10.42 Hz, 1H), 3.38-3.50 (m, 1H), 3.22-3.29 (m, 1H), 3.10 (br. s., 1H), 2.71-2.97 (m, 1H), 2.83 (t, J=12.30 Hz, 1H), 2.13 (qd, J=6.13, 12.49 Hz, 1H), 1.73-1.91 (m, 3H), 1.58-1.73 (m, 1H), 1.39-1.53 (m, 1H).

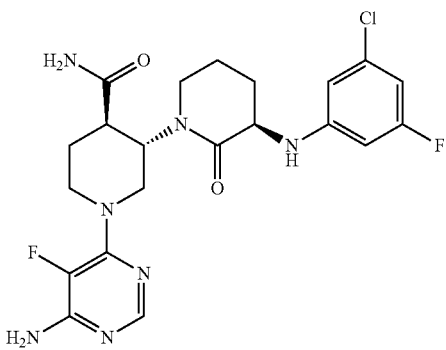 [SMILES: NC(=O)[C@@H]1CCN(c2ncnc(N)c2F)C[C@H]1N1CCC[C@@H](Nc2cc(F)cc(Cl)c2)C1=O]

(3R,3'S,4'R)-1'-(6-amino-5-fluoropyrimidin-4-yl)-3-((3-chloro-5-fluorophenyl)amino)-2-oxo-[1,3'-bipiperidine]-4'-carboxamide The mixture of four diastereomers was separated into three peaks by SFC (IC (2×15 cm), 25% MeOH (0.1% DEA)/CO$_2$, 100 bar, 60 ml/min). Peak 2 of 3 was further purified by SFC (IA (3×15 cm), 30% iPrOH (0.1% DEA)/CO$_2$, 100 bar, 60 ml/min) to afford the title compound. LCMS (Agilent460, 254 nm): ES (+) MS m/e=480.0 (M+1) @ 1.01 min. $^1$H NMR (400 MHz, DMSO-d$_6$) δ 7.77 (d, J=1.76 Hz, 1H), 7.39 (s, 1H), 6.81 (s, 1H), 6.57 (s, 3H), 6.46 (td, J=2.01, 12.30 Hz, 1H), 6.39 (td, J=1.95, 8.66 Hz, 1H), 6.34 (d, J=7.53 Hz, 1H), 4.18-4.48 (m, 2H), 4.09-4.18 (m, 1H), 3.79-4.09 (m, 1H), 3.33-3.45 (m, 2H), 3.11 (br. s., 1H), 2.92 (br. s., 1H), 2.82 (t, J=12.42 Hz, 1H), 2.09 (qd, J=5.75, 12.11 Hz, 1H), 1.74-1.93 (m, 3H), 1.51-1.74 (m, 1H), 1.32-1.51 (m, 1H).

Example 10

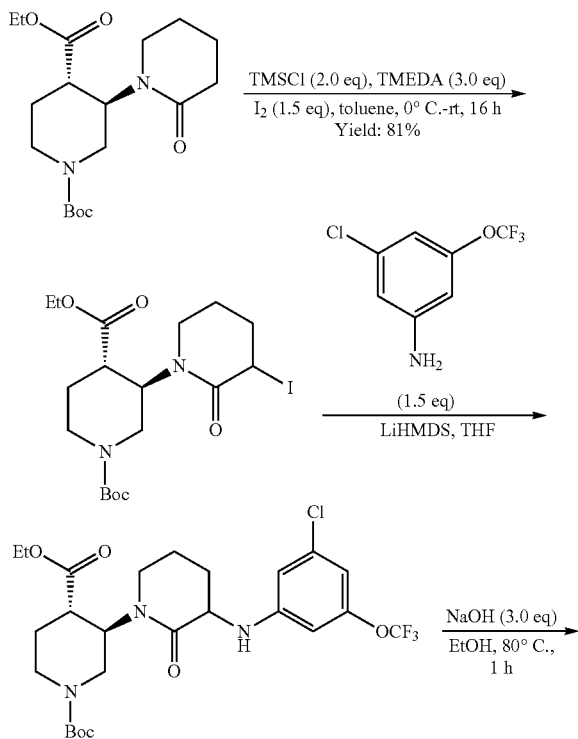

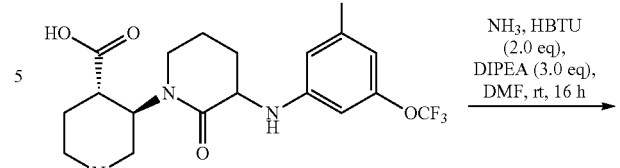

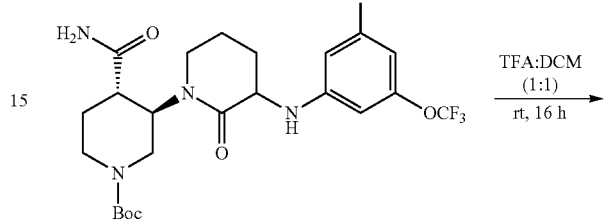

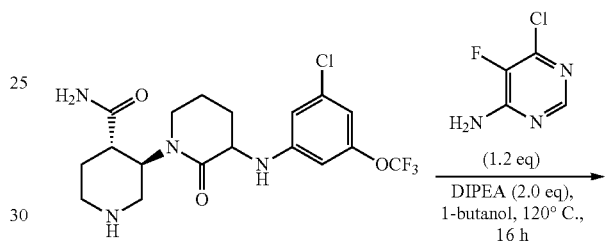

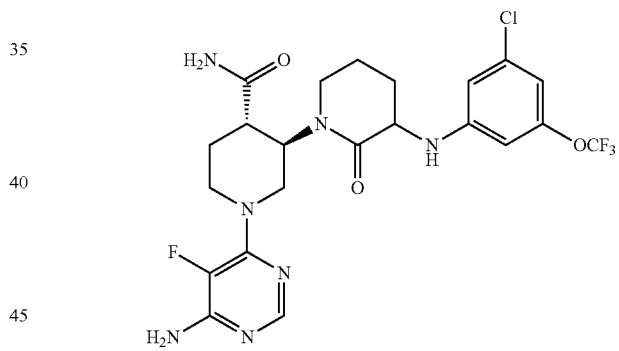

The synthesis of (3'R,4'S)-1'-(6-amino-5-fluoropyrimidin-4-yl)-3-((3-chloro-5-(trifluoromethoxy) phenyl)amino)-2-oxo-[1,3'-bipiperidine]-4'-carboxamide A similar procedure was used as described for the synthesis of (3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxamide 14 to afford the crude material which was purified by pre-HPLC (MeOH/H$_2$O with 0.05% NH$_3$.H$_2$O as mobile phase) to give the title compound (320 mg, yield: 44%) as a yellow solid. ESI-MS (M+H)$^+$: 546.16. HPLC (214 nm: 98.4%, 254 nm: 98.0%). $^1$H NMR (400 MHz, DMSO-d$_6$) δ: 7.77 (s, 1H), 7.39 (s, 1H), 6.84-6.81 (m, 1H), 6.75-6.72 (m, 1H), 6.62-6.57 (m, 3H), 6.52-6.47 (m, 2H), 4.24-3.98 (m, 4H), 3.47-3.40 (m, 1H), 3.17-2.99 (m, 2H), 2.86-2.79 (m, 2H), 2.15-1.99 (m, 1H), 1.86-1.60 (m, 4H), 1.48-1.39 (m, 1H).

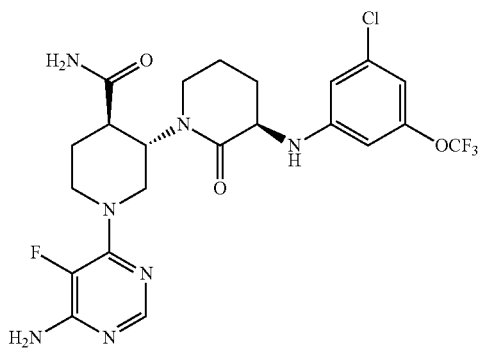 [SMILES: NC(=O)[C@@H]1CCN(c2ncnc(N)c2F)C[C@H]1N1CCC[C@@H](Nc2cc(Cl)cc(OC(F)(F)F)c2)C1=O]

(3R,3'S,4'R)-1'-(6-amino-5-fluoropyrimidin-4-yl)-3-((3-chloro-5-(trifluoromethoxy)phenyl)amino)-2-oxo-[1,3'-bipiperidine]-4'-carboxamide The mixture of four diastereomers was purified by SFC (AD-H (2×25 cm), 30% EtOH (0.1% DEA)/CO$_2$, 100 bar, 70 ml/min) to afford the title compound. LCMS (Agilent460, 254 nm): ES (+) MS m/e=546.0 (M+1) @ 1.20 min. $^1$H NMR (400 MHz, DMSO-d$_6$) δ: 7.77 (d, J=1.76 Hz, 1H), 7.39 (br. s., 1H), 6.81 (s, 1H), 6.75 (s, 1H), 6.62 (s, 1H), 6.57 (s, 2H), 6.38-6.52 (m, 2H), 4.23 (d, J=13.05 Hz, 2H), 3.92-4.18 (m, 2H), 3.34-3.45 (m, 2H), 3.11 (br. s., 1H), 2.93 (br. s., 1H), 2.82 (t, J=12.30 Hz, 1H), 2.08 (qd, J=5.75, 12.11 Hz, 1H), 1.74-1.92 (m, 3H), 1.56-1.73 (m, 1H), 1.36-1.50 (m, 1H).

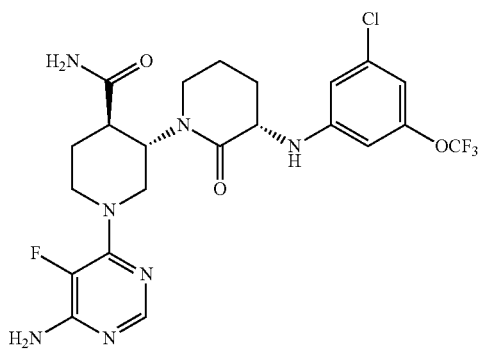 [SMILES: NC(=O)[C@@H]1CCN(c2ncnc(N)c2F)C[C@H]1N1CCC[C@H](Nc2cc(Cl)cc(OC(F)(F)F)c2)C1=O]

(3S,3'S,4'R)-1'-(6-amino-5-fluoropyrimidin-4-yl)-3-((3-chloro-5-(trifluoromethoxy)phenyl)amino)-2-oxo-[1,3'-bipiperidine]-4'-carboxamide The mixture of four diastereomers was purified by SFC (AD-H (2×25 cm), 30% EtOH (0.1% DEA)/CO$_2$, 100 bar, 70 ml/min) to afford the title compound. LCMS (Agilent 460, 254 nm): ES (+) MS m/e=546.0 (M+1) @ 1.23 min. $^1$H NMR (400 MHz, DMSO-d$_6$) δ: 7.77 (d, J=2.01 Hz, 1H), 7.37 (br. s., 1H), 6.84 (s, 1H), 6.72 (s, 1H), 6.60 (s, 1H), 6.57 (s, 2H), 6.43-6.54 (m, 2H), 4.23 (d, J=13.05 Hz, 1H), 4.22 (br. s., 1H), 4.13 (dd, J=3.26, 12.30 Hz, 1H), 4.01 (td, J=6.81, 10.23 Hz, 1H), 3.44 (td, J=6.18, 12.49 Hz, 1H), 3.20-3.29 (m, 1H), 3.11 (br. s., 1H), 2.88 (br. s., 1H), 2.83 (t, J=12.30 Hz, 1H), 2.12 (qd, J=6.05, 12.46 Hz, 1H), 1.73-1.91 (m, 3H), 1.59-1.73 (m, 1H), 1.48 (td, J=9.41, 19.33 Hz, 1H).

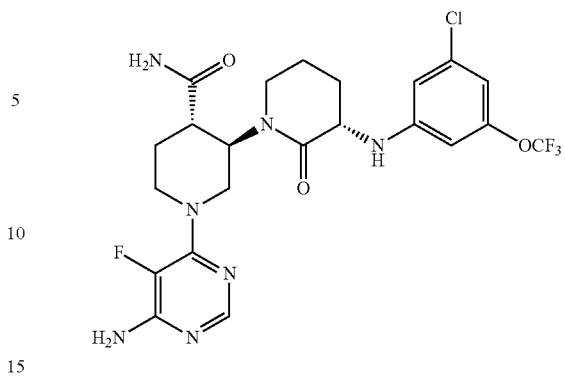

(3S,3'R,4'S)-1'-(6-amino-5-fluoropyrimidin-4-yl)-3-((3-chloro-5-(trifluoromethoxy)phenyl)amino)-2-oxo-[1,3'-bipiperidine]-4'-carboxamide The mixture of four diastereomers was purified by SFC (AD-H (2×25 cm), 30% EtOH (0.1% DEA)/CO$_2$, 100 bar, 70 ml/min) to afford the title compound. LCMS (Agilent 460, 254 nm): ES (+) MS m/e=546.0 (M+1) @ 1.22 min. $^1$H NMR (400 MHz, DMSO-d$_6$) δ: 7.77 (d, J=2.01 Hz, 1H), 7.38 (br. s., 1H), 6.81 (s, 1H), 6.75 (s, 1H), 6.62 (s, 1H), 6.57 (s, 2H), 6.42-6.51 (m, 2H), 4.23 (d, J=12.80 Hz, 2H), 3.97-4.18 (m, 2H), 3.34-3.44 (m, 2H), 3.10 (br. s., 1H), 2.93 (br. s., 1H), 2.82 (t, J=12.17 Hz, 1H), 2.03-2.15 (m, 1H), 1.77-1.90 (m, 3H), 1.57-1.73 (m, 1H), 1.37-1.48 (m, 1H).

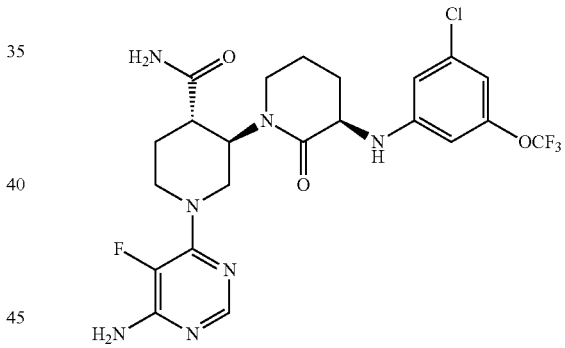

(3R,3'R,4'S)-1'-(6-amino-5-fluoropyrimidin-4-yl)-3-((3-chloro-5-(trifluoromethoxy)phenyl)amino)-2-oxo-[1,3'-bipiperidine]-4'-carboxamide The mixture of four diastereomers was purified by SFC (AD-H (2×25 cm), 30% EtOH (0.1% DEA)/CO$_2$, 100 bar, 70 ml/min) to afford the titled compound. LCMS (Agilent 460, 254 nm): ES (+) MS m/e=546.0 (M+1) @ 1.23 min. $^1$H NMR (400 MHz, CDCl$_3$) δ: 7.93 (s, 1H), 6.60 (s, 1H), 6.52 (s, 1H), 6.35 (s, 1H), 5.85 (br. s., 1H), 5.32 (br. s., 1H), 4.97-5.15 (m, 1H), 4.78 (br. s., 2H), 4.46 (d, J=13.05 Hz, 2H), 3.67-3.87 (m, 2H), 3.34-3.60 (m, 4H), 2.99 (t, J=12.17 Hz, 1H), 2.34-2.49 (m, 1H), 1.91-2.08 (m, 3H), 1.83 (dq, J=3.76, 12.72 Hz, 1H), 1.47-1.74 (m, 1H).

Example 11

In vitro BTK kinase assay: BTK-POLYGAT-LS ASSAY. The purpose of the BTK in vitro assay was to determine compound potency against BTK through the measurement of $IC_{50}$. Compound inhibition was measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 uL aliquot of an ATP/peptide master mix (final concentration; ATP 10 uM, polyGAT 100 nM) in kinase buffer (10 mM Tris-HCl pH 7.5, 10 mM $MgCl_2$, 200 uM $Na_3PO_4$, 5 mM DTT, 0.01% Triton X-100, and 0.2 mg/ml casein) was added to each well. Next, 1 uL of a 4-fold, 40× compound titration in 100% DMSO solvent was added, followed by adding 15 uL of BTK enzyme mix in 1× kinase buffer (with a final concentration of 0.25 nM). The assay was incubated for 30 minutes before being stopped with 28 uL of a 50 mM EDTA solution. Aliquots (5 uL) of the kinase reaction were transferred to a low volume white 384 well plate (Corning 3674), and 5 uL of a 2× detection buffer (Invitrogen PV3574, with 4 nM Tb-PY20 antibody, Invitrogen PV3552) was added. The plate was covered and incubated for 45 minutes at room temperature. Time resolved fluorescence (TRF) on Molecular Devices M5 (332 nm excitation; 488 nm emission; 518 nm fluorescein emission) was measured. $IC_{50}$ values were calculated using a four parameter fit with 100% enzyme activity determined from the DMSO control and 0% activity from the EDTA control.

Selected compounds of formula I were tested and found to be active in the polyGAT assay. Compounds I-1, I-2, I-3, I-4, I-5 and I-7 gave $IC_{50}$ values of 0.73 nM, 0.68 nM, 2.07 nM, 0.63 nM, 1.6 nM, and 1.2 nM respectively. Compound I-6 has an $IC_{50}$ value less than 1 nM. Comparator compound $I^C$, shown below, produced an $IC_{50}$ value of 2.0 nM.

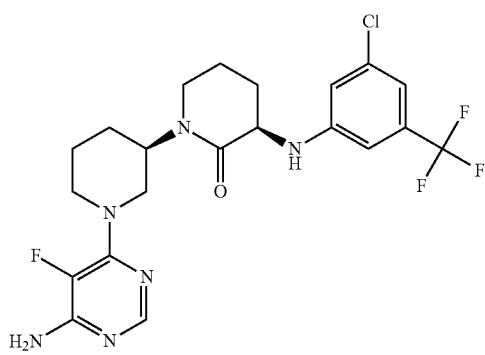

$I^C$

Example 12

Study Protocol to Determine Activation of the PXR Nuclear Receptor in Human DPX2 Cells a) Protocol Summary:

PXR has been shown to be a primary nuclear receptor that mediates drug-induced expression of CYP3A4 (Bertilsson G, et al.; Proc Natl Acad Sci USA. 1998 Oct. 13; 95(21): 12208-13). Based on this pathway of CYP3A4 induction, cell-based PXR reporter gene assay is commonly used to screen new molecular entities (NMEs) in early drug discovery stage, for their potential to induce CYP3A4 (Luo G, et al.; Drug Metab Dispos. 2002 July; 30(7):795-804.) Studies were designed to evaluate the effect of new molecular entities (NMEs) on the activation of human PXR in DPX2 cells. Cell lines stably transfected with the PXR nuclear receptor and corresponding response elements were seeded into 96-well plates. Twenty-four hr after seeding, cells were treated with 6 distinct concentrations of NMEs in triplicate wells (see below), and cells then returned to the incubator for an additional 24 hr. At the end of this incubation period, the number of viable cells/well were determined using Promega's Cell Titer Fluor cytotoxicity assay. Following this assay, Promega's ONE-Glo was added to the same wells and reporter gene activity assessed.

b) Test System:

The test system consisted of the stably transformed DPX2 tumor cell line plated on 96-well microtiter plates. An expression vector harboring the PXR nuclear receptor plus the appropriate enhancers and promoters linked to the luciferase reporter gene have been stably integrated into these tumor cell lines. Receptor activation was assessed by monitoring reporter gene activity, and by comparing the results to vehicle-treated cells. Positive controls consist of cells treated with 6 different concentrations (0.1, 0.5, 1, 5, 10, and 20 µM) of rifampicin. In this manner, compounds activating PXR can be easily and rapidly identified. Since stably-integrated cell lines were used, it is possible to observe from 3- to 70-fold receptor activation.

c) Data Processing and Receptor Activation Kinetics:

Data processed using MS-Excel was calculated as the mean (n=3) and % CV of the fold PXR activation relative to vehicle-treated cells at each of the 6 different doses. All activation data was normalized to the number of viable cells/well. Results were also expressed as a percentage of the response given by the appropriate positive control at a 10 µM dose. $EC_{50}$ and $E_{max}$ values were derived for test compounds that give receptor activation using nonlinear regression of typical log dose-response curves (Prism V5.0c, GraphPad Software, San Diego, Calif.). Agents exhibiting atypical dose-response curves were not analyzed in this fashion.

d) New Molecular Entities (NMEs): Test Compounds were Tested at 0.05, 0.1, 0.5, 1, 2.5, and 10 µM Selected compounds of formula I were tested in the PXR assay. Compounds I-1, I-2, I-3, I-4, and I-5 gave PXR % induction (relative to 10 uM rifampin) of 62%, 42%, 47%, 67%, and 90%, respectively. Comparator compound $I^C$, shown above, produced a PXR % induction of 95%.

Example 13

Protocol for FastPatch hERG Inhibition Assay:

The cardiac potassium channel, hERG, is responsible for a rapid delayed rectifier current ($I_{Kr}$) in human ventricle and inhibition of $I_{Kr}$ is the most common cause of cardiac action potential prolongation by non-cardiac drugs (see, e.g., Weirich and Antoni, Basic Res. Cardiol., 93, Suppl. 1, 125-32, 1998; Yap and Camm, Clin. Exp. Allergy, 29, Suppl. 3, 174-81, 1999). Increased action potential duration has been cited as a factor in causing prolongation of the QT interval that has been associated with a dangerous ventricular arrhythmia, torsade de pointes (Brown and Rampe, Pharmaceutical News, 7, 15-20, 2000).

The in vitro effects of provided compounds was investigated on the hERG (human ether-à-go-go-related gene) potassium channel current (a surrogate for $I_{Kr}$, the rapidly activating, delayed rectifier cardiac potassium current) expressed in human embryonic kidney (HEK293) cells stably transfected with hERG cDNA. Cells were placed in HEPES-buffered physiological saline solution in a glass-lined 96-well plate and loaded with appropriate amounts of test and control solutions for a duration of a 3-minute exposure at each concentration. Test compound was diluted in 0.3% DMSO. An automated parallel patch clamp system, QPatch HT (Sophion Bioscience A/S, Denmark), was used to evaluate at various concentrations (e.g., 10 μM). The $IC_{50}$ values was estimated based on the hERG inhibition data. The study was performed at ChanTest (14656 Neo Parkway, Cleveland, Ohio). The QPatch screen is further described by Janzen and Bernasconi (eds.), High Throughput Screening, Methods and Protocols, Second Edition, vol. 565, chapter 10, pg. 209-223, 2009.

Selected compounds of formula I were tested in the hERG assay. Compounds I-1, I-2, I-3, and I-4 gave hERG $IC_{50}$ of 15.6 uM, 30 uM, 14.6 uM, and 13.7 uM, respectively. Compound I-5 shows no observable activity in the hERG assay at 10 uM (no $IC_{50}$ available). Compound I-6 shows little observable hERG activity (<20% inhibition) at 10 uM (no $IC_{50}$ available). Compound I-7 shows hERG activity (65% inhibition) at 10 uM (no $IC_{50}$ available). Comparator compound $I^C$, shown above, produced a hERG $IC_{50}$ of 1.18 uM or activity (87% inhibition) at 10 uM.

Example 14

GSH Trapping in Human Liver Microsome:Protocol

Test compound (final concentration 10 uM) is incubated with either human or rat liver microsomes (final concentration 1 mg/mL), along with activating cofactors NADPH (final concentration 1 mM), potassium phosphate (final concentration 100 mM pH 7.4), magnesium chloride (final concentration 3.3 mM) and the trapping agent GSH (final concentration 5 mM). The incubation mixture is incubated for 60 min at 37° C. and terminated with ice cold acetonitrile (equal volume as incubation mixture) and the supernatents isolated. The supernatants are either injected directly for LC/MS/MS analysis or dried under $N_2$ and reconstituted in water:acetonitrile (80:20) mixture before LC/MS/MS analysis. The corresponding GSH conjugate is evaluated via LC/MS/MS, using a Triple TOF5600/Xevo Qtof MSe.

Example 15

Rat Collagen-Induced Arthritis Model

The collagen induced arthritis (CIA) model in female Lewis rats requires primary T and B cell immune responses to type II collagen (CII) immunization for the development of a severe inflammatory disease (see Goldschmidt T J, Holmdahl R. Cell Immunol. 154(1):240-8, 1994; Helfgott, S. M., et al; Clin. Immunol. Immunopathol. 31:403, 1984; Holmdahl R. et al., J Autoimmun. 7(6):739-52, 1994; and Stuart, J. M., et al., J. Exp. Med. 155:1, 1982). Clinical disease onsets after a secondary CII challenge and the disease progresses over the following eight days.

Generally, female Lewis rats are immunized with bovine collagen type II in incomplete Freund's adjuvant. Rats (N=10/group) receive daily oral administration of test compound or vehicle BID by oral gavage beginning on day 1 (therapeutic). Clinical severity of arthritis is assessed by caliper measurements of ankles taken every day beginning on Day 0.

Detailed protocol: Female Lewis rats are immunized subcutaneously with bovine collagen type II (1:1 emulsion of 2 mg/ml bovine CII in 0.01 N acetic acid: Incomplete Freund's Adjuvant) at three sites of back skin. Six days post immunization rats receive a second subcutaneous injection of bovine CII. A compound of formula I suspension or vehicle (0.5% CMC, 0.1% Tween 80) is administered by oral gavage BID beginning on day 0 (prophylactic) (n=10 animals/group). Clinical severity of CIA is assessed by caliper measurements of ankles taken every day beginning on Day 9. Baseline ankle caliper measurements are taken and confirmed as clinically normal (0.260-0.264 in) for prophylactic treatment. Baseline ankle caliper measurements for established disease animals is assessed on day 1 of therapeutic dosing and animals are randomly assigned to treatment groups after confirmation of clinical disease onset (0.2751-0.2755 in). Data are analyzed across all groups using a one-way analysis of variance (1-way ANOVA), along with an appropriate multiple comparison post-test. Significance for all tests is set at $p<0.05$.

Example 16

Analysis of BCR Pathway Activation Via Inhibition of Phosphorylation of PLCγ2

Protocol: One day before treatment, Ramos cells are plated at a density of $3 \times 10^5$ cells per well in 200 μL of complete medium in a 96-well tissue culture filter plates (Millipore, Billerica, Mass.). On the day of treatment, used medium is removed by filtration and the cells re-suspended in 200 μL serum free medium containing serial compound dilutions and DMSO to 0.1%, then incubated for 2 hours at 37° C. Cells are stimulated for 5 minutes with 10 μg/mL goat anti-human IgM at 37° C. All medium is removed by filtration and the cells are rinsed with ice cold PBS then lysed on ice for 1 hour with lysis buffer containing; 20 mM Tris (pH 7.5), 150 mM NaCl, 1 mM EDTA, 1 mM EGTA, 2 mM $Na_3VO_4$, 1% Triton X-100, 0.1% SDS, protease inhibitor cocktail, 1 mM phenylmethylsulfonyl fluoride, (PMSF), Phosphatase inhibitor mix 2 (Sigma cat # P5726 from Sigma, St. Louis, Mo.), and Phosphatase inhibitor mix 3 (Sigma cat #P0044 from Sigma, St. Louis, Mo.). Lysates are subsequently transferred to standard MSD plates (Meso Scale Discovery, (MSD), (Gaithersburg, Md.)), pretreated with capture antibody (anti-total PLCγ2 antibody B10, (SantaCruz Biotechnologies (Santa Cruz, Calif.)) and blocked with BSA according to the manufacturer's directions. Lysates are incubated in the prepared MSD plates overnight at 4° C. with gentle agitation. Wells are washed three times with TBST and treated with anti pPLCγ2 (SantaCruz) in 1% BSA in PBS for 1 hour at room temperature. Wells are again washed three times with TBST and treated with anti-rabbit sulfo-tag antibody (MSD), for 1 hour at room temperature. After washing with TBST, MSD read buffer is added and the luminescence is measured in an MSD SECTOR Imager 6000. Maximum response is determined as the average luminescence in wells containing stimulated cells treated with anti-IgM and DMSO. Minimal response is determined as the average luminescence in wells containing unstimulated cells treated with DMSO alone. The maximal and minimal values are used to normalize luminescence in compound treatment wells. The normalized values are plotted against compound concentration on a log scale then analyzed using Prizm software (GraphPad Software, Inc.). A sigmoidal dose-response equation with variable slope is used to fit the data and generate 50% inhibition concentration ($IC_{50}$).

Ramos cells are incubated in 96 well plates with a range of concentrations of a compound of formula I for 2 hours, stimulated with 10 μg/mL anti-IgM for 5 minutes, and PLCγ2 phosphorylation measured using an electrochemical-luminescent immunoassay. The $EC_{50}$ is calculated using GraphPad Prism software.

Example 17

Inhibition BCR-Induced Human B Cell Proliferation

Human CD19+ B cells are stimulated with an anti-IgM antibody and the activity of a compound of formula I is evaluated in terms of altering cellular metabolism after 72 hours. In this context, cellular metabolism directly correlates with cellular activation and proliferation, and can also reflect relative cell survival during proliferation. Anti-IgM antibody is evaluated for effects on B cell proliferation and determined to exhibit a half-maximal concentration for activation of 10 µg/ml. Using these activation conditions, varying concentrations of test compound are assayed, in triplicate in 0.1% DMSO, for impact on cellular metabolism of CD19+ B cells isolated from different donors.

Protocol: Human B cells are isolated from peripheral blood mononuclear cells or unpurified buffy coats using Ficoll-Hypaque gradients (Amersham) and negatively selected by magnetic cell sorting (Human B Cell Isolation Kit II, Miltenyi Biotec). Target cell purity is determined by flow cytometry by staining for markers of B cells, T cells and monocytes (CD19, CD3, CD14, respectively; BD Biosciences). Data are collected on a FACsCaliber flow cytometer and analyzed using FloJo software (BD Biosciences). Purity of human B cell preparations is routinely greater than 95%. Negatively selected human B cells are stimulated with 10 µg/mL anti-IgM F(ab')$_2$ (Jackson ImmunoResearch) in 96 well plates. 100,000 B cells in 0.2 mL RPMI+10% FBS are treated with varying concentrations (titrated from 5000 nM to 0 nM in 0.5% DMSO) of a compound of formula I in triplicate wells or vehicle control in 0.5% DMSO final concentration for 30 minutes at 37° C., 5% $CO_2$, then cells are stimulated with 10 µg/mL anti-IgM F(ab')2. B cells are stimulated for 72 hr at 37° C., 5% $CO_2$. Proliferation is measured using the CellTiter-Glo reagent (Promega), as measured on a luminometer. Mean values are plotted against maximum proliferation and $IC_{50}$ values are determined using GraphPad Prism v5 software.

Example 18

Evaluation of the Effect of Compounds on Myeloid Cell Activation In Vitro

FcγR activation of primary human macrophages. Autoantibody and immune-complex mediated activation through FcγR can be modeled by activation of macrophages with immobilized IgG. Primary human macrophages derived from GM-CSF treated monocytes up-regulate activation markers such as CD80, CD86, MHC antigens and the FcγRIII receptor. Human monocyte derived macrophages can be activated by plate-bound purified human IgG. This stimulation crosslinks the FcγRIII receptor and induces the secretion of pro-inflammatory cytokines such as TNFα, IL-6, IL1β and MCP-1. Compound of formula I are evaluated for inhibition of cytokine expression following FcR activation of human macrophages.

Generally, macrophages are cultured in plates previously incubated with purified IgG then washed. Titrations of test compound (10,000 nM to 0 nM) are added to these cultures. Cell culture supernatants are analyzed by ELISA for the expression of TNFα and IL-6.

Protocol: Human monocytes are isolated from buffy coats of healthy donors and negatively selected by magnetic cell sorting (Monocyte Isolation Kit II, Miltenyi Biotec). Purified monocytes are cultured in standard media supplemented with low-IgG FBS and 100 ng/mL GM-CSF for 5-7 days to induce macrophage differentiation. Cultured macrophages are stimulated with 100 µg/mL plate-bound purified IgG±a titration of test compound (10 µM to 0 nM). Supernatants are collected after 4 hrs and 18 hrs and analyzed for TNFα and IL-6, respectively.

Example 19

Efficacy in Mouse Collagen Antibody-Induced Arthritis

This Example relates not only to arthritis, but also evaluates the activity of autoantibodies and immune complexes in vivo and therefore is relevant to other inflammatory disorders such as SLE. In this experiment, the activity of autoantibodies and immune complexes produce a pathological endpoint that is dependent on FcR signalling, and the Fc portion of such antibodies is inhibited by administration of a compound of formula I.

The collagen antibody-induced arthritis (CAIA) model in female DBA/1 mice does not require cognate T and B cell responses for the induction of inflammation but rather relies on immune effector mechanisms for the development of clinical disease. A cocktail of four anti-collagen II (CII) specific monoclonal antibodies and immune stimulatory lipopolysaccharide (LPS) administered 3 days after CII specific antibody transfer promote antibody-Fc-Receptor engagement (Kagari T. et al.; *J Immunol.* 170:4318-24 (2003)), immune complex formation, complement activation (Banda N K, et al.; *Clin Exp Immunol.* 159:100-8 (2010)) and pro-inflammatory cytokine production to induce a severe inflammatory disease over a 10 day period.

Generally, arthritis is induced by injection of a cocktail of monoclonal anti-collagen antibodies into DBA/1 mice on day 0. Mice (N=10/group) receive daily oral administration of test compound either QD or BID as indicated beginning on day 0. Paw inflammation is evaluated daily.

Protocol: Female DBA/1 mice 6-8 weeks of age receive 2 mg of an arthitogenic four clone monoclonal antibody cocktail (Chondrex#10100) i.v. on day 0 followed by a 50 ug dose of LPS on 3 days later. Test compound suspension or vehicle (0.5% CMC, 0.1% Tween 80) is administered BID by oral gavage beginning on day 0 (10 animals/group) just prior to i.v. transfer of antibody cocktail. Clinical severity of CIA is assessed by monitoring inflammation on all four paws, applying a scale ranging from 0 to 4. Each paw is graded as follows: 0, normal; 1, mild but definite redness and swelling of the ankle or wrist, or redness and swelling of any severity for 1 or 2 digits; 2, moderate to severe redness and swelling of the ankle or wrist, or more than two digits; 3, redness and swelling (pronounced edema) of the entire paw; and 4, maximally inflamed limb with involvement of multiple joints. The sum of the four individual scores is the arthritis index, with a maximal possible score of 16 for each animal.

What is claimed is:

1. A method for treating a disorder associated with dysregulation of BCR signaling in a subject, the method comprising:
   administering to the subject an effective amount of a compound of Formula I, or a pharmaceutically acceptable salt thereof, or
   administering to the subject an effective amount of a pharmaceutical composition comprising a compound of Formula I, or a pharmaceutically acceptable salt thereof, and one or more pharmaceutically acceptable excipients;
   wherein the disorder is responsive to B-cell depletion;
   wherein the compound is of Formula I:

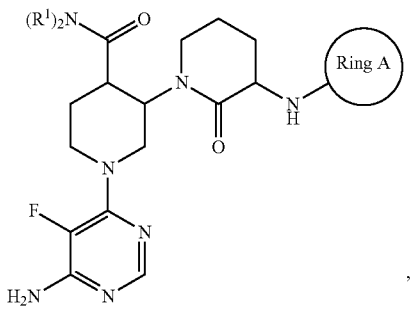

I wherein:

each $R^1$ is independently hydrogen, an optionally substituted $C_{1-6}$ aliphatic group, an optionally substituted 3-7 membered monocyclic heterocyclic group, or an optionally substituted heterocyclylalkyl group having 3-7 carbon atoms and 1-3 heteroatoms independently selected from nitrogen, oxygen, and sulfur;

or two $R^1$ groups are taken together with their intervening atoms to form an optionally substituted 3-7 membered saturated or partially unsaturated monocyclic heterocyclic ring having 1-2 heteroatoms independently selected from nitrogen, oxygen, and sulfur;

wherein optionally substituted groups may be substituted with halogen, —NO$_2$, —CN, —OR, —SR, —N(R)$_2$, —C(O)R, —CO$_2$R, —N(R)C(O)OR, —C(O)N(R)$_2$, —OC(O)R, —N(R)C(O)R, —S(O)R, —S(O)$_2$R, or —S(O)$_2$N(R)$_2$;

each R is independently hydrogen or $C_{1-6}$ aliphatic;

or two R groups attached to the same nitrogen are taken together with their intervening atoms to form an optionally substituted 3-7 membered saturated or partially unsaturated monocyclic heterocyclic ring having 1-2 heteroatoms, in which any second heteroatom is independently selected from nitrogen, oxygen, and sulfur;

Ring A is

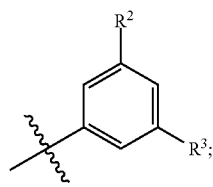

$R^2$ is —Cl or —F; and
$R^3$ is —CF$_3$, —OCF$_3$, or —F.

2. The method of claim 1, wherein the compound is of Formula II-a:

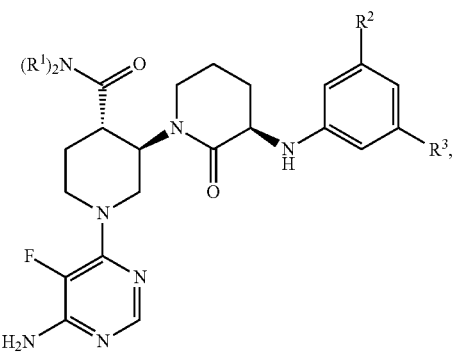

II-a or a pharmaceutically acceptable salt thereof.

3. The method of claim 1, wherein the compound is of Formula II-b:

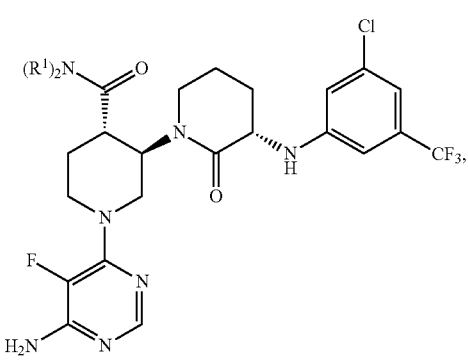

II-b or a pharmaceutically acceptable salt thereof.

4. The method of claim 1, wherein the compound is of Formula III:

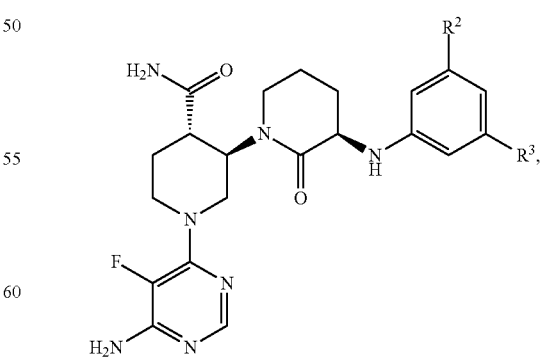

III or a pharmaceutically acceptable salt thereof.

5. The method of claim 1, wherein the compound is Formula IV:

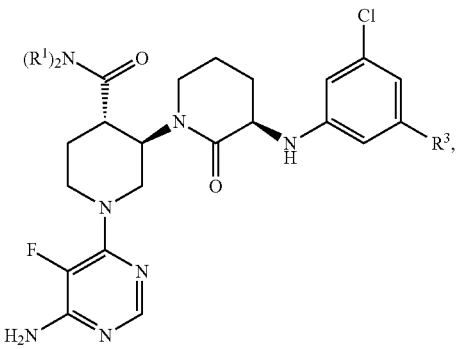

IV or a pharmaceutically acceptable salt thereof.

6. The method of claim 1, wherein one $R^1$ is hydrogen and the other $R^1$ is an optionally substituted $C_{1-6}$ aliphatic.

7. The method of claim 1, wherein both $R^1$ are optionally substituted $C_{1-6}$ aliphatic groups.

8. The method of claim 1, wherein both $R^1$ are hydrogen.

9. The method of claim 1, wherein $R^2$ is —Cl.

10. The method of claim 1, wherein $R^2$ is —F.

11. The method of claim 1, wherein $R^3$ is —$CF_3$.

12. The method of claim 1, wherein $R^3$ is —$OCF_3$.

13. The method of claim 1, wherein $R^3$ is —F.

14. The method of claim 1, wherein the compound administered is selected from the group consisting of:

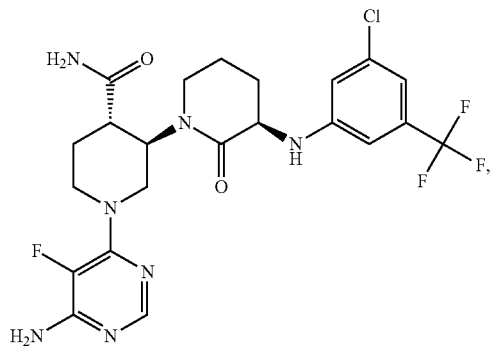

I-1

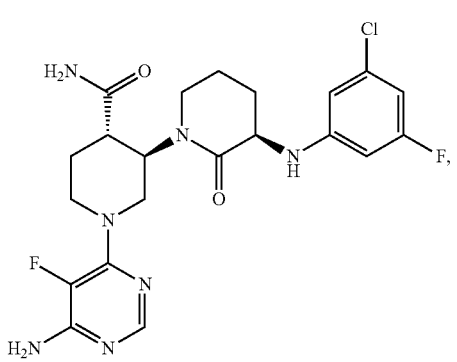

I-2

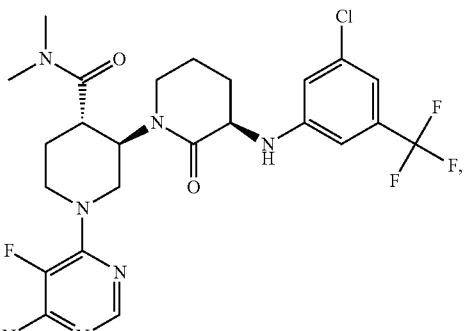

I-3

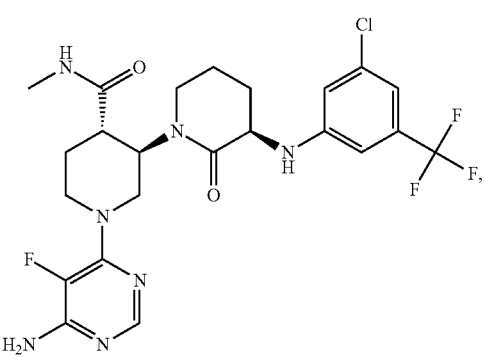

I-4

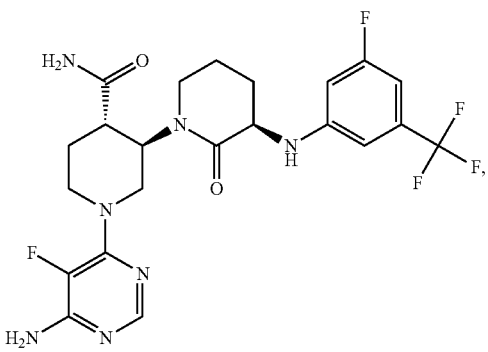

I-5

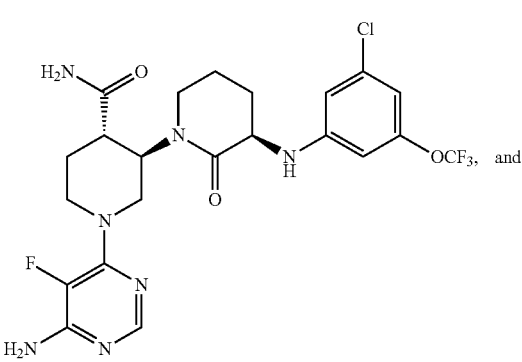

I-6

-continued

I-7

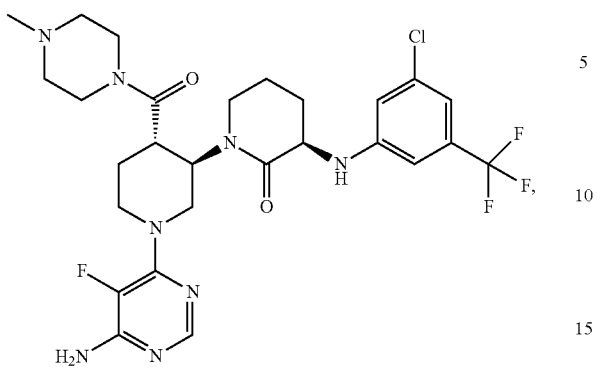

or a pharmaceutically acceptable salt thereof.

15. The method of claim 1, wherein the disorder is selected from the group consisting of autoimmune disorders, inflammatory disorders, and cancers.

16. A pharmaceutical composition comprising a compound of Formula I, or pharmaceutically acceptable salt thereof; and one or more pharmaceutically acceptable excipients;
wherein the compound is of Formula I:

I

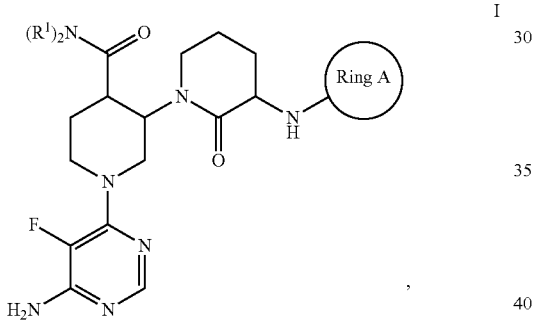

wherein:
each $R^1$ is independently hydrogen, an optionally substituted $C_{1-6}$ aliphatic group, an optionally substituted 3-7 membered monocyclic heterocyclic group, or an optionally substituted heterocyclylalkyl group having 3-7 carbon atoms and 1-3 heteroatoms independently selected from nitrogen, oxygen, and sulfur;
or two $R^1$ groups are taken together with their intervening atoms to form an optionally substituted 3-7 membered saturated or partially unsaturated monocyclic heterocyclic ring having 1-2 heteroatoms independently selected from nitrogen, oxygen, and sulfur;
wherein optionally substituted groups may be substituted with halogen, —$NO_2$, —CN, —OR, —SR, —$N(R)_2$, —C(O)R, —$CO_2R$, —N(R)C(O)OR, —C(O)N(R)$_2$, —OC(O)R, —N(R)C(O)R, —S(O)R, —S(O)$_2$R, or —S(O)$_2$N(R)$_2$;
each R is independently hydrogen or $C_{1-6}$ aliphatic;
or two R groups attached to the same nitrogen are taken together with their intervening atoms to form an optionally substituted 3-7 membered saturated or partially unsaturated monocyclic heterocyclic ring having 1-2 heteroatoms, in which any second heteroatom is independently selected from nitrogen, oxygen, and sulfur;

Ring A is

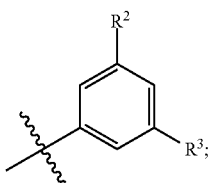

$R^2$ is —Cl or —F; and
$R^3$ is —$CF_3$, —$OCF_3$, or —F.

17. A pharmaceutical composition comprising a compound selected from the group consisting of:

I-1

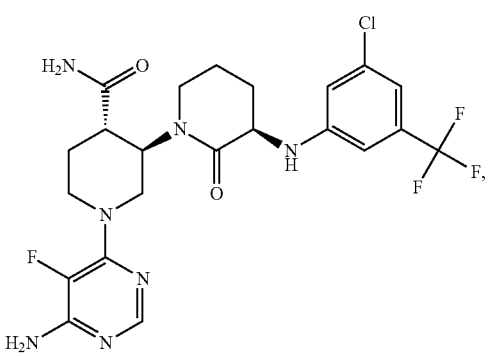

I-2

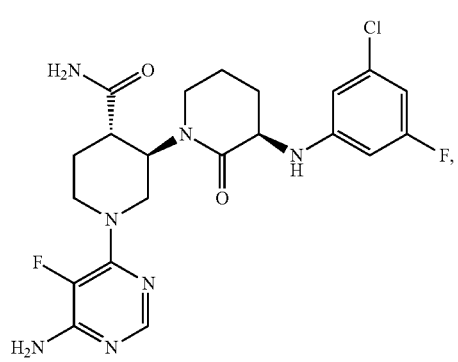

I-3

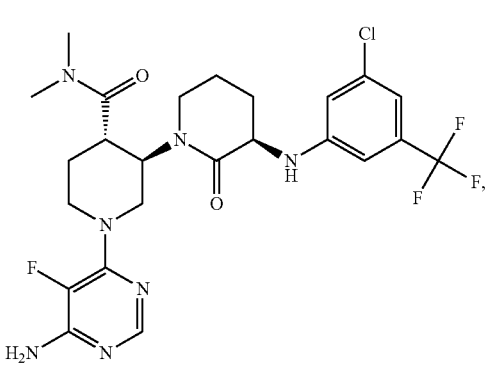

-continued
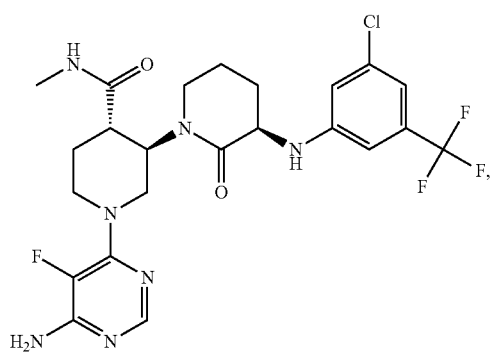
I-4
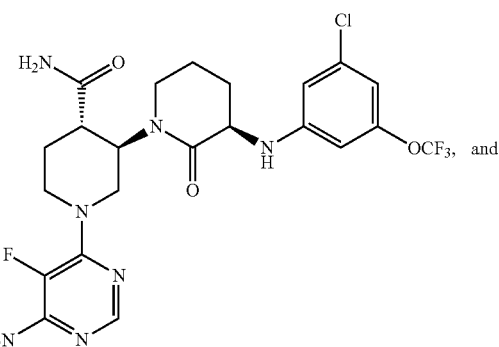
I-6
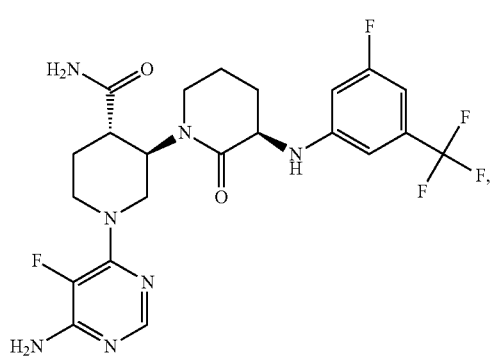
I-5
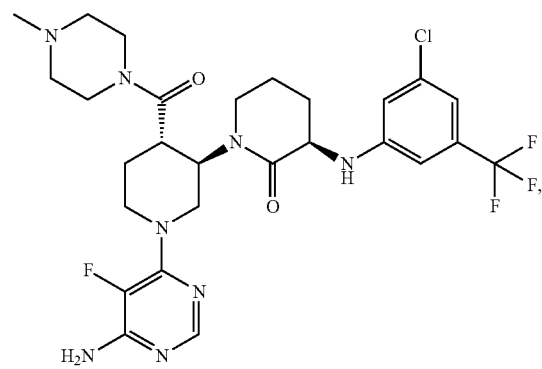
I-7
or a pharmaceutically acceptable salt thereof; and one or more pharmaceutically acceptable excipients.
* * * * *